(12) United States Patent
Ohnemus et al.

(10) Patent No.: US 11,462,327 B2
(45) Date of Patent: Oct. 4, 2022

(54) AUTOMATED HEALTH DATA ACQUISITION, PROCESSING AND COMMUNICATION SYSTEM

(71) Applicant: dacadoo ag, Zurich (CH)

(72) Inventors: Peter Ohnemus, Herrliberg (CH); Andre Naef, Zurich (CH); Manuel Heuer, Zollikon (CH); David Leason, Chappaqua, NY (US)

(73) Assignee: DACADOO AG, Zurich (CH)

( * ) Notice: Subject to any disclaimer, the term of this patent is extended or adjusted under 35 U.S.C. 154(b) by 109 days.

(21) Appl. No.: 15/313,513

(22) PCT Filed: May 26, 2015

(86) PCT No.: PCT/US2015/032462
§ 371 (c)(1),
(2) Date: Nov. 22, 2016

(87) PCT Pub. No.: WO2015/179868
PCT Pub. Date: Nov. 26, 2015

(65) Prior Publication Data
US 2017/0147775 A1    May 25, 2017

Related U.S. Application Data

(60) Provisional application No. 62/006,023, filed on May 30, 2014, provisional application No. 62/002,370, filed on May 23, 2014.

(51) Int. Cl.
*G16H 50/30* (2018.01)
*G16H 50/50* (2018.01)
(Continued)

(52) U.S. Cl.
CPC ............. *G16H 50/30* (2018.01); *G16H 10/20* (2018.01); *G16H 15/00* (2018.01); *G16H 20/30* (2018.01);
(Continued)

(58) Field of Classification Search
None
See application file for complete search history.

(56) References Cited

U.S. PATENT DOCUMENTS 6,110,109 A     8/2000 Hu et al.
6,514,199 B1    2/2003 Alessandri
(Continued)

FOREIGN PATENT DOCUMENTS

CN    101075274    11/2007
EP    0709058      5/1996
(Continued)

OTHER PUBLICATIONS

Guglielmo M Trovato, Behavior, nutrition and lifestyle in a comprehensive health and disease paradigm: Skills and knowledge for a predictive, preventive and personalized medicine, 3 EPMA Journal (2012), https://www.ncbi.nlm.nih.gov/pmc/articles/PMC3384462/pdf/1878-5085-3-8.pdf (Year: 2012).*

(Continued)

*Primary Examiner* — John P Go
*Assistant Examiner* — Nicholas Akogyeram, II
(74) *Attorney, Agent, or Firm* — Leason Ellis LLP

(57) ABSTRACT

A system and method are disclosed for computing a Health Score. Health data and extrinsic data are received that are parameters for computation of the Health Score. The received data can be combined using an algorithm being implemented as code executing in a processor so as to compute the Health Score of the individual wherein parameters comprising one portion of the data interacts with (Continued)

parameters comprising another portion of the data. Further, the computed Health Score is output to an interface of the user device. Information concerning the parameters' interaction are selectively output to the interface that explain which changes in the parameters are significant drivers of the change in the Health Score.

20 Claims, 35 Drawing Sheets

(51) Int. Cl.
  *G16H 15/00* (2018.01)
  *G16H 20/30* (2018.01)
  *G16H 20/60* (2018.01)
  *G16H 20/70* (2018.01)
  *G16H 10/20* (2018.01)

(52) U.S. Cl.
  CPC ............. *G16H 20/60* (2018.01); *G16H 20/70* (2018.01); *G16H 50/50* (2018.01)

(56) References Cited

U.S. PATENT DOCUMENTS

| | | | |
|---|---|---|---|
| 6,616,578 B2 | 9/2003 | Alessandri | |
| 6,751,657 B1 | 6/2004 | Zothner | |
| 7,034,691 B1 | 4/2006 | Rapaport | |
| 7,261,690 B2 | 8/2007 | Teller et al. | |
| 7,628,730 B1 | 12/2009 | Watterson et al. | |
| 8,075,450 B2 | 12/2011 | Fabbri et al. | |
| 8,135,863 B2 | 3/2012 | Nekovee | |
| 8,157,731 B2 | 4/2012 | Teller et al. | |
| 8,419,650 B2 | 4/2013 | Cosentino | |
| D688,585 S | 8/2013 | Ohnemus et al. | |
| 8,684,922 B2 * | 4/2014 | Tran ................ | G09B 19/00 600/300 |
| 8,706,530 B2 | 4/2014 | Ohnemus et al. | |
| D711,002 S | 8/2014 | Ohnemus et al. | |
| 8,873,815 B2 | 10/2014 | Ohnemus | |
| D723,585 S | 3/2015 | Brunner et al. | |
| 8,996,314 B2 | 3/2015 | Ohnemus et al. | |
| D742,414 S | 11/2015 | Brunner et al. | |
| D742,417 S | 11/2015 | Brunner et al. | |
| D744,538 S | 12/2015 | Brunner et al. | |
| D744,539 S | 12/2015 | Brunner et al. | |
| D744,540 S | 12/2015 | Brunner et al. | |
| D760,241 S | 6/2016 | Brunner et al. | |
| D761,806 S | 7/2016 | Brunner et al. | |
| D761,807 S | 7/2016 | Brunner et al. | |
| D763,267 S | 8/2016 | Brunner et al. | |
| 2001/0049470 A1 | 12/2001 | Mault et al. | |
| 2002/0055418 A1 | 5/2002 | Pyles et al. | |
| 2004/0133081 A1 | 7/2004 | Teller et al. | |
| 2005/0060194 A1 * | 3/2005 | Brown ................ | G06Q 30/02 705/2 |
| 2005/0076301 A1 | 4/2005 | Weinthal | |
| 2005/0165618 A1 | 7/2005 | Nerenberg | |
| 2005/0203773 A1 * | 9/2005 | Soto ................ | G06Q 40/08 705/2 |
| 2005/0228692 A1 | 10/2005 | Hodgdon | |
| 2006/0080149 A1 | 4/2006 | Takada et al. | |
| 2006/0206013 A1 | 9/2006 | Rothman et al. | |
| 2007/0027367 A1 | 2/2007 | Oliver et al. | |
| 2007/0161868 A1 | 7/2007 | Root | |
| 2007/0168230 A1 | 7/2007 | Roman | |
| 2007/0276203 A1 | 11/2007 | Day | |
| 2008/0089666 A1 | 4/2008 | Aman | |
| 2008/0146892 A1 | 6/2008 | LeBoeuf et al. | |
| 2009/0105047 A1 | 4/2009 | Guidi et al. | |
| 2009/0105550 A1 | 4/2009 | Rothman | |
| 2009/0113016 A1 | 4/2009 | Sen et al. | |
| 2009/0149717 A1 | 6/2009 | Brauer et al. | |
| 2009/0156363 A1 | 6/2009 | Guidi et al. | |
| 2009/0163774 A1 | 6/2009 | Thatha et al. | |
| 2010/0004945 A1 | 1/2010 | Petratos et al. | |
| 2010/0004947 A1 | 1/2010 | Nadeau et al. | |
| 2010/0082362 A1 | 4/2010 | Salsbury et al. | |
| 2010/0088264 A1 * | 4/2010 | Teverovskiy ......... | G16H 50/20 706/46 |
| 2010/0160743 A1 | 6/2010 | Jeong et al. | |
| 2010/0220914 A1 * | 9/2010 | Iwase ................ | A61B 5/0073 382/131 |
| 2011/0021936 A1 | 1/2011 | Luo | |
| 2011/0060576 A1 * | 3/2011 | Sharma ................ | G16H 50/50 703/11 |
| 2011/0069615 A1 | 3/2011 | Zhang et al. | |
| 2011/0125680 A1 * | 5/2011 | Bosworth ............. | G16H 50/30 706/12 |
| 2011/0201902 A1 * | 8/2011 | Shiga ................ | G16H 50/30 600/300 |
| 2011/0288379 A1 | 11/2011 | Wu | |
| 2012/0022886 A1 | 1/2012 | Ohnemus | |
| 2012/0042004 A1 | 2/2012 | Shenfield | |
| 2012/0117018 A1 | 5/2012 | Miller | |
| 2012/0171649 A1 | 7/2012 | Wander et al. | |
| 2012/0191469 A1 * | 7/2012 | Akradi ................ | G16H 50/30 705/2 |
| 2012/0296455 A1 | 11/2012 | Ohnemus | |
| 2012/0313776 A1 | 12/2012 | Utter, II | |
| 2013/0031189 A1 | 1/2013 | Lam | |
| 2013/0080181 A1 * | 3/2013 | DePetro ................ | G16H 40/67 705/2 |
| 2013/0095459 A1 * | 4/2013 | Tran ................ | A61B 5/021 434/247 |
| 2013/0158368 A1 | 6/2013 | Pacione et al. | |
| 2013/0211858 A1 | 8/2013 | Ohnemus et al. | |
| 2013/0217979 A1 | 8/2013 | Blackadar et al. | |
| 2013/0262357 A1 | 10/2013 | Amarasingham et al. | |
| 2013/0311197 A1 | 11/2013 | Hummer | |
| 2014/0088995 A1 | 3/2014 | Damani | |
| 2014/0099614 A1 * | 4/2014 | Hu ................ | G09B 19/00 434/236 |
| 2014/0110273 A1 * | 4/2014 | Bar-Or ................ | G01N 27/26 205/792 |
| 2014/0114680 A1 * | 4/2014 | Mills ................ | G16H 50/30 705/2 |
| 2014/0135592 A1 | 5/2014 | Ohnemus et al. | |
| 2014/0156308 A1 | 6/2014 | Ohnemus et al. | |
| 2014/0180583 A1 | 6/2014 | Doherty et al. | |
| 2014/0180598 A1 | 6/2014 | Stivoric | |
| 2014/0214441 A1 * | 7/2014 | Young ................ | G16H 50/20 705/2 |
| 2014/0221791 A1 * | 8/2014 | Pacione ................ | A61B 5/389 600/595 |
| 2014/0257047 A1 * | 9/2014 | Sillay ................ | H04L 63/10 600/595 |
| 2014/0316801 A1 * | 10/2014 | Oswald ............. | A63B 24/0062 705/2 |
| 2014/0316811 A1 | 10/2014 | Ohnemus et al. | |
| 2014/0324443 A1 * | 10/2014 | Ricks ................ | G06Q 50/10 705/14.17 |
| 2015/0169659 A1 | 6/2015 | Lee et al. | |
| 2015/0251074 A1 * | 9/2015 | Ahmed ................ | G06F 19/00 705/2 |
| 2016/0378921 A1 | 12/2016 | Ohnemus et al. | |
| 2017/0147788 A1 | 5/2017 | Ohnemus et al. | |
| 2018/0068083 A1 | 3/2018 | Cohen et al. | |
| 2018/0344215 A1 | 12/2018 | Ohnemus et al. | |
| 2018/0350451 A1 | 12/2018 | Ohnemus et al. | |

FOREIGN PATENT DOCUMENTS

| | | |
|---|---|---|
| EP | 1087824 | 4/2001 |
| EP | 1259153 | 11/2002 |
| EP | 1400264 | 3/2004 |
| EP | 2025368 | 2/2009 |
| JP | 2007-122182 | 5/2007 |
| JP | 2010-113668 | 5/2010 |
| JP | 2010-157079 | 7/2010 |
| JP | 2012-063910 | 3/2012 |

(56) References Cited

FOREIGN PATENT DOCUMENTS

| WO | WO 2004/032715 | | 4/2004 | | |
| WO | WO 2007/112034 | | 10/2007 | | |
| WO | WO 2009/026156 | | 2/2009 | | |
| WO | WO 2012/007850 | | 1/2012 | | |
| WO | WO 2012/050969 | | 4/2012 | | |
| WO | WO 2012/107497 | | 8/2012 | | |
| WO | WO 2012/156374 | | 11/2012 | | |
| WO | WO 2013/004706 | | 1/2013 | | |
| WO | WO 2011070831 | | 4/2013 | | |
| WO | WO-2013163627 | A1 * | 10/2013 | ........... | A61B 5/0002 |
| WO | WO 2014/091311 | | 6/2014 | | |
| WO | WO 2014/087252 | | 10/2014 | | |
| WO | WO 2017/091730 | | 8/2017 | | |

OTHER PUBLICATIONS

Matsubara, Atsushi, "12 Months of Macintosh—Broaden Your Lifestyle with Mac —Jun. 6, "Fitness with Mac&iPod"", Mac Fan, Japan, Mainichi Communications Inc., Jul. 1, 2008, vol. 16, No. 7, pp. 146-151 X.

"Wii Fit", Famitsu DS Plus Wii, Japan, Enterbrain, Inc., Feb. 1, 2008, vol. 10, No. 2, pp. 18-19X.

Ling Bao et al: "Activity Recognition from User-Annotated Acceleration Data". Mar. 23, 2004 (Mar. 23, 2004). Pervasive Computing; [Lecture Notes in Computer Science;;LNCS]. Springer-Verlag. Berlin/Heidelberg. pp. 1-17. XP019004314. ISBN: 978-3-540-21835-7 * the whole document * * in particular section 2 *.

Gyllensten I C et al: "Identifying Types of Physical Activity With a Single Accelerometer: Evaluating Laboratory-trained Algorithms in Daily Life" IEEE Transactions on Biomedical Engineering. IEEE Service Center. Piscataway. NJ. USA. vol. 1 • 58. No. 9. Sep. 1, 2011 (Sep. 1, 2011). pp. 2656-2663. XP011408471. ISSN: 0018-9294. DOI: 10.1109/TBME.2011.2160723 * the whole document * * in particular section II *.

Katherine Ellis et al: "Physical activity recognition in free-living from body-worn sensors". Proceedings of the 4th International Sensecam & Pervasive Imaging Conference on Sensecam '13. Nov. 18, 2013 (Nov. 18, 2013). pp. 88-89. XP055598839. New York. New York. USA DOI: 10.1145/2526667.2526685 ISBN: 978-1-4503-2247-8 * the whole document *.

Muthukumar Kumar: "Google's Activity Recognition API is awesome but where are the apps?—Geoawesomeness" Nov. 10, 2015 (Nov. 10, 2015). XP055599007. Retrieved from the Internet: URL:https:jjgeoawesomeness.comjgoogles-activity-recognition-api-is-awesome-but-where-are-the-apps/ [retrieved on Jun. 24, 2019] * the whole document *.

Anonymous: "CMMotionActivity—Core Motion : Apple Developer Documentation" Dec. 31, 2013 (Dec. 31, 2013). XP055599008. Retrieved from the Internet: URL:https://developer.apple.com/documentation/coremotion/cmmotionactivity [retrieved on Jun. 24, 2019] * the whole document *.

Bodhi Priyantha et al: "EERS: Energy Efficient Responsive Sleeping on Mobile Phones", International Workshop on Sensing for App Phones (PhoneSense), Nov. 2, 2010 (Nov. 2, 2010), XP055192517, Zurich, Switzerland Retrieved from the Internet: URL:http://sensorlab.cs.dartmouth.edu/phonesense/papers/PriyanthaEERS.pdf.

\* cited by examiner

Manual Data Entry

MANUAL ENTRY
Please use this form to insert a manual entry into your journal. Workouts can be entered for up to 30 days of history.

Activity
Please choose an activity from the list below.
Activity: [ General Work out Session ▼ ]

Date
Please enter the date and time of your workout.

| Mo | Tu | We | Th | Fr | Sa | Su |
|----|----|----|----|----|----|----|
|    |    |    | 1  | 2  | 3  | 4  |
| 5  | 6  | 7  | 8  | 9  | 10 | 11 |
| 12 | 13 | 14 | 15 | 16 | 17 | 18 |
| 19 | 20 | 21 | 22 | 23 | 24 | 25 |
| 26 | 27 | 28 | 29 | 30 |    |    |

Time [ 10 ▼ ] : [ 00 ▼ ]

Values
Please fill in the value fields to the extent they are applicable to your workout and the information is at your disposal. The energy is calculated automatically based on the information you provide, unless you specify the energy yourself.

Duration [ ] h [ ] min
Distance [ ] km (optional)
Ascent [ ] m (optional)
Heart Rate [ ] BPM (optional)
Energy [ ] kcal (optional)
Picture [ Choose File ] No file chosen (supported types: PNG JPEG GIF) (optional)

[ Manual Entry ] [ Cancel ]

AUTOMATED HEALTH DATA ACQUISITION, PROCESSING AND COMMUNICATION SYSTEM

CROSS-REFERENCE TO RELATED APPLICATIONS

The present application is a U.S. National Phase of International Patent Application PCT/US2015/032462, filed on May 26, 2015, which is based on and claims priority to U.S. Provisional Patent Application No. 62/002,370, filed May 23, 2014, and further which is based on and claims priority to U.S. Provisional Patent Application No. 62/006,023, filed May 30, 2014, the contents of each of which is hereby incorporated by reference as if set forth in their respective entireties herein.

FIELD OF THE INVENTION

The present application relates, generally, to networking and, more particularly, to a data acquisition, processing and communication system relating to an individual's health.

BACKGROUND OF THE INVENTION

Despite advances in many areas of technology, there are still barriers to assessing the relative health of a person in a rapid, cost effective and timely manner. With the increase in health care costs and prevalence of diseases related to unhealthy lifestyles, such as diabetes and heart disease, it is important to assess the relative health of individuals, and this has not been adequately addressed. Moreover, in many areas of the world, access to doctors is limited. Even in areas of the world where access to physicians is considered excellent, a doctor's time is considered a precious commodity and there are often long waiting lists and doctor-to-specialist referral systems have to be navigated before a patient is seen. In more developed countries the ratio of doctors to the population can be on the order of 1:1,000 persons, while in less developed countries the ratio can be 1:100,000. There are also cost barriers to having access to a doctor because an appointment with a doctor can be very expensive, especially if an individual does not have any health insurance or lacks sufficient coverage. Accordingly, it can be very difficult to gain access to medical professionals in order to receive information about one's health.

Even individuals that have access to his or her health information, the mechanisms for conveying that information to others is lacking or non-existent. Privacy laws restrict the type of information that can be shared and the manner in which it can be shared. Privacy laws relating to health information are particularly strict in regard to the information that can be shared. This is to protect a person from disclosure of sensitive information. Accordingly, the sharing of health related information is generally discouraged. It is also difficult to share health related information with friends and family. Often health information is only verbally conveyed by a doctor to a patient, or the patient will only receive paper copies of lab test results. Systems are lacking for easily sharing such information with others, especially with large groups of persons located in geographically remote locations.

Furthermore, programs aimed at improving an individual's diet are usually based on an assessment of the type and the amount of food consumed using so called Food Frequency Questionnaires (FFQs). Based on the results, the programs give a "roadmap." For most users, this "roadmap" is relatively easy to follow and many of them achieve their nutritional goals. Unfortunately, many changes fail to become second nature to the user, and he or she often reverts back to 'old' behaviors. Another limitation of FFQs is that people tend to forget when and what they eat and often underestimate the amount and frequency of eating. Accurate documentation is also a laborious and time-consuming task, which often leads to loss of motivation.

The present application addresses these and other concerns.

SUMMARY OF THE INVENTION

In one or more implementations, the present application includes a system and method for computing a Health Score of an individual. Health data and extrinsic data are received that are parameters for computation of the Health Score. The received data can be combined using an algorithm being implemented as code executing in a processor so as to compute the Health Score of the individual wherein parameters comprising one portion of the data interacts with parameters comprising another portion of the data. Further, the computed Health Score is output to an interface of the user device. Information concerning the parameters' interaction are selectively output to the interface that explain which changes in the parameters are significant drivers of the change in the Health Score.

In one or more implementations, the Health Score is presented in the interface as falling in one of a plurality of predefined bands. Moreover, the bands can comprise a relative scale in comparison to fixed percentile criteria. Alternatively (or in addition), the bands are presented in a color-coded manner within the interface.

In one or more implementations, code is executed in the processor to configure the processor to simulate score evolution using a trend in the extrinsic data. Additionally, an analytical engine is provided that comprises code executing in the processor to configure the processor to set, combine, arrange and/or calculate values for one or more of the parameters. The analytical engine can utilize one or more mathematical models in computing the Health Score, which can include a cardiovascular risk model or a lifestyle model.

Various features, aspects and advantages of the invention can be appreciated from the following Description of Certain Embodiments of the Invention and the accompanying Drawing Figures.

BRIEF DESCRIPTION OF THE DRAWING FIGURES

FIGS. 4B and 4C illustrate example data entry display screens and controls in accordance with an implementation of the present application;

FIG. 12 illustrates an example display screen associated with a public challenge, in accordance with an implementation of the present application;

DESCRIPTION OF CERTAIN EMBODIMENTS

Figure 1:
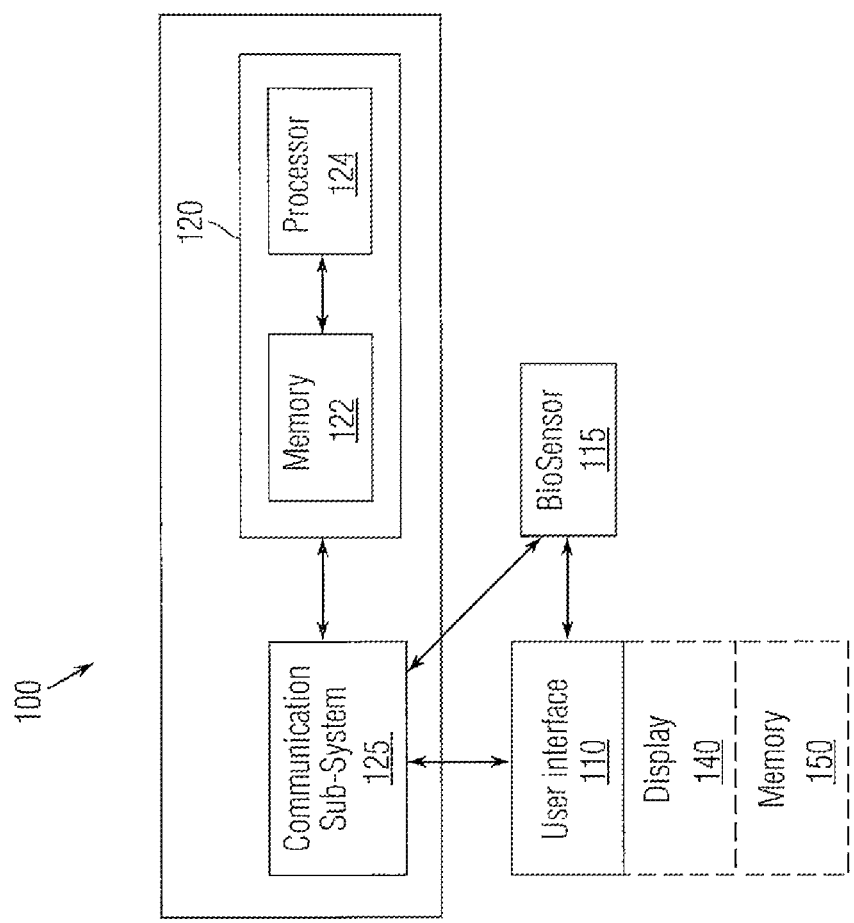
FIG. 1 is a schematic block diagram of a local health information collection and communication system according to a first implementation of the invention.

In one or more example implementations, the present application provides a computer-implemented system and method configured to acquire health-related and/or medical-related data, and to process the data, for example, for diagnostic, benchmarking, analytic and/or data distribution (e.g., reporting) purposes. For example, the systems and methods herein provide feedback substantially in real-time via an on-line and/or mobile platform. Using the systems and methods disclosed herein, information can be received from user devices, and the information can be processed to provide various forms of feedback, such as alerts and notifications. Related information can be, thereafter, received and processed for additional feedback (e.g., a form of a feedback loop).

In one or more implementations, one or more rule engines can be provided that periodically and/or continuously process information and that generate notifications to users. Implementations can depend on a respective subsystem (e.g., data gathering subsystems, data communication subsystems, data processing subsystems) and one or more corresponding notification features. Moreover, one or more notification generating rule engines can be part of individual subsystems generating notifications. The notification features can include core information elements that are useful for the feedback process. Generally, notifications can include questionnaires and/or prompts for information, and can be presented by an interactive interface, such as an avatar. The result can include an infrastructure configured for scheduling, processing, and delivering notifications over various communication channels and formats.

In accordance with one or more implementations, a respective notification type can be assigned to a domain. Moreover, users can choose a respective "channel" used by server 180 and/or client 160 (FIG. 1) for sending notifications based on the respective domain of a notification. For example, the following notification domains can be supported: Social; Personal Progress; Requests/Reminders for Input; and Private Messaging. Further, a default set of one or more channels can be assigned to each domain, which can be overridden by users. For example, the following channels can be supported: Internet web site; mobile device software application ("mobile app"); e-mail; SMS; and mobile device push. Notifications can also be exported to a partner system, such as a customer relations management ("CRM") system, for further processing. On the web and/or in a mobile app, a user interface can include a suitable inbox for users to review notifications easily and quickly. The user interface can distinguish between notifications that can be new and previously reviewed.

Notifications generated by one or more rule engines can be assigned a priority between zero and one, which priority can be static or be calculated dynamically, based on the specific content/parameters of the notification. In order to prevent users being overwhelmed with excessive amounts of information, notifications can be provided in accordance with various system parameters. For example, a cap specifying a maximum number of notifications of a particular type that is delivered per interval can be employed. If the cap is surpassed, then only those notifications assigned a high priority may be pushed to the user. Users can at least partially influence the cap by selecting an option for notifications, such as "show me more/less of this" functionality in a user interface ("UI"). In addition, a cool-down value can be employed that specifies a minimum amount of time that should pass between notifications of a specific type or that meet specific content/parameters. Moreover, a folding function can be used by server 180 and/or client 160 (FIG. 1) to combine multiple notifications into one (e.g., folding three friend suggestions into a single notification).

In one or more implementations, sensed information of the type that is associated with at least one of biological information, physiological information and physical activity of the user can be received from one or more devices is configured to sense information.

In addition to displaying or otherwise providing information representing a user's activity, as well as biological and/or physiological information associated with a user, the present application can be configured to provide reminders and/or notifications that are associated with adherence to medication, behavior (e.g., activity or abstaining from certain activity), or for monitoring one or more medical conditions. In addition to displaying information, a vibration mechanism (as known in the art) or other suitable configuration can be provided to provide an alert to a user. The user's cell phone, for example, can vibrate to alert the user, for example, to take medication (e.g., a beta blocker, diabetes II medicine, blood pressure medication, or the like). Alternatively, the alert may remind the user to take some action, such as to draw blood, to check blood glucose levels, to check heart rate or blood pressure, or to take some other action, such as to exercise (e.g., take a walk or participate in a challenge), or to consume food (or stop consuming food).

In one or more implementations, information, such as health-related information, alerts, notifications or the like, can be provided at the computing device via a user interface substantially contemporaneously with the reception of the sensed information.

In addition, the present application can be configured with one or more speakers and audio components to provide audio information. In addition, a microphone can be provided to receive voice commands and/or audio input. Moreover, a camera can capture still and/or moving images. The ability to send and receive multimedia content (e.g., audio and/or visual content) provides additional functionality, for example, for the user to interact with others in various ways.

In addition, information can be processed and associated with exercise and various kinds of workouts. Information, such as kilometer times, significant changes in heart rate, or guided training information, such as interval trainings, can be provided to a user substantially in real-time during exercise. Information may be displayed, and/or provided as multimedia-content.

In one or more implementations, the present application provides a notification scheduler that accepts notifications for delivery to users via particular channels. Once a notification has been submitted to the scheduler service, the notification can be placed in a queue, and one or more processors can then operate on the notifications queue(s). For example, each processor, while running on a queue, can take actions such as dropping, delivering, keeping or folding notifications. This provides for significant flexibility. For example, it is possible to keep each notification queued for a particular (or arbitrary) amount of time. Even holding a notification for a very short amount of time can significantly increase the chance of folding a notification with another notification that is generated only a small fraction of time later.

In operation, an initial testing process may be provided in which questions and/or information is presented, and users can be offered an opportunity to respond, such as to determine whether the content is understandable/clear, meaningful, relevant, fun and/or entertaining. Additionally, free-text responses may be provided via voice-input, text-input controls (e.g., text boxes), or other graphical screen elements. Responses to questions can be answered via a graphical slider control that provides options, such as "not at all" to "very much," which can correspond to numerical values, such as 0.0 to 1.0. This information can be stored together with the date of submission and user identifier, such as an anonymous user ID. In one or more implementations, repeated submissions that are received by the same user (or user device) relating to the same topic can overwrite the previous submission. Further, a simple text report showing the mean value and standard deviation of the answers, followed by one or more received (i.e., non-empty) comments can be provided. Moreover, a notification catalog can be provided that can be operable as a function of declarative logic, and with relatively little specific programming to implement the one or more rules engines.

By way of further overview and introduction, the present application is described in detail in connection with a distributed system in which data acquisition, data storage, and data processing can be used by server 180 and/or client 160 (FIG. 1) to produce a numerical score as a basis for assessing the relative health of a user. Referred to herein, generally, as a "Health Score," a value can be calculated and used to assess to the individual's health based on health related information collected from a user and other sources. The Health Score can be calculated based on the collected health information using an algorithm. The user or a communication subsystem provides the health-related information, for example in connection with one or more health parameters. Predetermined weighting factors can be used to assign a relative value of each of the parameters that are used by server 180 and/or client 160 to calculate the Health Score. The user's Health Score can be then calculated by combining the weighted parameters in accordance with an algorithm. By providing the Health Score, a user gets health-related feedback information and can make modifications in his/her lifestyles that can directly impact the user's Health Score and improve the user's health, more generally.

In one or more implementations, the present application can calculate an "Effective Age" value, which represents an age that can be associated with the user based upon biometric and other information attributed to calculating the user's Health Score, notwithstanding the user's actual age. As a user modifies his or her lifestyle, which impacts the user's Health Score, and submits responses to data entry controls set forth in a user interface representing the changes, server 180 and/or client 160 uses the information to calculate and display to the user changes to the user's effective age.

In accordance with the present application, three interrelated components can be included in calculating the user's Health Score: a metric health model ("MHM"), which includes subjective information from the user about who the user is; a quality of life model ("QLM"), which includes subjective information from the user about how the user feels; and a lifestyle model ("LSM") which includes subjective information from the user about how the user lives. One or more weighting factors can be applied to each of these components. These components can be represented as percentage values. For example for MHM the weighting factor can be 35%, for QLM the weighting factor can be 20%, and for LSM the weighting factor can be 45%. The percentages can be static values, or can be dynamic. Example categories of input information that contribute to the values can include demographic information and anthropomorphic information (e.g., age, ethnicity, gender, height, weight, body-mass index and waist circumference), familial information (such as family histories, e.g., premature CVD, Diabetes, angina, heart attack hypertension), metabolic information (e.g., total serum cholesterol, high-density lipoprotein tsc/hdl, low-density lipoprotein, triglycerides, fasting blood glucose, systolic blood pressure, diastolic blood pressure, C-reactive protein, resting heart rate, and percent body fat), lifestyle-derived information (e.g., daily smoking and alcohol intake), pre-existing conditions (e.g., left ventricular hypertrophy, Type II Diabetes mellitus, hypertension, arrhythmia, Chronic Kidney Disease, MI, stroke, TIA, or Congestive Heart Failure) and self-assessment information. If fat is given in the input for MHM, the BMI may be generated by an internal function fat2bmi( ) with the BMI in the input, and it will take the smaller of the two.

In addition to calculating the Health Score by using estimates of cardiovascular and other risks associated with measurable parameters, such as blood pressure, weight, lipid levels or the like, the present application can include one or more modules to apply information associated with the MHM, QLM and LSM to further determine and/or estimate health risks. For example, risks associated with the most common vascular and other biological elements can be derived from the results of information from medical studies, and which can be modified over time to provide consistency. A score associated with the MHM, for example, can include three factors that cover a broad set of disease end-points and associated risk factors: a) direct vascular risks, which estimate the risks associated with major vascular events, such as stroke, or myocardial infarction; b) predecessor risks, which estimate the risks associated with major vascular risk factors, such as Type 2 diabetes or hypertension; and c) modulator risks, which scale the overall risk using risk factors not included in the other two components, such as alcohol consumption or certain aspects of nutrition. These modulator factors include parameters from both the QLM and LSM. Each of these components can include several models that can be combined to produce a single estimate of a health-risk event. The overall risk can be transformed into a score between 0 and 1,000, with 1,000 signifying perfect, but unattainable health.

In one or more implementations, a process of verifying data integrity in multiple stages can be provided. For example, input data structures include metadata that is processed and used by server 180 and/or client 160 (FIG. 1) to calculate a Health Score. The metadata can include various attributes in a first stage of the verification process, such as: required data, minimum value(s), maximum value(s), and default value(s). Data can be first checked for completeness, and values for missing data fields that passed the first stage can be imputed using one or more models, for example, based on the use of required fields only.

In connection with the Quality of Life model, a server 180 and/or client 160 can generate and provide a warning to a user after the first quality of life questionnaire is completed. In the event that a value is received that is above the 96th percentile of original survey data, a message, such as a warning, can be generated that the user's responses appear to be unrealistic, and inviting the user to repeat the process to generate a new score. The message can include a statement that the benefit of the score would be lost if it is not taken seriously. In an embodiment, subsequent updates of a questionnaire are not checked for a determination of realistic values.

In accordance with the present application, one or more components can be factored into a measurement to determine an extent to which lifestyle characteristics can impact a user's future health. Examples of such components include fitness, nutrition, background physical activity, stress reduction, weight management, and smoking cessation. Two or more of these components can interrelate, which can be reflected in an associated individual and overall Health Scores. The weights with which the components contribute to an overall lifestyle score can be determined dynamically from two factors: (1) the sensitivity of the MHM score to changes in a set of modifiable risk factors (MRF) for a given user, and (2) a sensitivity matrix that relates the effect of each lifestyle component on each of the MRF. This mechanism leads to a recommendation to the user, based on a ranking in accordance with relevance of the factors that relate to the user's changing lifestyle. Further, the weights associated with each lifestyle component that contributes to the Health Score can be modified, with the most relevant factor receiving the highest weight. In one or more implementations, the priority of lifestyle components is provided to the user in a simple and visually compelling manner.

Also and in accordance with one or more implementations, the complete (or partial) Health Score can be validated in a prospective study. In such case, a collaboration of a sufficiently large cohort of users is used for those who regularly and periodically provide accurate data, and for whom health outcomes over time are available.

In one or more implementations, the LSM represents health-improvement efforts taken by a user and corresponding health-related consequences thereof. A percentage value can be attributed to the LSM component can be higher than, for example, the MHM or QLM components. Moreover, in an embodiment, various categories can be employed to monitor and quantify lifestyle characteristics that are strongly correlated with overall health. The categories can include fitness, nutrition, stress, background physical activity, weight-management and smoking cessation. These can be quantified, for example, using a double-buffer method, including a score component, a bonus component and a decay function, which can vary in value depending upon a particular lifestyle component.

Generally, each of the lifestyle components generates a score, such as in a range of 0-1,000. The scores can be combined using a dynamic weighing scheme based on the relevance of each for a given user and at a given time. The weights can be proportional to the relevance to the user at any given time. A discussion regarding an example weighing scheme in accordance with one or more implementations is provided below.

In an embodiment, a plurality of components is factored in a calculation of the MHM. For example, precursor risks are considered, in which a number of risk factors are used by server 180 and/or client 160 to determine a probability of developing a disease, such as a cardiovascular and/or cerebrovascular disease and certain cancers. Such probability may be estimated using a set of models derived from studies, which can be modified for consistency. The time horizon for these risks can be defined, for example, at four years, and the derived probabilities can be used in place of binary risk factors that can be used in the core risk models. In one or more implementations, the diseases and syndromes included as precursors are: chronic kidney disease; diabetes mellitus type II; hypertension; Metabolic Syndrome; and peripheral arterial disease.

In addition, several risk factors may be derived from lifestyle and metabolic characteristics. These risk factors may be not directly included in the core risk models that are quantified using models and data from studies, and can be used either as overall risk multipliers for an appropriate core risk model, or as remnant risks, such as in the case of smoking cessation. Examples of risks and factors as risk modulators can include: alcohol consumption; physical activity; nutrition; resting heart rate; heart rate recovery; smoking cessation; chronic stress; and depression. The input data for these models can include several sources, including inputs associated with family, demographics and metabolism, as well as other user inputs and parameters derived by internal models that use the inputs, data derived from the Quality of Life model, and data collected from one or more processes, substantially as shown and described herein.

In one or more implementations, a Metric Health Score includes a plurality of central estimators, which can be derived from data and one or more models, such as from one or more studies. The models can be modified and/or updated to provide an accurate Metric Health Score. Moreover, the models can be rescaled to produce approximate event probabilities for a fixed time horizon of time, such as for 10 years.

Examples of diseases and end-points included in various calculations can be general cardiovascular disease; coronary heart disease; congestive heart failure; myocardial infarction and stroke. In one or more particular cases, particular studies can include severity modifiers, such as death.

In connection with core risk models, weights and combinations thereof can be employed. For one or more diseases or end-points, several models can be included, which can result in given condition(s) that are combined using, for example, conservative probabilistic logic, and that can be internally weighted by the relative severity of the respective end-point under consideration. These individual estimates of risk can then themselves be weighted by relative severity and combined into an overall event probability, from which a score, such as ranging from 0-1,000 can derive a series of transformations. The parameters of these transformations also can be derived using data from known sources, such as the National Health and Nutrition Examination Survey (NHANES). Further, the Metric Score can be equalized to account for gender and age.

In accordance with the present application a recommendation or "focus engine" can be provided that informs users of one or more lifestyle components that the users should focus on to increase their Health Score efficiently. Users are provided with a prescription to focus on specific lifestyle issues to improve long-term health. The engine can do this by first calculating a user's room for improvement in the modifiable risk factors ("MRF"). Example modifiable risk factors can include, for example, weight, body-mass index, waist circumference, total serum cholesterol, high-density lipoprotein, low-density lipoprotein, triglycerides, fasting, blood glucose, systolic blood pressure, diastolic blood pressure, C-reactive protein, resting heart rate, heart rate recovery, percent body fat, and smoking status. A calculation can be made regarding the difference in Health Score between a user's current value, and the value that would result if the user's MRF were ideal, e.g., at best values. It is recognized herein that a user may find that thinking in terms of MRF can be too abstract. For this reason, in a next step, the engine can calculate the combined weight of the MRFs for each lifestyle component. Lifestyle components, such as nutrition or fitness, are things that users may be more willing or able to relate to. Thus, presenting those lifestyle components ordered by the calculated weight gives a clear guidance to users as to which lifestyle components have the strongest effect on their overall Health Scores and thus on their wellbeing.

The effect of changing any particular MRF from a current value to an ideal, best value can be quantified by determining the difference between the corresponding two metric Health Scores, thus producing a first recommendation, namely to focus on the MRF that produces the largest effect. In case this is construed to be overly abstract and/or unusable, a recommendation can be expressed in terms of lifestyle changes that most efficiently address the specific MRF. This results in a recommendation that is more usable and understandable for the user. For each of the MRF, $M_k$, there is an effect, $E_k = MHM(\{M_k\}) - MHM(\{M_k | I_k\})$, where h is the ideal value for the $k^{th}$ MRF.

To convert MRF modification to lifestyle change, a static matrix, referred to herein, generally, as a sensitivity matrix can be used. In accordance with this matrix, the columns represent the current lifestyle components, and the rows represent the MRF. The values can be a ranking of the lifestyle components by their effect on each of the MRF.

A discussion regarding respective component weights is now provided. In case $S_{nm}$ is the rank (normalized to [0,1]) of the effect of the $n^{th}$ lifestyle factor on the $m^{th}$ MRF, one can define weights $w_n$ for each of the lifestyle factors as follows:

$$w_n = \frac{\overline{w}_n}{\sum_{m \neq n} \overline{w}_n}$$

where $$\overline{w}_n = \sum_m S_{nm} E_m$$

The engine can return $w_n$ as defined above to the platform, which can be used by server 180 and/or client 160 (FIG. 1) as relative weights for one or more of the lifestyle scores. The individual weighted scores, when summed and linearly normalized into the 0-1,1000 interval, define the overall Lifestyle Score, and 45% of the overall Health Score.

In addition to a focus engine, in one or more implementations the present application can include a recommendation normalization and engine. This can employ two lifestyle components: a fitness component; and a smoking cessation component (which can be active for current and previous smokers). Ranking is supported, and can use one or more other components, leading to a simple focus list. For example, a recommendation may be made that states, "the best immediate approach to increase a Health Score is to concentrate on fitness activities and improve your nutrition." This can be used even if there is no active nutrition tracker. In one or more implementations, to compute the Lifestyle Score, the platform can first renormalize the score to include only those components and trackers that are activated by the user.

As will become clear in accordance with the teachings herein, a sedentary lifestyle in most societies has dramatically increased the proportion of people who are overweight, have diabetes or suffer from heart failure, pressuring further the already stressed healthcare budgets of most developed countries. Insufficient activity has nearly had the same effect on life expectancy as smoking.

Referring now to the drawings figures in which like reference numerals refer to like elements, there is shown in FIG. 1 an example implementation represented as a system 100 that includes a computer-based application for the collection of health related parameters of a user and a user interface 110 for the display of data. The computer-based application is implemented via a microcontroller 120 that includes a processor 124, a memory 122 and code executing therein so as to configure the processor to perform the functionality described herein. The memory is for storing data and instructions suitable for controlling the operation of the processor. An implementation of memory can include, by way of example and not limitation, a random access memory (RAM), a hard drive, or a read only memory (ROM). One of the components stored in the memory is a program. The program includes instructions that cause the processor to execute steps that implement the methods described herein. The program can be implemented as a single module or as a plurality of modules that operate in cooperation with one another. The program is contemplated as representing a software component that can be used in connection with an embodiment of the invention.

A communication subsystem 125 is provided for communicating information from the microprocessor 120 to the user interface 110, such as an external device (e.g., handheld unit or a computer that is connected over a network to the communication subsystem 125). Information can be communicated by the communication subsystem 125 in a variety of ways including Bluetooth, WiFi, WiMax, RF transmission, and so on. A number of different network topologies can be utilized in a conventional manner, such as wired, optical, 3G, 4G networks, and so on.

The communication subsystem can be part of a communicative electronic device including, by way of example, a smart phone or cellular telephone, a personal digital assistant (PDA), netbook, laptop computer, and so on. For instance, the communication subsystem 125 can be directly connected through a device such as a smartphone such as an iPhone, Google Android Phone, BlackBerry, Microsoft Windows Mobile enabled phone, and so on, or a device such as a heart rate or blood pressure monitor (such as those manufactured by Withings SAS), weight measurement scales (such as those manufactured by Withings SAS), exercise equipment or the like. In each instance, the devices each comprise or interface with a module or unit for communication with the subsystem 125 to allow information and control signals to flow between the subsystem 125 and the external user interface device 110. In short, the communication subsystem can cooperate with a conventional communicative device, or can be part of a device that is dedicated to the purpose of communicating information processed by the microcontroller 120.

When a communicative electronic device such as the types noted above are used as an external user interface device 110, the display, processor, and memory of such devices can be used to process the health related information in order to provide a numerical assessment. Otherwise, the system 100 can include a display 140 and a memory 150 that are associated with the external device and used to support data communication in real-time or otherwise. More generally, the system 100 includes a user interface, which can be implemented, in part, by software modules executing in the processor of the microcontroller 120 or under control of the external device 130. In part, the user interface can also include an output device such as a display (e.g., the display 140).

Biosensors 115 can be used to directly collect health information about a user and report that information. The biosensor can be placed in contact with the user's body to measure vital signs or other health related information from the user. For example, the biosensor can be a pulse meter that is worn by the user in contact with the user's body so that the pulse of the user can be sensed, a heart rate monitor, an electrocardiogram device, a pedometer, a blood glucose monitor or one of many other devices or systems. The biosensor can include a communication module (e.g., communication subsystem 125) so that the biosensor can communicate, either wired or wirelessly, the sensed data. The biosensor can communicate the sensed data to the user interface device, which in turn communicates that information to the microcontroller. Optionally, the biosensor can directly communicate the sensed the data to the microprocessor. The use of biosensors provides a degree of reliability in the data reported because it eliminates user error associated with manually, self-reported data.

Figure 2:
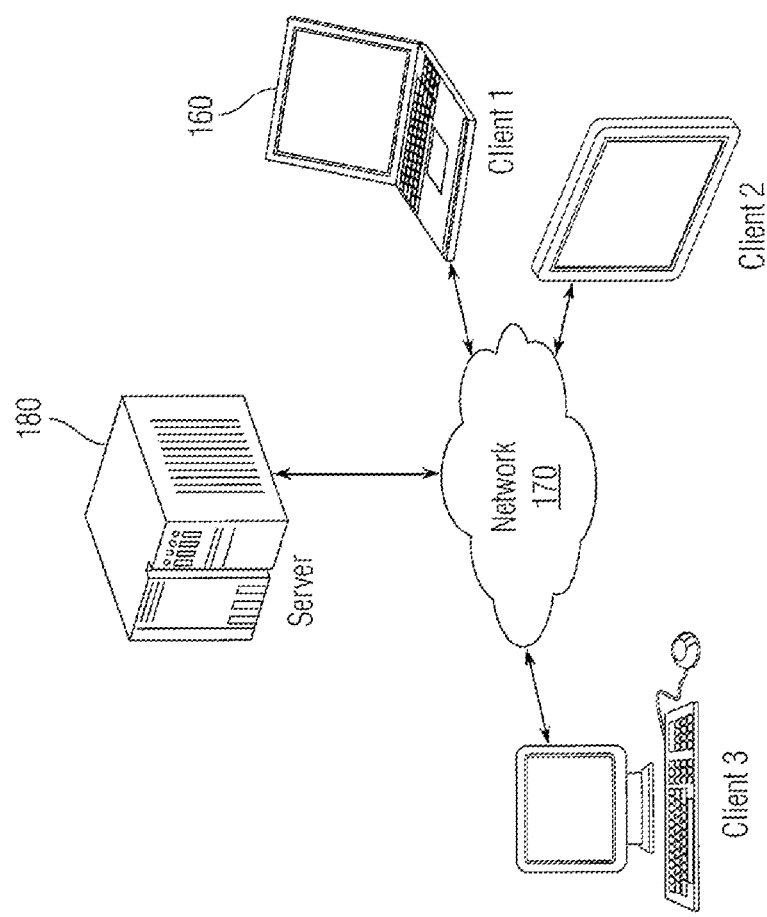
FIG. 2 is a network diagram according to another implementation of the invention.

Alternatively or in addition, the user can self-report his or her health related information by manually inputting the data. Thus, in another implementation, as shown in FIG. 2, health related data of a person is entered directly into a computer 160 and provided across a network 170 to a server computer 180. (All computing devices described herein have at least one processor and a memory.)

Server 180 preferably includes all necessary databases for the present application, including image files, metadata and other information. However, it is contemplated that server 180 can access any required databases via network 170 or any other communication network to which server 180 has access. Server 180 can communicate devices comprising databases using any known communication method, including a direct serial, parallel, USB interface, or via a local or wide area network.

Clients 160 communicate with servers 180 using data connections, which are respectively coupled to network 170. Network 170 can be any communication network, but is typically the Internet or some other global computer network. Data connections can be any known arrangement for accessing network 170, such as dial-up serial line interface protocol/point-to-point protocol (SLIPP/PPP), integrated services digital network (ISDN), dedicated leased-line service, broadband (cable) access, frame relay, digital subscriber line (DSL), asynchronous transfer mode (ATM) or other access techniques.

Clients 160 preferably have the ability to send and receive data across network 170, and can be equipped with web browsers or other suitable software (e.g., a mobile app or "app") to display the received data on display devices incorporated therewith. By way of example, client 160 may be personal computers such as Intel Pentium-class computers, but are not limited to such computers. Other clients which can communicate over a global computer network such as smartphones, tablet computers, personal digital assistants (PDAs) and mass-marketed Internet access devices such as WebTV can be used. In addition, the hardware arrangement of the present application is not limited to devices that are physically wired to network 170. Of course, one skilled in the art will recognize that wireless devices can communicate with servers 180 using wireless data communication connections (e.g., Wi-Fi, ANT+, Bluetooth Low Energy ("BLE") or ZigBee).

In one or more implementations, the device in accordance with the present application can be configured to include a head-worn display that is configured to send, receive and display information as shown and described herein. For example, the present application may be configured with or in GOOGLE GLASS.

According to an embodiment of the present application, client 160 provides user access to server 180 for the purpose of receiving and providing information, including relating to the user's health. The specific functionality provided by system 100, and in particular servers 180, is described in detail below.

System 100 preferably includes software that provides functionality described in greater detail herein, and preferably resides on one or more servers 180 and/or clients 160. One of the functions performed by server 180 is that of operating as a web server and/or a web site host. Servers 180 typically communicate with network 170 across a permanent i.e. unswitched data connection. Permanent connectivity ensures that access to servers 180 is always available.

The various components of server 180 need not be physically contained within the same chassis or even located in a single location. For example, as explained above with respect to databases which can reside on a storage device, a storage device may be located at a site which is remote from the remaining elements of servers 180, and may even be connected to a CPU across a network 170 via a network interface.

The functional elements set forth in server 180 can be of the same categories of functional elements present in client 160. However, not all elements need be present, for example, storage devices in the case of PDAs, and the capacities of the various elements are arranged to accommodate expected user demand. For example, a CPU in client 160 may be of a smaller capacity than a CPU as present in server 180. Similarly, it is likely that server 180 will include one or more storage devices of a much higher capacity than present in client 160. Of course, one of ordinary skill in the art will understand that the capacities of the functional elements can be adjusted as needed.

The nature of the present application is such that one skilled in the art of writing computer executed code (software) can implement the described functions using one or more or a combination of a popular computer programming language including but not limited to C++, VISUAL BASIC, JAVA, ACTIVEX, HTML 5, XML, ASP, SOAP, OBJECTIVE C, and C# and various web application development environments.

As used herein, references to displaying data on client 160 refer to the process of communicating data to the workstation across network 170 and processing the data such that the data can be viewed on the client 160 display using a web browser or the like. The display screens on client 160 present areas within system 100 such that a user can proceed from area to area within the system 100 by selecting a desired link. Therefore, each user's experience with system 100 will be based on the order with which (s)he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of system 100.

Although the present application is described by way of example herein in terms of a web-based system using web browsers, a web site server and with mobile computing devices, system 100 is not limited to that particular configuration. It is contemplated that system 100 can be arranged such that user computing device can communicate with, and display data received from, server 180 using any known communication and display method, for example, using a non-Internet browser Windows viewer coupled with a local area network protocol such as the Internetwork Packet Exchange (IPX). It is further contemplated that any suitable operating system can be used on client 160, for example, WINDOWS XP, WINDOWS 7, WINDOWS 8, MAC OS, LINUX, IOS, ANDROID, WINDOWS PHONE 7, WINDOWS PHONE 8, and any other suitable PDA or mobile computing device operating system.

Figure 3A:
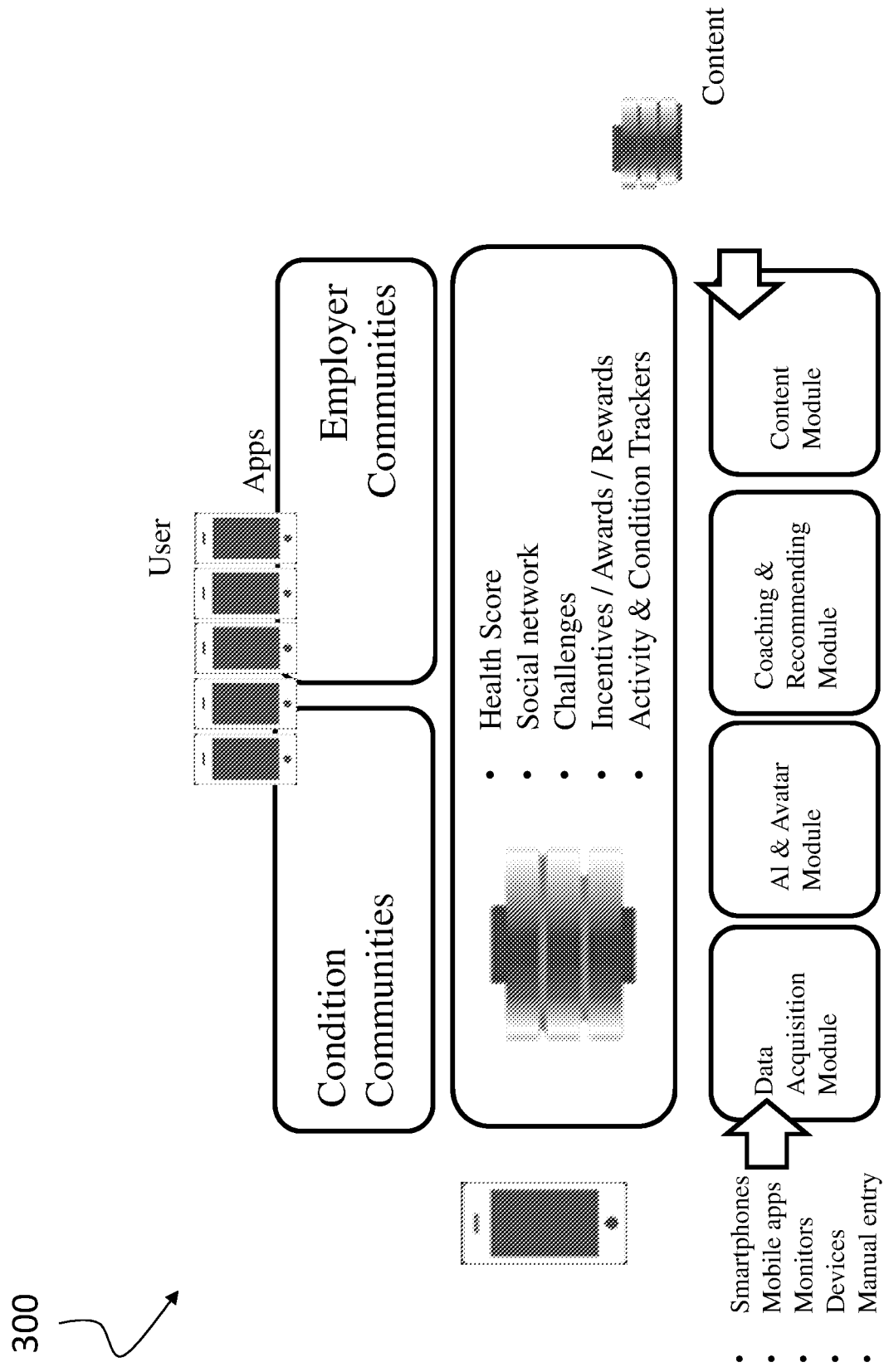
FIG. 3A is a block diagram that illustrates functional building blocks associated with an implementation of the present application.
Figure 3B:
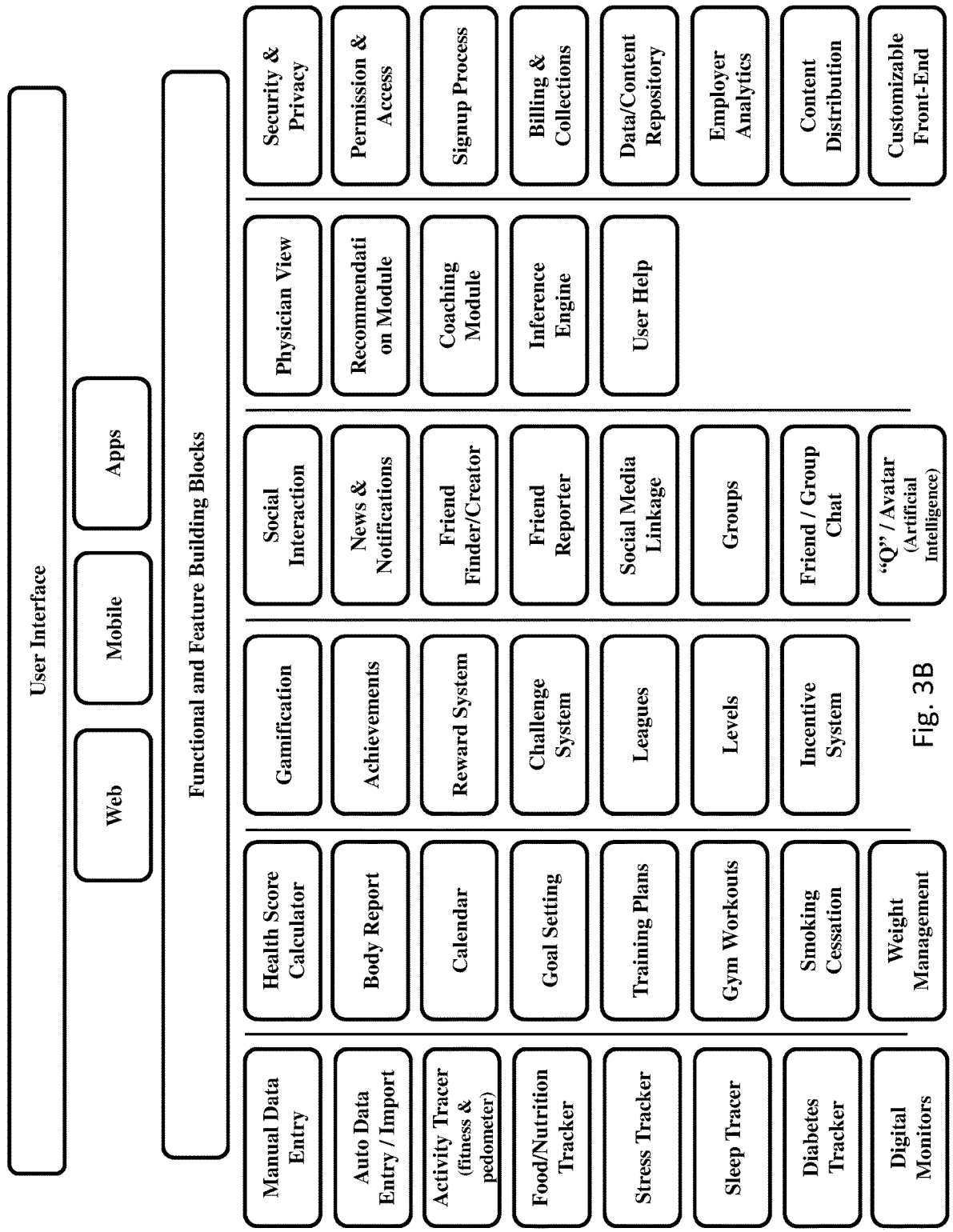
FIG. 3B is a schematic block diagram according to one or more embodiments of the present application.

FIG. 3A is a block diagram that illustrates functional building blocks 300 associated with a health platform, including for calculating a Health Score, as well as implementing many of the features shown and described herein. The health platform system in accordance with the present application can be accessed via Internet web browser software applications (e.g., CHROME, FIREFOX, SAFARI, INTERNET EXPLORER), and by using a desktop or laptop computer as well as from a mobile device, such as a Smartphone or Tablet via a mobile optimized version of the web site. An implementation is illustrated in FIG. 3B.

The system 100 can be configured with a smartphone software application, referred to herein generally, as the "tracker application," to track fitness activities in an easy and automatic way (in addition to providing for manual entry) and the recorded/tracked activities can be uploaded automatically on the health platform. The tracker application can be provided for devices operating IOS, Android and BlackBerry operating systems, and can be provided at no charge to the user.

Figure 4A:
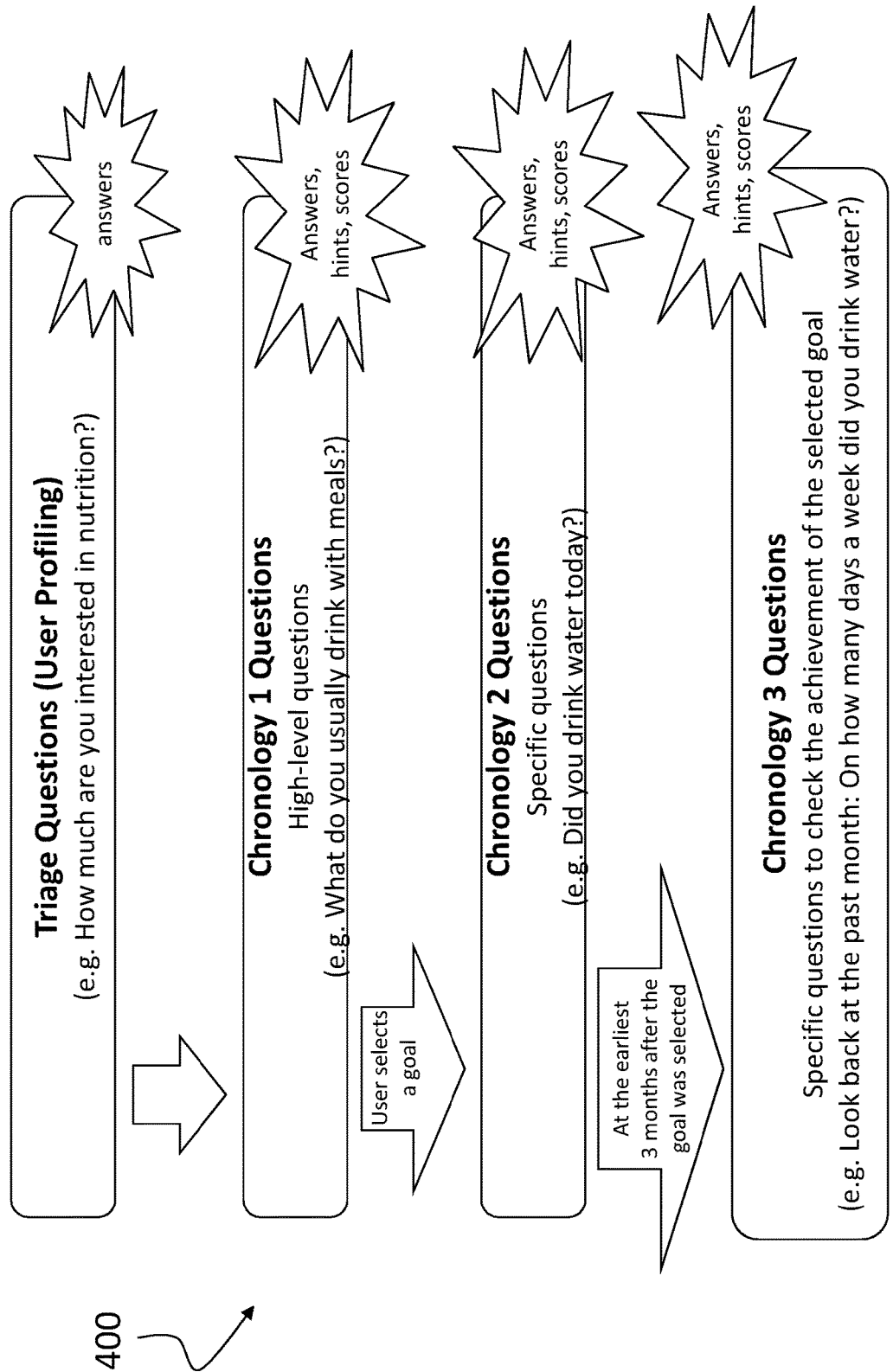
FIG. 4A illustrates an example flowchart of steps associated with nutrition tracking in accordance with an implementation of the present application.

An example flowchart illustrating example steps 400 associated with nutrition tracking is illustrated in FIG. 4A. Example steps include asking and receiving responses to questions associated with a user's interest in nutrition, goals and progress, and a plurality of chronology questions. For example, "triage" questions directed to user profiling can be provided, such as how much a user is interested in nutrition. Chronology-type questions can include high-level questions, such as asking what a user usually drinks with meals, as well as specific questions such as whether a user drank water today. A user can select a goal and at a specific time period, such as three months after a goal is selected, specific questions can be posed to the user to check the achievement of the selected goal. For example, after a month of time has passed, the user can be asked on how many days a week to the user drink water. In this way, server 180 and/or client 160 can be configured to provide nutrition tracking and effectively identify goals and accomplishments of the user.

Figure 4C:
Figure 4C:
Figure 4C:

FIGS. 4B and 4C, illustrate example screen displays 402 and 404 associated with manually entering data, e.g., via a graphical user interface via screen controls (e.g., buttons, icons, drop-down lists, radio buttons, checkboxes, textboxes or the like) and submitted by the user in response to a user interface provided on client 160 and/or server 180. As shown in FIGS. 4B and 4C, information, such as relating to indoor and outdoor activity can be inserted manually via a web form or other graphical user interface provided by server 180 and/or client 160 (FIG. 4B) or via a mobile platform (FIG. 4C) and users can also choose to upload images together the information associated with respective activity. For example, information relating to duration, distance, incline (e.g., ascent), heart rate, and energy can be manually submitted in a data entry display screen and processed by server 180 and/or client 160. Moreover, specific kinds of activities (e.g., swimming) can be provided via graphical user controls, such as drop-down lists, radio buttons, checkboxes, text boxes or the like.

Figure 4D:
FIG. 4D illustrates examples of automatic data entry/ import controls in accordance with an implementation of the present application.

Alternatively (or in addition), data entry can occur substantially automatically, such as via an import process of one or more files formatted in one of various file types (e.g., TXT, DOC, PNG, JPEG, GIF, GPX, and TCX). FIG. 4D illustrates an example data entry display screen 406 that is provided to a user for importing data associated with a particular activity via the tracker application. In the example display screen 406, workout data are uploaded via the tracker application.

Figure 5:
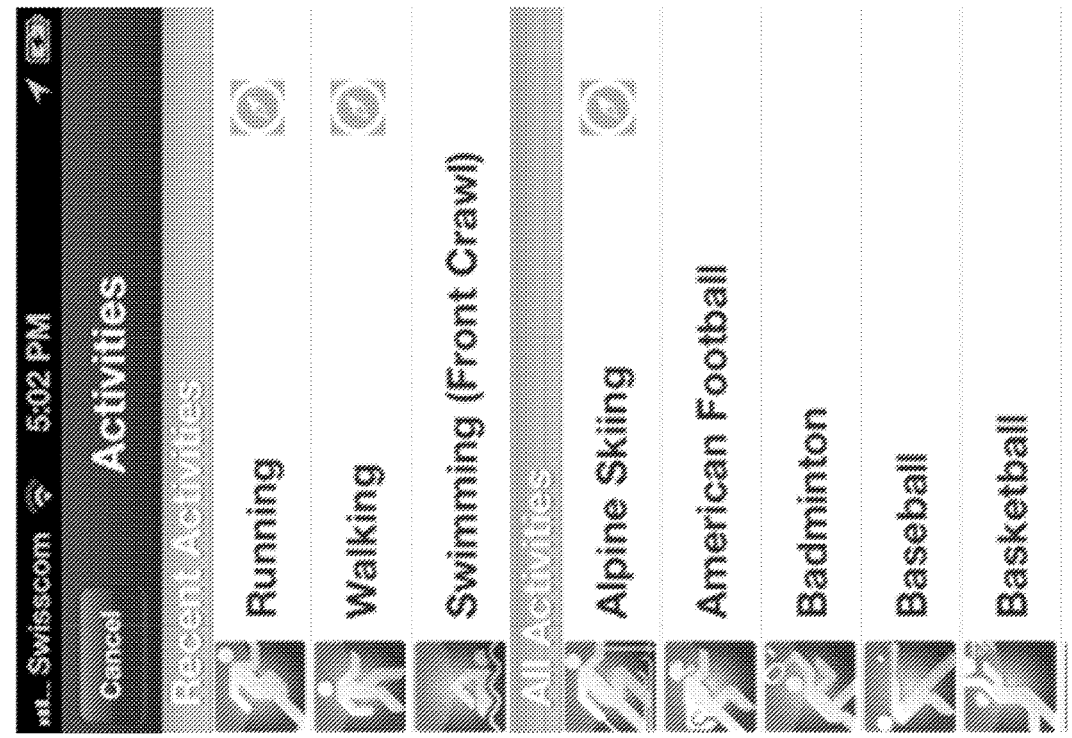
FIG. 5 illustrates a list of activities provided via a mobile computing device in connection with device integration accordance with an implementation of the present application.
Figure 5:
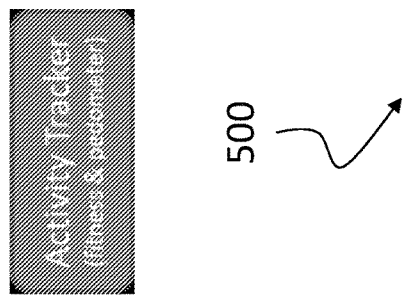

In one or more implementations, the present application offers the tracker application to track a user's fitness activity, and can be implemented on devices running IOS, ANDROID, WINDOWS PHONE, BLACKBERRY and other suitable mobile device operating systems. Outdoor and indoor activities can be tracked, and data upload to a server computer or other device can be provided in a secure format. The data can be seamlessly and automatically integrated for calculating a user's Health Score. For example, daily activity measured by stepcounters/pedometers or other similar devices can be integrated using the systems and methods shown and described herein. An example and non-exhaustive list of activities provided via the tracker application and usable to calculate a user's Health Score is illustrated in an example display screen 500 in FIG. 5.

In one or more implementations, a plurality of integration strategies are supported. For example, server-side integration can be employed to integrate devices. Alternatively, mobile integration can be supported, which integrates devices into the tracker application (or other suitable mobile application). Health data can be organized per user, and can be provided in connection with: body dimensions (height, waist circumference); body weight (including body fat); blood pressure (including pulse); blood sugar levels (fasting flood glucose); blood lipids (total, high-density, low-density, triglycerides); and workouts (duration, distance, ascent, descent, velocity, energy, trackpoints, heart rate, pictures).

Figure 6:
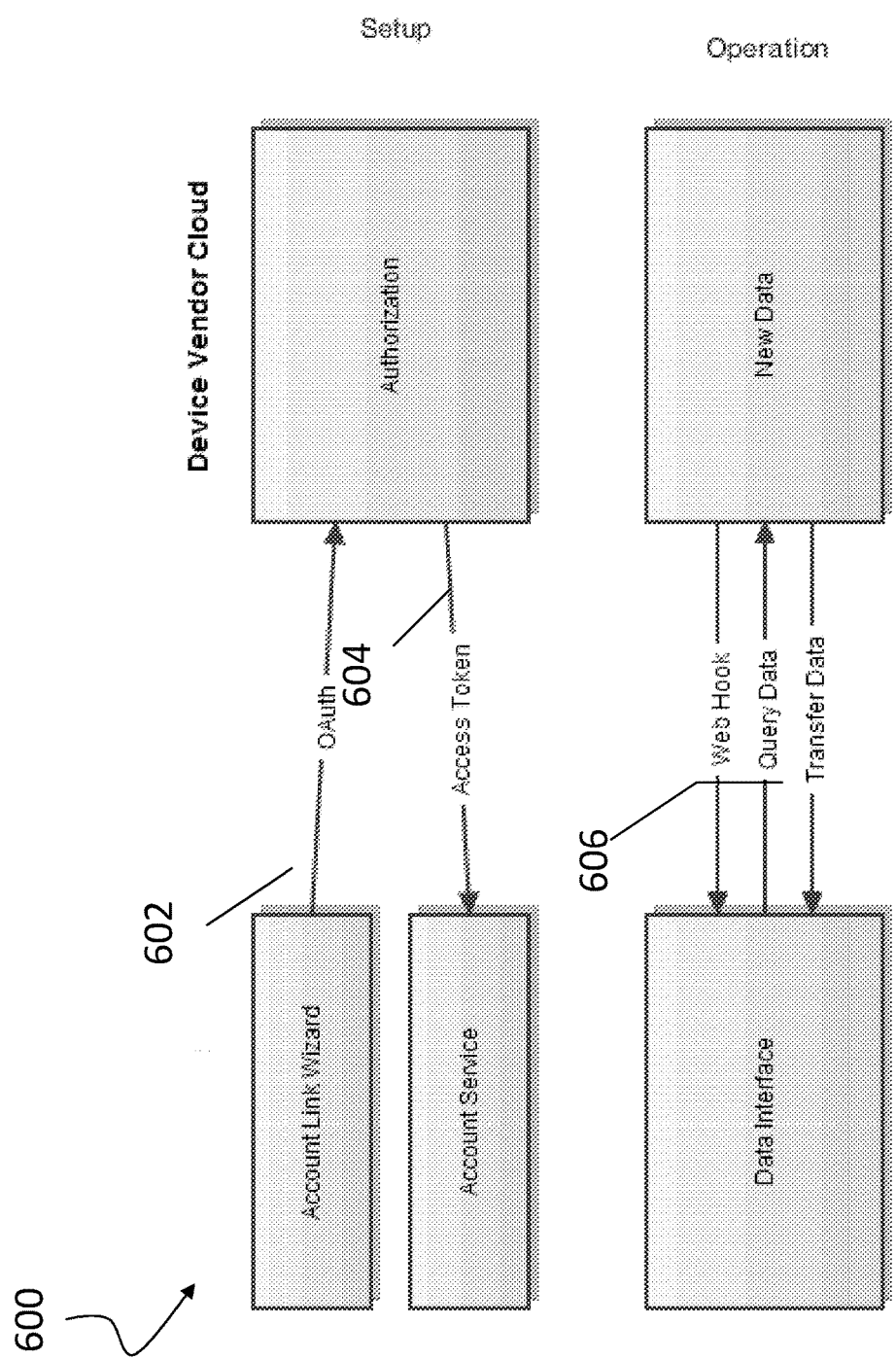
FIG. 6 illustrates steps associated with integrating a device in connection with server-side integration in accordance with one or more implementations of the present application.

FIG. 6 is a flowchart illustrating steps 600 for server-side integration of a device in accordance with one or more implementations of the present application. After a decision is made deciding in what journal to place the data, an account link wizard is implemented that allows users to connect their account(s) to a cloud account, which can be provided by a device vendor. This connection can be created using a suitable standard, such as OAuth (step 602). In case the cloud account contains data from multiple users in a home, a single user profile can be selected as part of the connection step. Further a data interface can be developed. Once an account link is established, the cloud can execute a web hook whenever new data becomes available. That data can be pulled from the cloud using security credentials, such as via an access token (step 604). In order to facilitate implementation of the above-identified steps, a generic account service can be provided that allows for managing links to external accounts on a per-user basis and in a safe and efficient way. Periodic account operations, such as subscription/web hook renewal, and one-time operations, such as asynchronous bulk data loading, can also be supported. Example technical features can include: HTTPS, RESTful (service model), OAuth (authorization), JSON or XML (data format) and Web Hook (new data notification) (step 606). This infrastructure enables prompt and efficient integration of new devices.

With regard to mobile device integration, sensors that can be attached to a mobile device can often be integrated by the user uploading sensor data, e.g., to a cloud device using a mobile phone app. A server or other computing device can receive sensor data from that cloud device via server-side integration, as described above. A direct integration of devices into the mobile app in accordance with the present application can be suitable in connection with partial information (e.g., heart rate to be correlated with a workout being tracked), data confidentiality (e.g., data directly sent and not passed through a cloud device), and ease of use (e.g., by reducing the number of user accounts needed for implementation of the presentation).

Integrating a device, such as a sensor, directly into the tracker application can include support for iOS, Android, BlackBerry, and/or Windows Phone operating systems. Other support, such as provided via library files, can include operation to check for the presence of the sensor; operation to read current sensor data; support for operation to pair with the sensor; callbacks on relevant events (new data, peak detected, etc.), capability of supporting multiple applications using a library concurrently, and capability of operating when the application is in the background.

In one or more implementations, a food/nutrition tracker module is proved that provides a single score (with sub-scores), as well as being scientifically founded, being applicable internationally, and includes quantitative and qualitative data (e.g., amount and type of food/beverage). In one or more implementations, the food/nutrition tracker module is easy to use (e.g., via "two clicks"), user-friendly, fun, attractive, sexy, and motivating instead of moralizing. In one or more implementations, the food/nutrition tracker module includes learning, such as by tracking how a user behaves, and is individualized to customize how the program responds. The focus of the food/nutrition tracker module is on a healthy diet and favorable eating behavior. Moreover, the food/nutrition tracker module can focus on sustained weight management rather than weight reduction. Thus the tracker is not merely a calorie counting application, but rather prompts the user towards healthier options at mealtimes. Moreover, and as noted above, information associated with the food/nutrition tracker module is integrated seamlessly and substantially automatically for calculation of the user's Health Score.

As noted herein, an individual's health depends on various interrelated factors. One important determinant of health is lifestyle. The physical, social and occupational environment of people largely defines the general framework for behavior, particularly when it comes to health. Notwithstanding the environment, a person's health substantially depends on the everyday choices made towards promoting health behavior and how to resist behavior that is hazardous.

The present application focuses on four domains that not only have a strong impact on health, but can also be improved. The domains include 1) physical activity, 2) stress, 3) sleep and 4) diet. The food/nutrition tracker module focuses on health improvement through healthy diet and nutrition.

It is recognized that energy and nutrients in food and drink, for example, directly impact risk factors e.g., blood lipids, as well as the risk of a heart attack, stroke, cancer and other non-communicable diseases. Similarly, an immoderation of calories can lead to weight gain. Excessive body fat can excrete hormones or modify or impair the effectiveness of hormones and increase risk factors, such as high blood pressure or unfavorable blood lipids. While food composition is important, so is energy balance. The way people eat is a result of culturally fixed patterns, which makes eating behavior resistant to change. It is, therefore, unlikely that following a simple program such as dieting or counting calories will lead to sustainable behavioral changes in the majority of cases. When, why and how a person eats need to be addressed in greater depth.

In order to be able to determine an individual's potential for improvement, specific behaviors need to be examined and, if necessary, adapted. Many adults have behavioral patterns that have been stable for years. For a change to become sustainable, selected improvements in nutrition and eating behavior have to fit to an individual's lifestyle and have to steadily become a part of it. The food/nutrition tracker module of the present application addresses this by prompting a suggesting a selection of potential improvements to the user that are customized to the user's own nutrition and eating behaviors.

In one or more implementations, the present application enables users to sustain positive lifestyle changes. The food/nutrition module of the tracker application can take into account various aspects, including sustainability with respect to body weight. The food/nutrition tracker module processes information to enable a user to sustain a healthy lifestyle, and avoid promoting quick fixes, for example, for weight loss. Users receive information to manage body weight in order to achieve a healthy body weight and avoid weight gain. For users who wish to lose weight, scoring can be adapted to focus on energy balance. Moreover, a weight management module can be provided that prompts for specific weight-related questions about diet and eating behavior, and that processes information received in response to the prompts to provide tailored and specific hints.

In one or more implementations, the present application enables users to improve and/or strengthen health resources. Such resources allow people to maintain their health status and to better cope with potentially hazardous influences, such as disease risk factors (as described herein).

In addition, a food and beverage intake component can be included in food/nutrition tracker module, and can be relate to the MEDITERRANEAN DIET (MD). Adherence to the MD is believed to result in an improvement of risk factors such as insulin resistance, high blood pressure and blood sugar or impaired blood lipids. Eating and drinking according to the MD is also associated with a reduction in morbidity and mortality of major chronic diseases, including cardiovascular disease, cancer, diabetes, Alzheimer's and Parkinson's disease.

It is recognized than an advantage of the MD is that it is easy to follow. The MD can be administered in all western cultures. In general, dishes are easy to prepare and ingredients are readily available and affordable. Furthermore, the MD penetrates restaurants and canteens more and more. Finally, the MD is tasteful, variable and appealing. Scientifically, the MD provides the basis for an ideal approach to healthy eating and drinking, and offers an excellent probability of users sustaining a desired and/or healthy body weight.

In one or more implementations, monitoring and maintaining positive eating habits are a substantial element of the food/nutrition tracker module. The food/nutrition tracker module can pose questions about a user's eating habits in order to detect problematic eating behavior, with focus on breakfast habits, meal circumstances (e.g., eating alone or in company) and duration, frequency and regularity of meals, snacking, as well as eating out, eating while doing other activities e.g., watching TV, cooking and preparation of meals, shopping for food and "emotional" eating. The latter occurs when people do not eat because they are hungry or have appetite but because of emotions such as stress, frustration, loneliness, lack of sleep or physical activity.

Thus, in one or more implementations the food/nutrition tracker module helps users to keep their weight on track, and supports those who want to lose weight. For example the food/nutrition tracker module can assist users with strict scoring, guiding the user towards a lower caloric intake. In one or more implementations, the food/nutrition tracker module stresses reasonable weight reduction and maintaining a lower body weight. The food/nutrition tracker module can target sustainable lifestyle changes by using more specific questions and tailored, practical prompts.

In one or more implementations, the food/nutrition tracker module of the present application can be implemented in conjunction with a rules engine ensuring that feedback can be modified in mostly declarative ways, requiring little programming. In addition, various communication channels, such as a web channel, an e-mail channel and mobile app channels are supported. Moreover, user profiling can be provided, and one or more questions are provided, such as regarding the user's dietary avoidances, interest in nutrition and occupational status. The food/nutrition tracker module of the present application covers the following domains (qualitative and quantitative): 1) food intake, 2) beverage intake and 3) eating habits. These three domains can be further subdivided into sub-domains.

The food/nutrition tracker module of the present application precludes repetitive prompts to avoid boring and/or jeopardizing the user's interest. For example, the food/nutrition tracker module starts off in a high-level way, such as by asking the user questions about his/her typical consumption behavior, such as "Do you drink water with your meals?" Based on the answers received from the user, the food/nutrition tracker module may provide increasingly specific questions about the user's consumption and behavior, such as, "Did you drink water today?"

The food/nutrition tracker module of the present application can also include different types of questions, such as yes/no questions, selection questions (single choice, multiple choice) and value entry questions. In an implementation in connection with a mobile computing device, a user interface can be optimized for touch operation, e.g., using large check boxes, large selection buttons, and sliders for range-based input. The labeling of sliders is generally based on the local unit system of the user, whereas the valuation rules can be based on internationally recognized (e.g., International System (SI)) units. The user interface ensures the proper translations and representation of values. The user's answers allow the food/nutrition tracker module of the present application to monitor the progress of the user in achieving self-set goals.

The food/nutrition tracker module of the present application can alternate questions randomly, between domains and sub-domains and not in a fixed order. Furthermore, the food/nutrition tracker module of the present application also prompts questions depending on particular context (e.g., depending on the time of the day), thereby reducing lag time between an event and its recording. Some questions can be asked on specific days, e.g., on Sundays. Further, questions that the user does not answer can be asked again after three to four days, and can be repeated again if the user still does not answer. In an implementation, if the user does not answer 10 consecutive questions, the food/nutrition tracker module of the present application can prompt the user to resume.

It is recognized that goals for dietary achievement should be realistic, particular from the individual point of view of the user. If too many goals are imposed that are unachievable or unstructured, the user will become frustrating and confused and thus become counterproductive. The food/nutrition tracker module of the present application avoids this by proceeding methodically, first getting to know the habits of the user and then detecting areas with potential for improvement. Based on the information obtained from the user, the program defines realistic goals, which are suggested to the user and ordered by priority. The program can then ask the user which of the three goals he/she wishes to achieve first. The food/nutrition tracker module of the present application can follow a step-by-step approach, meaning that goals need to be worked on by the user (from fully achieved to not achieved or postponed) before new goals can be suggested. Thus, the user works on only one goal at a time. Once a week, for example, the user decides if he/she wants to continue working on the goal, work on another goal or take a break from working on goals.

In an effort to keep a user motivated, rewards may be provided when goals are achieved. Besides virtual rewards, such as medals, cups or titles, competitive elements can be used by server 180 and/or client 160 to increase positive feedback by the food/nutrition tracker module of the present application. Further rewards can include special treats (e.g., free entry to the gym for a month).

In one or more implementations, responses to prompts can trigger one or more specific hints. Hints are aimed at leading the user towards achieving a goal, either supporting the user to make healthier choices in the future or praising the user for his/her healthy behavior. Hints provide not only concrete instructions, but also the rationale behind them. This increases user motivation and adherence to the program. Some responses can be followed questions immediately, before a hint is given. In one or more implementations, hints are provided by an avatar. Referred to and shown herein, generally, as "Q," the avatar can communicate in the first person singular form (e.g., "May I make a suggestion?"), which aims to create a personal relationship between the user and the food/nutrition tracker module of the present application.

In response to prompts from the food/nutrition tracker module, a score can be attributed that can include three dimensions: 1) favorable behavior, 2) indifferent behavior, and 3) unfavorable behavior. A corresponding score can then be factored with one or more other nutrition-related scores, and applied in the calculation of a user's overall Health Score. For example, a nutrition-related score can be calculated with a sports-related tracking score originating from physical activity, a stress score, a sleep score or the like. Moreover, in one or more implementations, the present application supports transparency in that the user has access to his/her scores at any time.

In one or more implementations, the tracker application captures stress-based information, based on the data acquired, for example, via sensors on smartphones and questionnaires. In one or more implementations, heart rate variability (HRV) can be monitored with an integrated external heart rate band. Alternatively, sensors may be implanted in a body, such as a pacemaker or other technology that can be operable to transmit information to a computing device. In one or more implementations, the sensors that are provided in accordance with the present patent application can be non-invasive or invasive. For example, the sensor(s) can detect heartbeats and can provide for transmitting data from an implanted pacemaker. Alternatively, blood sensors that are mounted in a person's body transmit data, for example, to detect one or more marker proteins that may be present in the wearer's blood. Thus, the present application can be usable with one or more sensors that are placed in or with the wearer's body, and/or are otherwise configured to communicate with devices that are implanted in a person.

In addition, the device can be configured to detect and/or display humidity associated with user's skin surface. Humidity information is usable, for example, to detect that the user is or is getting dehydrated and should drink. In one or more other implementations, DNA information and/or one or more biomarkers is accessible, for example, to examine biological processes, pathogenic processes, or pharmacologic responses, such as associated with one or more therapies.

In one or more implementations, the stress tracker allows the user to enable/disable stress tracking, with controls for recording of voice, social, and movement stress. The user's current stress score can be displayed, and can allow a user to start an overnight HRV measurement session. Moreover, the stress tracker can show the result of the overnight HRV measurement session, and asynchronous/interactions with the avatar ("Q") can be shown. For example, the avatar "Q" can ask the user for a voice sampling. Moreover, the avatar "Q" can ask the user to answer one or more specific question sets. The avatar "Q" can further recommend to the user to do an overnight HRV measurement session. In addition, information obtained thereby can be seamlessly and substantially automatically integrated into the user's Health Score. In addition, sleep tracking can be provided in a mobile application implementation of the present application. For example, a seamless integration of Heart Rate Variability and diagnostics of sleeping patterns.

In one or implementations, a plurality of monitoring devices can be employed that use various operating systems and/or platforms. One or more application programming interfaces ("API's") can be provided to support integration and communication among and between various kinds and brands of devices.

Figure 7:
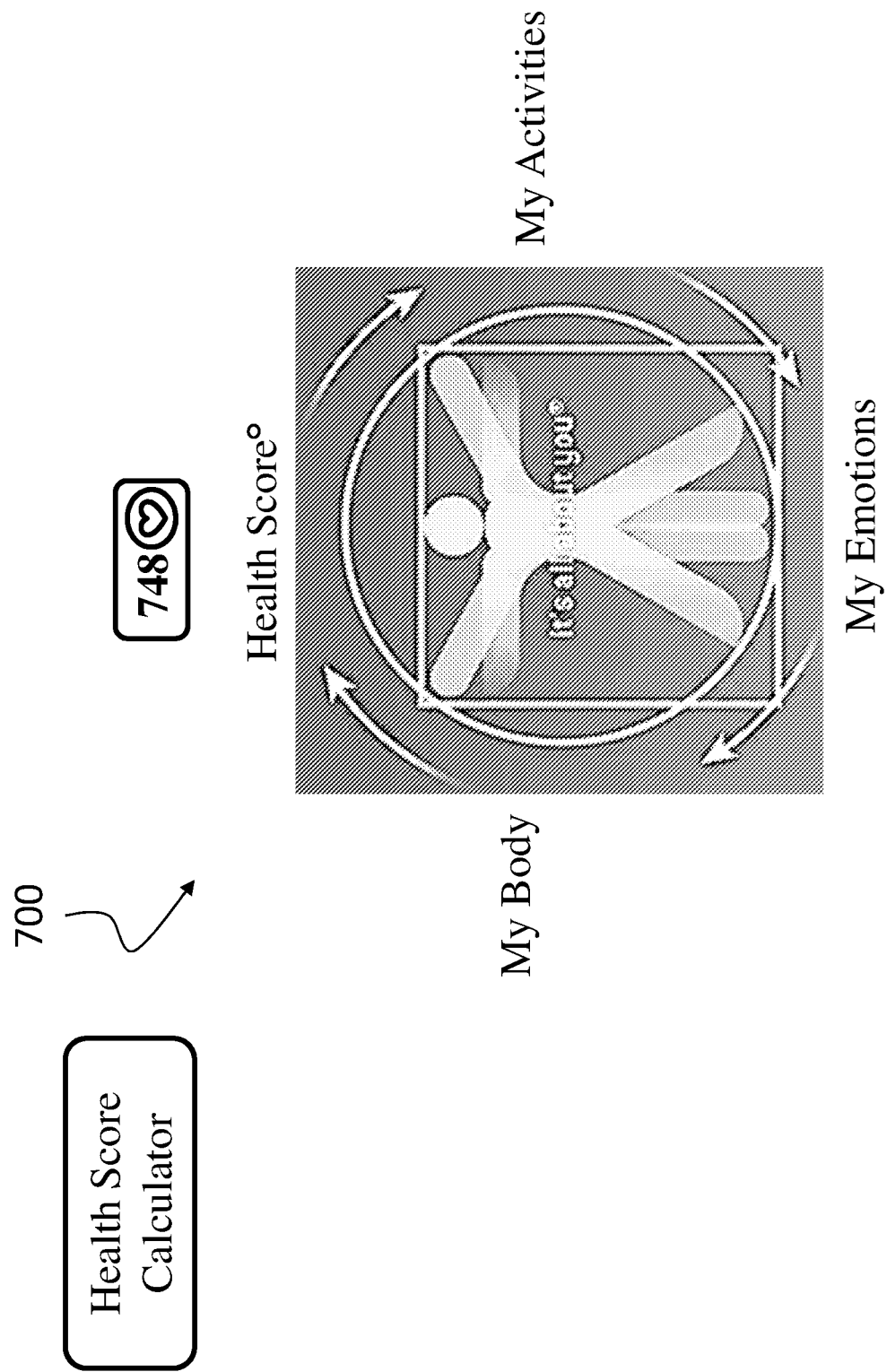
FIG. 7 illustrates the interrelationship between variables associated with a person in the calculation of a Health Score, in accordance with an implementation of the present application.

With reference now to FIG. 7, the present application can calculate a personal Health Score for each of a plurality of persons, which can be represented by a number from 1 (representing a poor score) to 1,000 (representing an excellent score), and which can represent current health and fitness status information substantially in real-time. When tracked over time, the Health Score offers a directional relative indicator of how a user's health and fitness is improving or deteriorating. In this way, the Health Score provides output substantially in real-time and provides a virtual "mirror" of the user's overall health and fitness. This provides an avenue for the user to maintain health & fitness awareness level high. Furthermore, with the introduction of a score, a user can benchmark himself or herself against others, all the time. As indicated in the example display screen 700, a user's health in connection with the user's body, activities and emotions are factored in a symbiotic way to identify and calculate the health score.

The Health Score of the present application can be analogized as Celsius/Fahrenheit to measure temperature. Rather than describing temperature in terms of 'cold' or 'warm,' for instance, temperature can be precisely and numerically represented. Similarly, the Health Score of the present application is useful to precisely and/or numerically represent a person's health. Moreover, in one or more implementations, a "what if" scenario can be provided for users to enter one or more variables to determine how various behaviors can affect a user's Health Score (e.g., quit smoking, losing weight, etc.). Moreover, in one or more implementations, the Health Score of the present application factors three values representing the following categories of information received from a user: who the user is, which can include description of the user; how the user feels (such as emotions, quality of life, etc.); and what the user does (such as activities, lifestyle components, etc.). The Health Score in accordance with the present application can represent a "living score," one that is dynamic and learning over time. With the introduction of new information from the user, and new medical breakthroughs and developments, the algorithm can be optimized over time.

Figure 8:
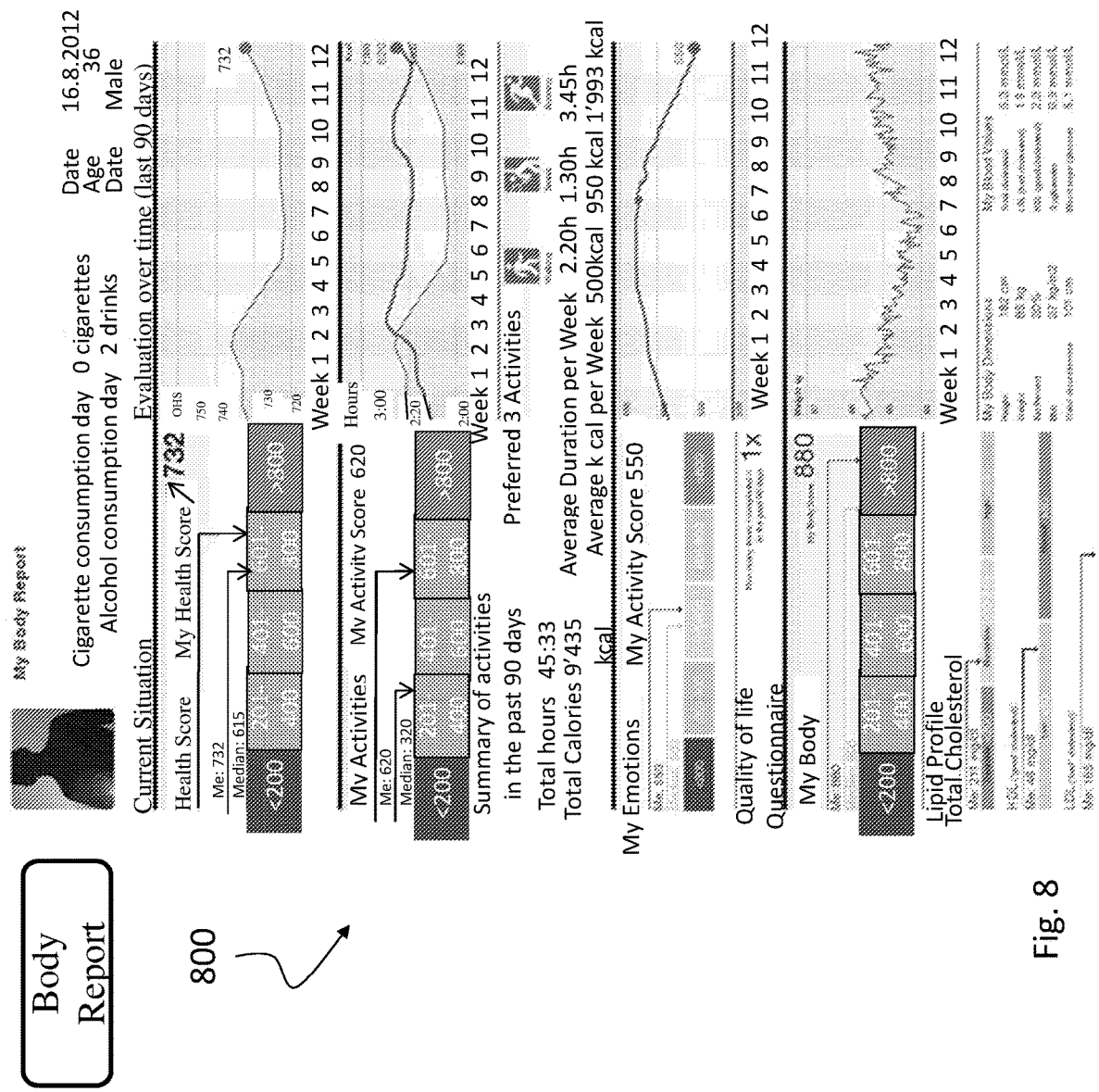
FIG. 8 illustrates an example "body report" divided in accordance with an implementation of the present application.

FIG. 8 illustrates an example body report 800, divided in accordance with an implementation of the present application. In the example shown in FIG. 8, the body report 800 is formatted as a 1-page report that includes the key data on the user with regard to his/her Health Score, as well as sub components both currently and over time. The report can be useful for personal use, or be shared with a personal trainer or a health professional, for example, in case the user chooses to share it.

In the example shown in FIG. 8, a 36-year-old male reports smoking 0 cigarettes and consuming 2 alcoholic drinks per day. The user's Health Score indicates improvement, shown by an arrow rising next to the user's Health Score of 732. In addition, the example body report shows the user's Health Score graphically presented over a 12-week period. The example body report shown in FIG. 8 also includes the user's activity numerical score, which is also graphically represented over a 12-week period. Additionally comparative data can be provided both in terms of actual number values (e.g., the user score versus median scores), as well as graphically, including a plurality of colored rectangular portions representing ranges of score values, and where the user lies therein. Other information represented in the body report includes values associated with the user's emotions, and an overall body score, which can be similarly represented numerically and graphically.

Figure 9:
FIG. 9 illustrates an example calendar view for users to review their fitness activities and receive feedback in accordance with an implementation of the present application.

FIG. 9 illustrates an example display screen 900 that provides a calendar view for users to review their fitness activities and receive feedback data on weekly/monthly hours trained and calories burned by activity and as a total. In the example shown in FIG. 9, a calendar view can be provided that allows users to visualize training plans, challenges, and activities, and to export calendar data to one or more email client applications, such as MS-OUTLOOK.

Figure 10A:
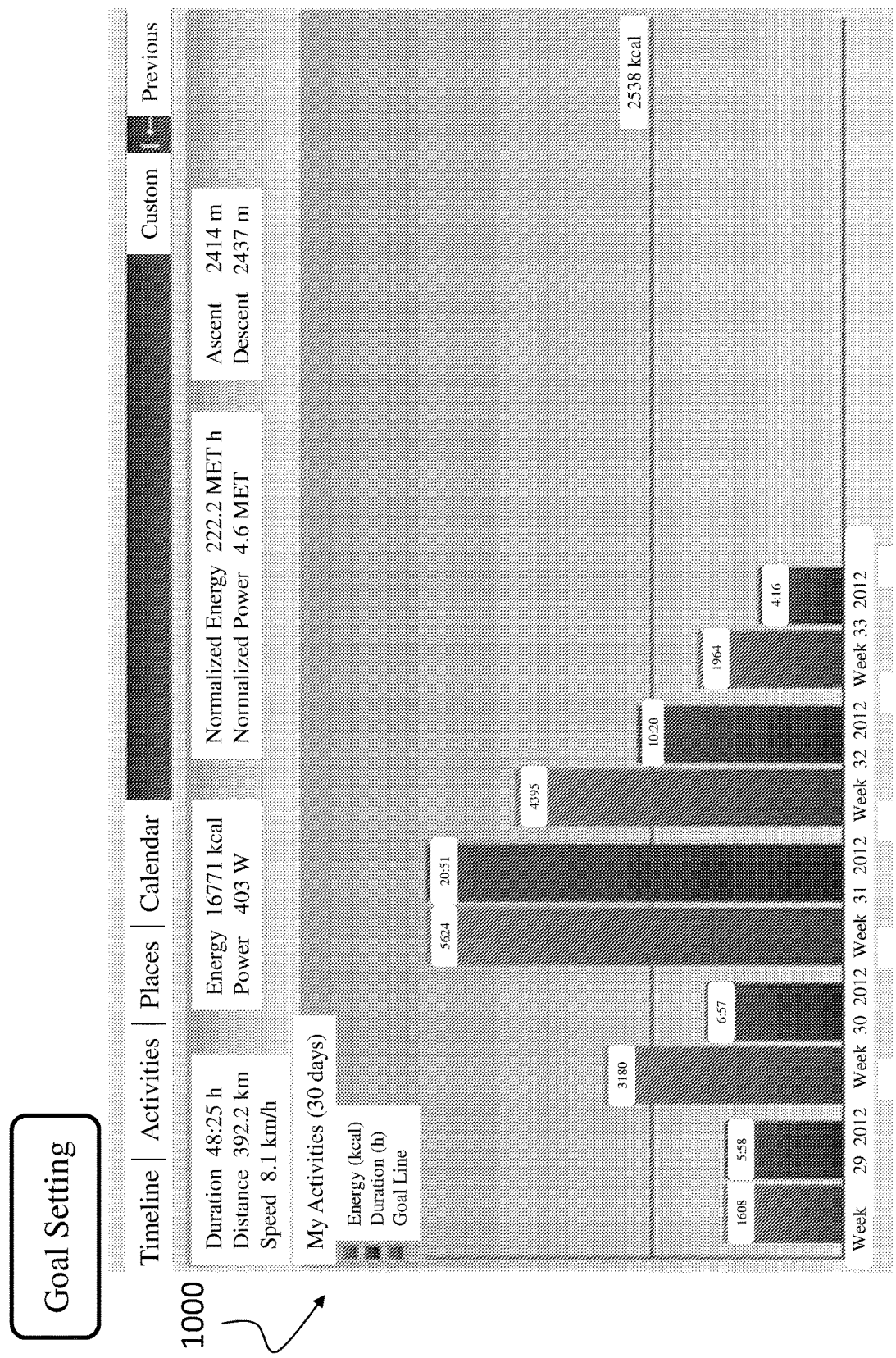
FIG. 10A illustrates a graphical indication of a user's goal activities, including in terms of energy and duration in accordance with an implementation of the present application.

With reference now to FIG. 10A, a display screen 1000 can be provided that includes a graphical indication of a user's activity goals, both in terms of energy and duration. Moreover, a goal line can be provided in display screen 1000, which provides the user with an amount of calories he/she needs to burn per time period to maintain the user's current Health Score. In connection with certain features associated with goals, goals can be set by both users and health professionals, and can span a wide range from simple goals over training plans to specific programs. In one or more implementations, a goals catalog can be included for a user to select one or more goals. Examples include: workouts (Burn n energy per week for t period target date, log n activities per period, run a marathon by t date, etc.); Health Score (reach a score of "n" by target date, etc.). Other examples include: training plan; achievements (complete achievement a by target date, etc.); smoking cessation program; and weight management.

Figure 10B:
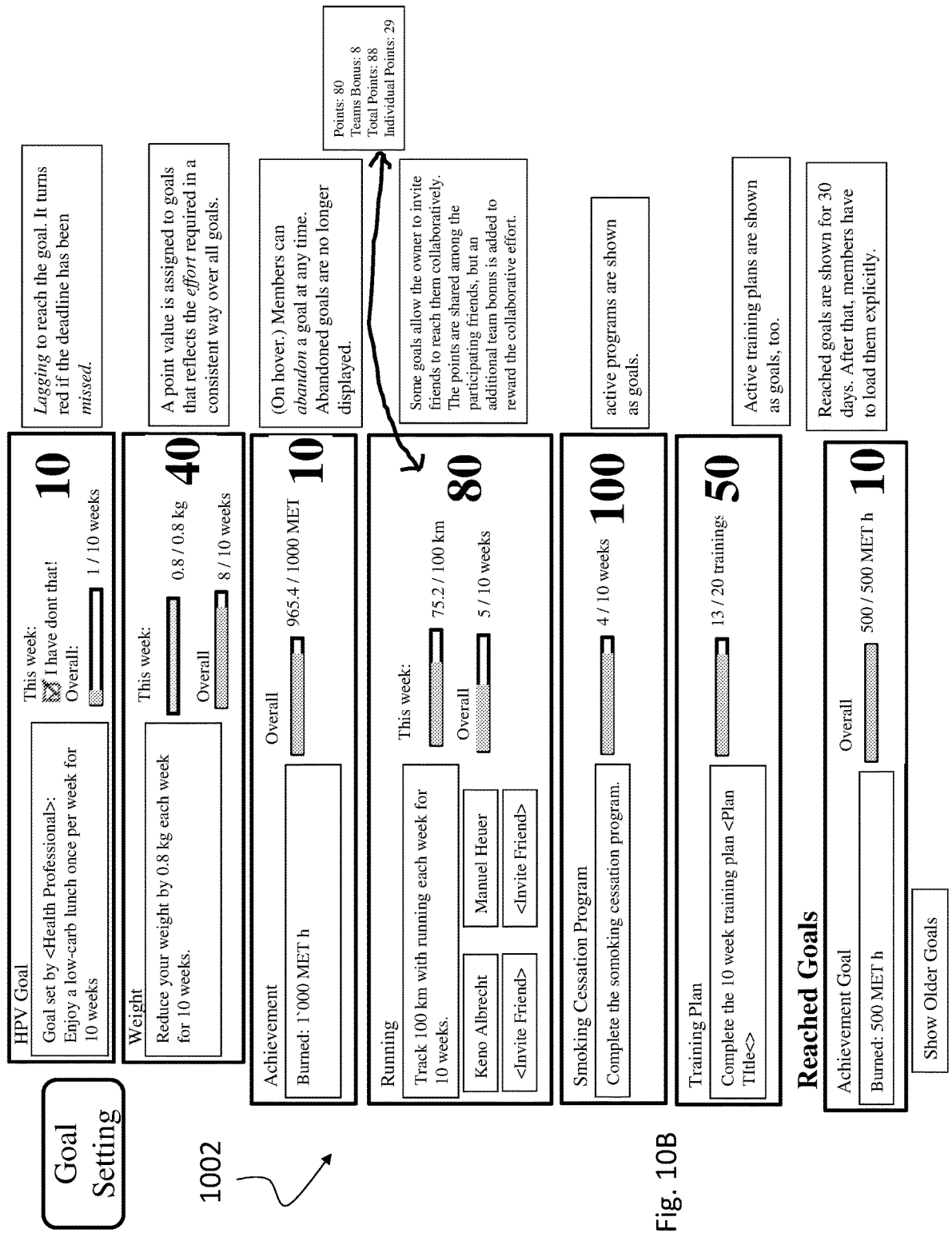
FIG. 10B illustrates an example display screen associated with current goals and reached goals for an individual.

FIG. 10B illustrates an example goals page display screen 1002 associated with current goals and reached goals for a user. The goals page display screen 1002 in FIG. 10B shows current goals of a user, and as shown in the example in FIG. 10B, each goal can be listed with a visually strong percentage bar, showcasing the progress made towards reaching the goal. For each goal, an indication can be provided whether, based on the current progress, the user is leading or lagging with regard to the target date. As noted herein, goals can be set both by users and health professionals, including via a user interface for health professionals. Goals can span a wide range from simple goals over training plans to specific programs, and goals can have respective target dates. The present application guides users from the Health Score drivers (e.g., via Health Score Refactoring) to specific goals, such as via particular programs.

A goals catalog can be defined for a user. For example, a goals catalog can include one or more of the following features. Workouts: Burn n energy per week for t weeks/months by target date; track n of metric m per week with activity a for t weeks (e.g., 25 km of running) log n activities per week for t weeks. Health Score: reach a Health Score of n by target date; reach a health reservoir score of n by target date; maintain a health reservoir score above 1 for t weeks. Journals: reduce metric m by d every week for t weeks (e.g., weight); reduce metric m to n by target date (e.g., blood sugar or lipids). Training Plan. Achievements: complete achievement a by target date. Smoking Cessation Program: information; questionnaires; notifications. Mediterranean Diet Program: information; and daily recipe notifications.

Figure 10C:
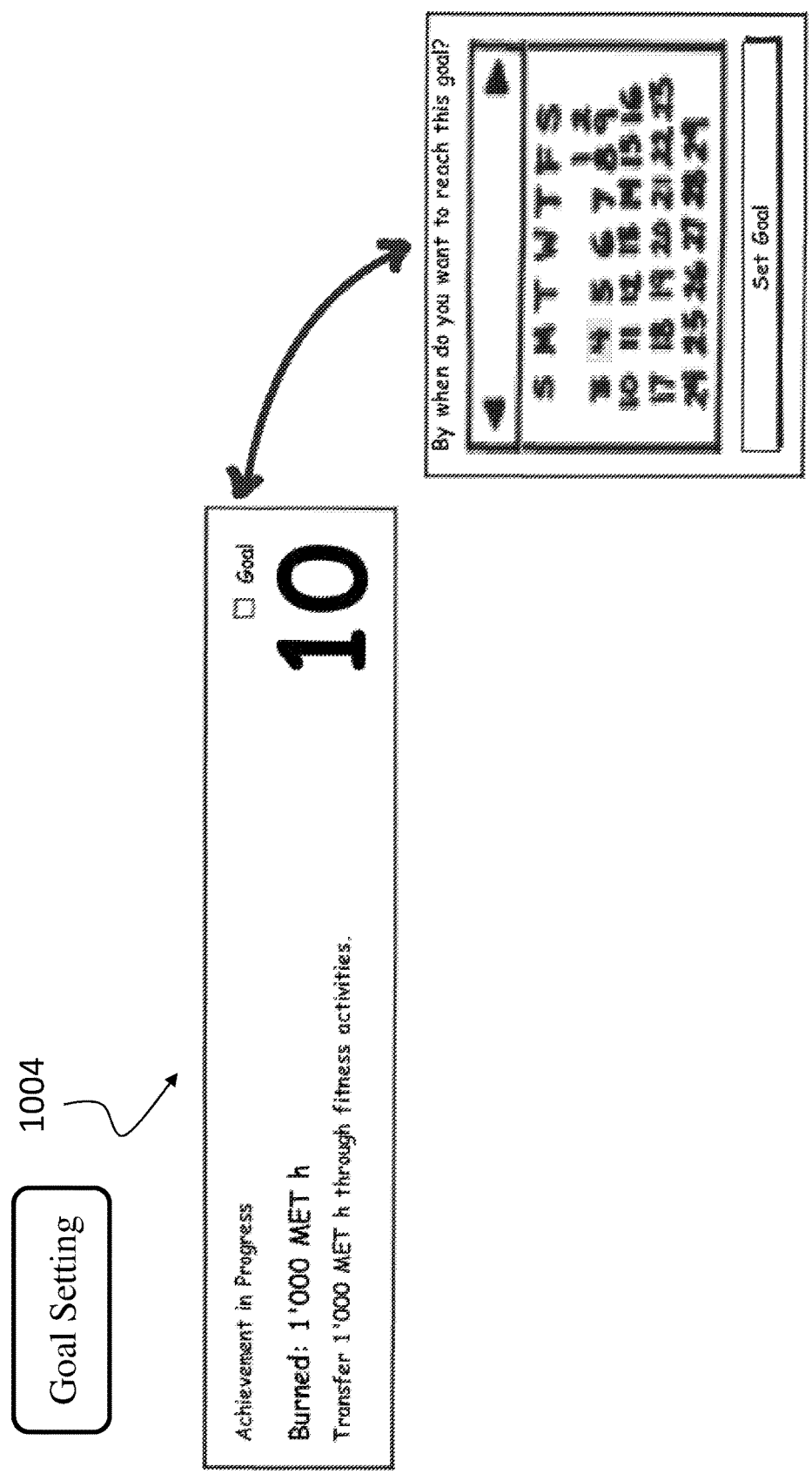
FIG. 10C illustrates an example interface for defining and achieving goals, in accordance with the present application.

Goals can be defined, such as by user and/or healthcare professionals at various points or places in connection with the present application. An example goal definition interface 1004 is illustrated in FIG. 10C.

Figure 10D:
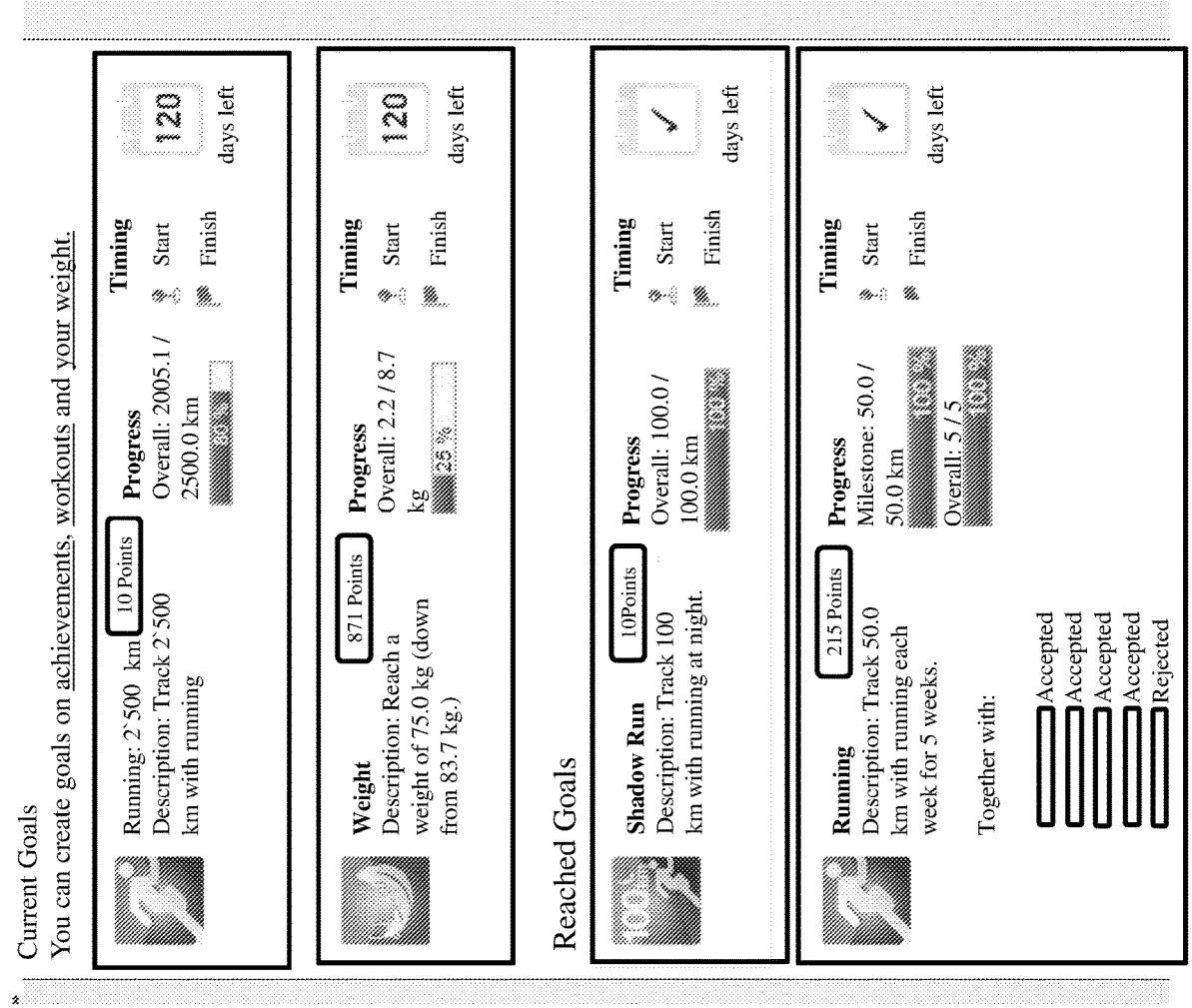
FIG. 10D illustrates an example display screen enabling creation of goals as a function of achievements, workouts and weight.

FIG. 10D illustrates an example display screen 1006 enabling creation of goals as a function of achievements, workouts and weight.

The present application also supports the development and monitoring of training plans that can include providing entries specifying detailed workouts. Workouts can include time, duration, energy, mood, as well as the warm-up, cardio, core, resistance and cool-down phase, and information of each of which can be captured. Various activities can include cardio exercises on fitness machines, as well as other types of activity, such as running, cycling, fitness classes, and review session(s) with a personal trainer. In connection with a workout, users can note changes to sets and repetitions given in the plan on their mobile devices. In addition, the mood for the workout can be logged. Training plans can be edited by drag and drop and copying entries from one weekday to another, and copying entire weeks to another week. Users can be able to print individual training plan entries as well, such as for taking to the gym.

Moreover, one or more gymnasium workout models can be provided for popular gym classes, such as Zumba, Body Toning, or Body Pump. In one or more implementations, automated integration of user's gym classes can be supported, for example, and can include a heart rate tracking algorithm. For example, nano based/plaster sensors can be integrated with the teachings herein.

In one or more implementations, the present application employs gamification, which refers, generally, to the use of game design techniques, game thinking and game mechanics in non-game contexts. Gamification can be used to make technology more engaging, by encouraging users to engage in desired behaviors, by showing a path to mastery, by helping to solve problems, and by taking advantage of a person's psychological predisposition to engage in gaming. Applying these principles in a health & lifestyle context makes for a powerful end user experience. By employing gamification, behavior can change, which represents a huge opportunity to improve health outcomes. Moreover, the combination of mobile technologies with social networking and gamification principles has the power to facilitate healthy lifestyle behavior change in individuals. Accordingly, the present application can apply gamification principles in various ways across the platform to engage users and encourage them to adopt a healthier lifestyle, which includes but is not limited to: Achievements; Rewards; Challenges; Leagues and Levels.

Figure 11A:
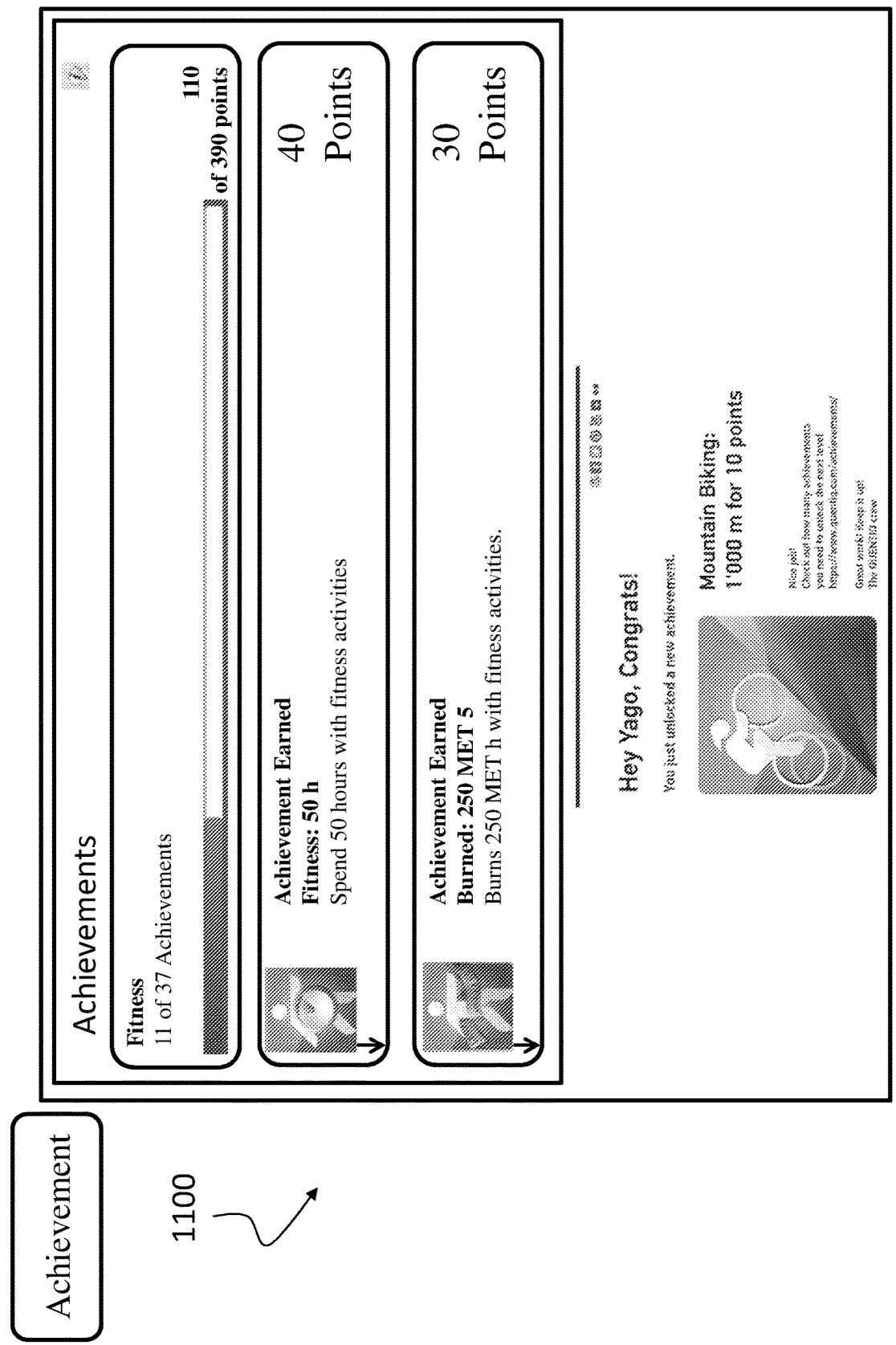
FIGS. 11A and 11B illustrate example screen displays associated with achievements and the progress of users.
Figure 11B:
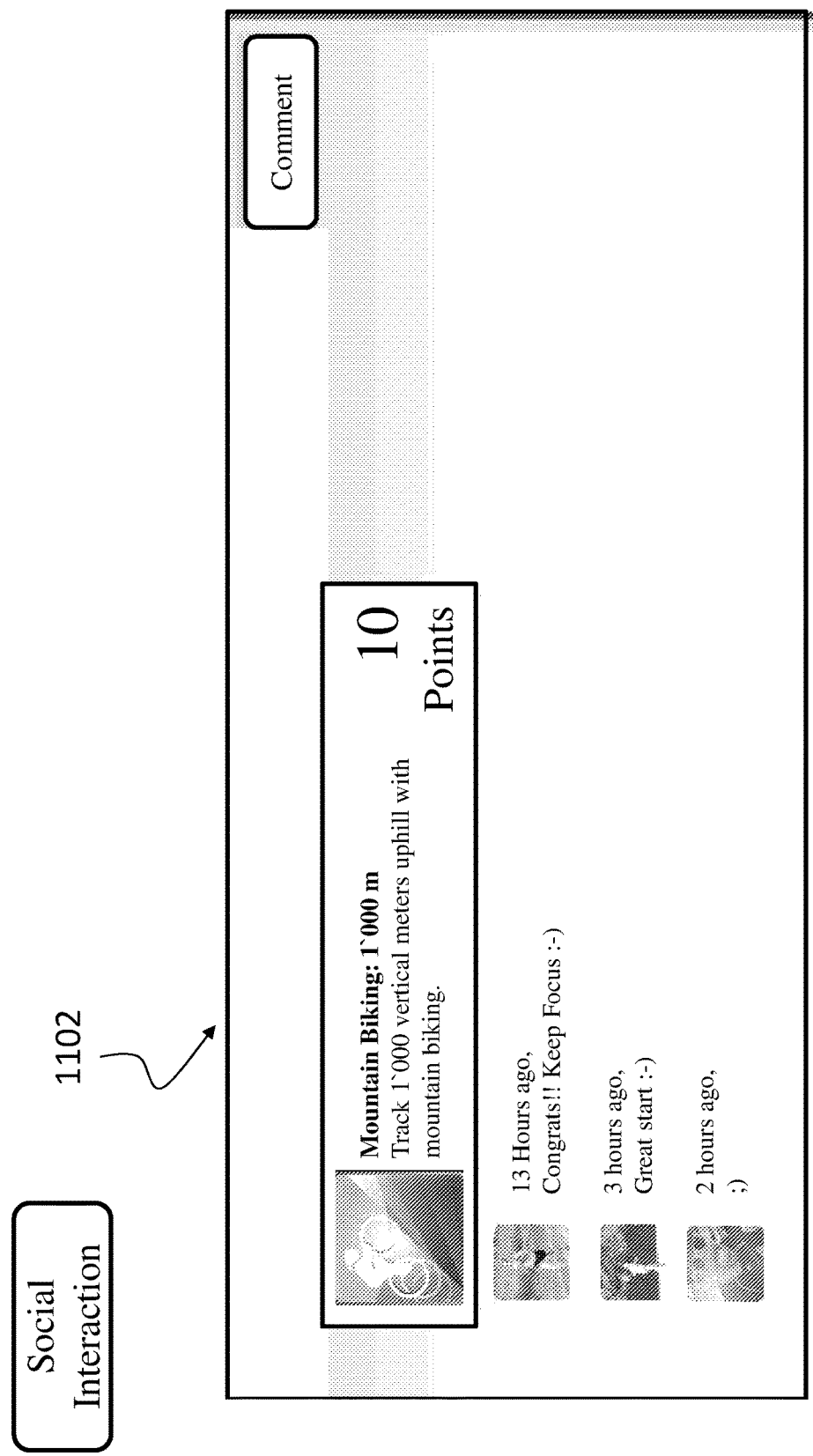

FIG. 11A illustrates an example display screen 1100 that can be provided via server 180 and/or client 160 and is associated with recognizing achievement and providing awards for user progress. By providing achievements and reward tracking in specific activities, the present application provides "pat on the back" feedback, which encourages users, such as by saying "congratulations" or "well done!" Messages can be provided graphically (e.g., trophies and awards), or with language. In one or more implementations, achievement messages can appear in a newsfeed, such as on a user's social network home page, which be shared via social media such as Facebook and Twitter. In connection with social networking, the present application includes interaction/interface with a user's newsfeed, commenting (such as on news items, achievements, activities), forums/discussions, picture sharing, video sharing, platform notifications, and push notifications. FIG. 11B illustrates an example display screen 1102 that demonstrates social interaction, which can be implemented by providing a medium for users to comment on each other's activities, including by supporting user sharing of multiple photos and activity events.

In connection with achievements earned, the present application provides "gamification" points, which can be awarded for motivation and reward purposes. In one or more implementations, achievement points are not factored into a user's Health Score. For certain achievements additional rewards can be earned that include, for example: a title that can be displayed on a user's profile; a pin that can be displayed next to a user's profile, or a special "wallpaper" that can be downloaded and used on a user's desktop or smartphone.

Figure 12:
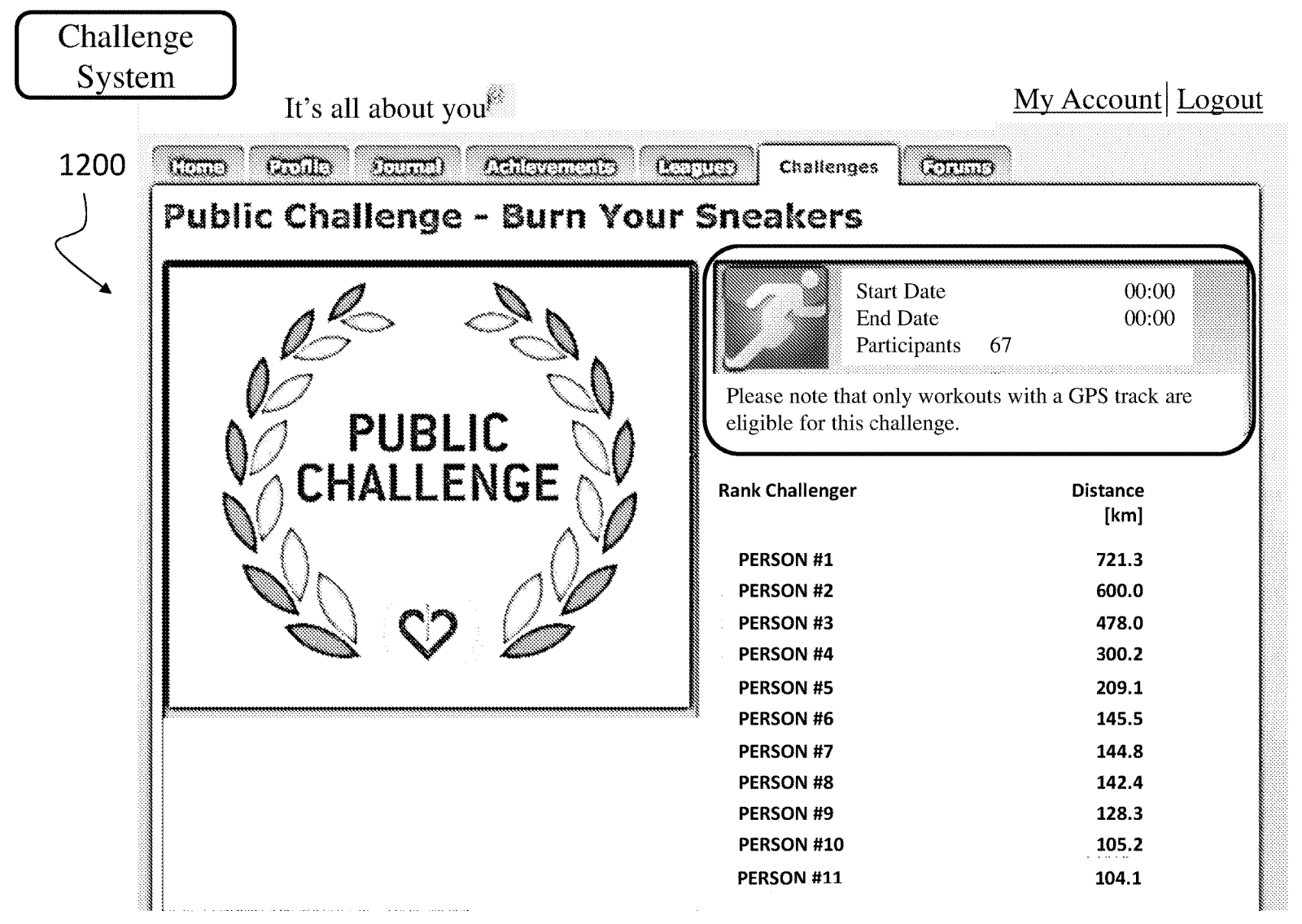

In one or more implementations, challenges can be supported that provide a direct way for users to compete with other users on a system 100 in accordance with one or more implementations. A challenge system can provided for various people or groups, such as individuals, groups, corporations, fitness clubs and public use. Individuals can use the challenge system to compete with their immediate friends. Groups can use the system to issue group wide challenges to their users and public challenges and/or a corporate customer and all platform users have the opportunity to compete in their challenge of choice. Further, team challenges can be supported that allow for teams to compete against each other (e.g., marketing versus sales department or a given client company). Group challenges and departmental specific challenges within corporations can be useful to create motivational activity. An example public challenge display screen 1200 is shown in FIG. 12.

Further, leagues can be supported that can engage users in more direct competition than achievements, but can represent less direct competition than challenges. In connection with leagues in one or more implementations, a user completes three workouts in a specific fitness activity to qualify for a league. Leagues can be broken down by type (Bronze, Silver, Gold and Platinum), activity type and division. In one or more implementations, leagues can run over seasons that last weeks to several months. Achievements and rewards can be linked to the league system, and league promotions can be shown in a user's social network newsfeed. Achievements for promotion to a higher league, can be earned, including for finishing a league season in top ranked positions.

The present application provides support for levels, incentives, and social interaction. Progression dynamics in form of Level-Systems can be integrated in the system 100, substantially as shown and described herein. Various features can include a seniority level based system. For example, a new user starts at Level 1 and gradually progresses and rises in levels along the way. Levels can be determined by the number and kinds of activity points that a user has earned. Activity points can be rewarded for tracking workouts, earning achievements, and commenting on news items.

Figure 13:
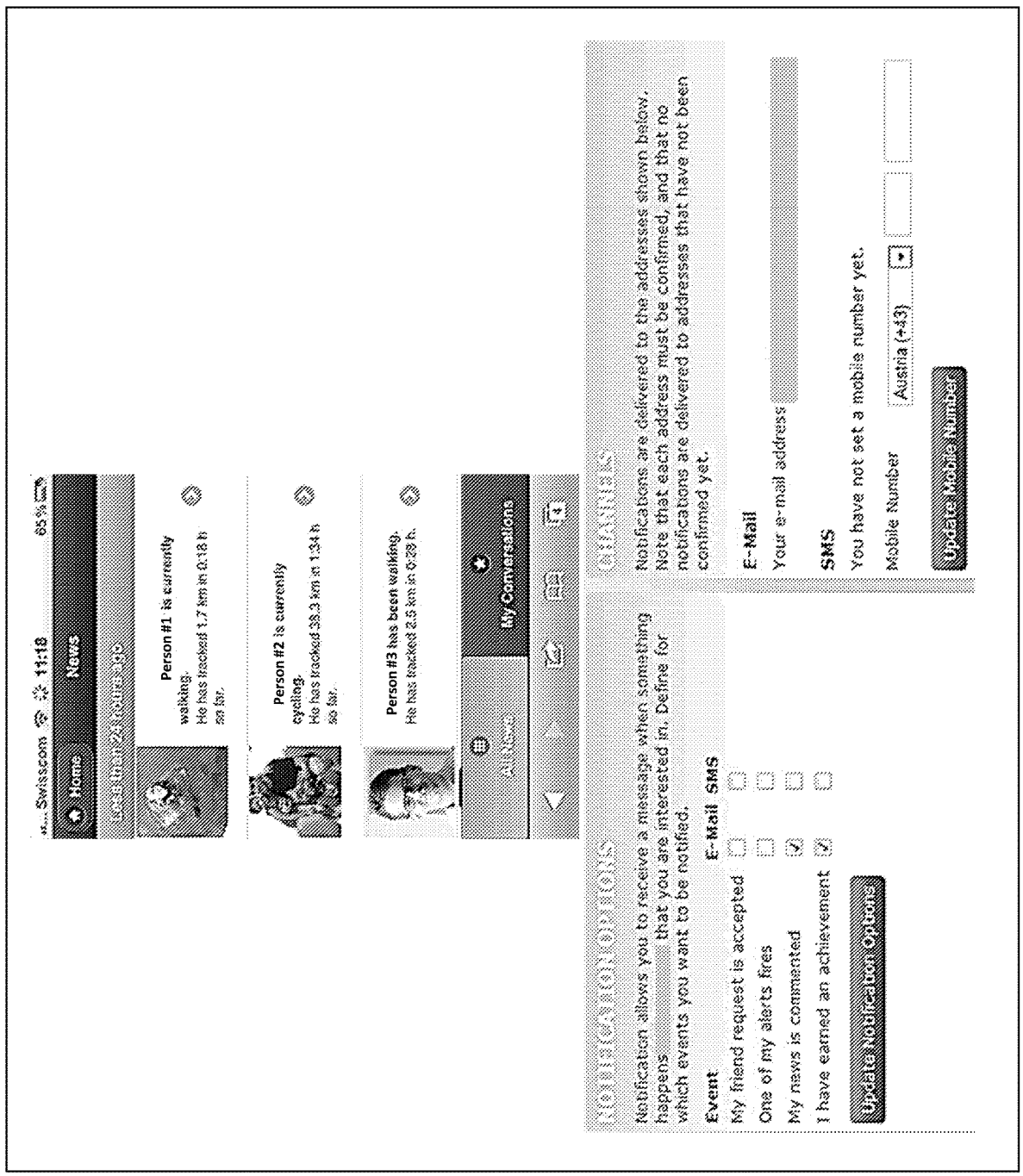
FIG. 13 illustrates an example display screen associated with news and notifications, in accordance with an implementation of the present application.

Referring to FIG. 13, news and notifications data entry display screen 1300 is illustrated and provided in accordance with an implementation of the present application. Data entry display screen 1300 can be configured to include various elements, including a "Newsfeed" (as known in the art) posting, notifications (e.g., by SMS or Email), and platform notifications (e.g., using graphical controls shown and described herein). In one or more implementations, a Newsfeed provides users with recent activity information of their friends. Users can choose to receive notifications about what is happening, for example, via SMS or email. Moreover, push notifications to the devices can be provided as well. SMS notifications can be useful for users who want real-time encouragement from their friends while the users are out training. Other social networking functionality can be provided, such as for finding friends for new introductions or to reconnect with others. A friend finding feature can be provided for users to friend other users on the system via a name search or email invite, or can use an integrated fitness style search that can include both public events and sports style search, e.g., "I'm a runner looking for other runners." Moreover, a user-friendly friend reporter system can be provided, for example, via a Newsfeed to keep users notified of activity levels of friends, substantially in real-time. One benefit of this feature relates to insurance companies. By using a friend reporter system, users' physical activity level can increase significantly (e.g., 50%) and users can enjoy significant weight loss.

In one or more implementations, server 180 and/or client 160 can be configured to establish groups of users, and such established groups having similar interests or backgrounds can be provided with functionality shown and described herein to team up and share information with one or more groups of users. For example, there can be two initial group types: Organizations (e.g., corporate groups), Teams (e.g., user groups). Teams can be created by all users and they are open by default. Group challenges can be created, and the newsfeed can be extended with news items from group users who can be sharing respective elements with their teams or others (e.g., everyone or unlimited). Further, a group directory can be maintained that is searchable and that lists groups that are open or moderated. Users can be prompted to specify their respective locations and fitness interests, which can be useful for searching on the group names and descriptions, and suggesting teams to join. This is helpful with getting users socially engaged, and can preclude an empty news feed. In addition, live chat functionality can be supported.

Figure 14:
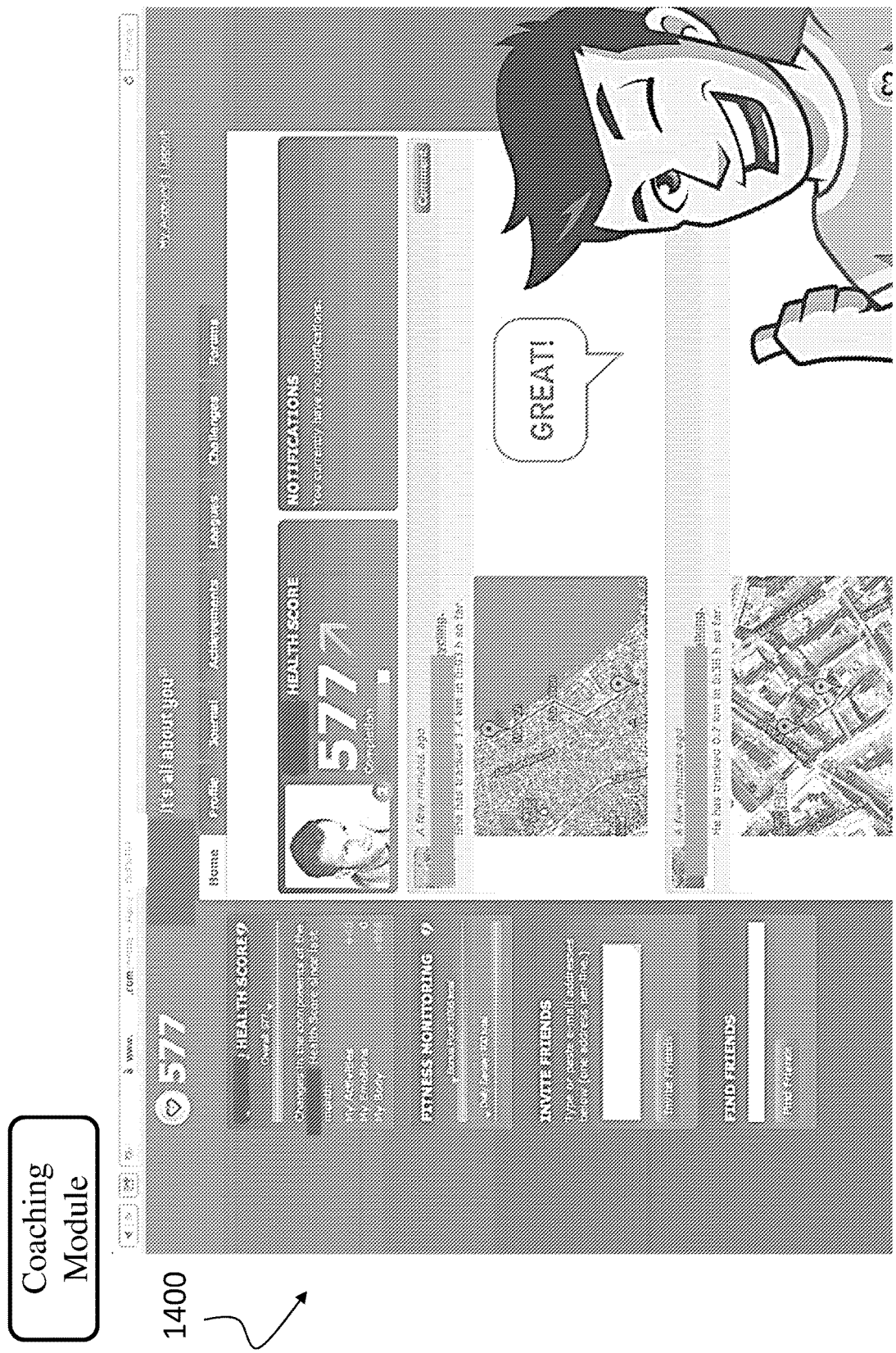
FIG. 14 illustrates an avatar in accordance with one or more implementations.

As noted above, in one or more implementations the present application supports use of an avatar and that can be integrated with artificial intelligence. An example of the avatar ("Q") illustrated in the example display screen 1400 in FIG. 14. Multiple behavior levers and novel techniques can be utilized that are based on research from health psychology, psychotherapy, behavioral economics, and influence supporting participants to opt in to healthier behaviors either on their own or with the assistance of a health coach or avatar: "Q," which can include an intelligent feedback loop, be a personal companion, include light artificial intelligence being used for providing the user with feedback of his/her lifestyle based on activity, nutrition consumption, stress and sleep. Moreover, the avatar can function as a mascot, be represented by a male or female companion who is there to inspire users to improve their Health Score and overall life quality, and provide intelligent suggestions based on a user's data input on the system. Further, the avatar can function as a coach for self-defined goals that the user sets, and can further be "brandable" to corporate partners.

Thus, in accordance with one or more implementations, users select a male or female version of the avatar "Q" to be their companion on the system. The avatar "Q" can have two principle roles: to function as a guide and companion when using the system; to let users know about notifications and alerts; and to explain, help and provide a walk-through to users when they first sign up. A second role of the avatar "Q" is that of coach/trainer. The avatar "Q" can form an integral part of a feedback loop with users—from nudging them to continue working out to setting them concrete training plans the avatar "Q" can be present. The avatar "Q" can appear on both a web platform and in a mobile app and can communicate with users in various ways, including but not limited to speech bubbles. In one or more implementations, the avatar will access content from the various trackers and situations on the platform to allow intelligent interactions with the user. The avatar "Q" can function as a coach to regular users and assist them in their training by providing training plans.

The present application further supports a "physician view," which can invite a user by requesting access in a specific role, such as "Personal Trainer" or "Physician". In one or more implementations, the role determines specific access rights for the user. The user can grant or deny access and is made aware of the access rights being granted, e.g., "The health professional WILL be able to READ your WORKOUTS."; "The health professional WILL be able to MODIFY your GOALS." One or more of the following features can be made available to health professional for users that have granted access: A free text comment (specific to the relationship of the health professional to the user); Tags (which can also be used for risk stratification into amber complex, red, etc.); Alerts; Filtering (such as by risk and alert state); Setting of fitness goals (e.g., Run 5 km for 5 weeks); and Setting of training plans (which can be done manually, or by copying from existing plans).

Furthermore, a recommendation module can be provided in connection with lifestyles. In a Health Professional View, for example, the health professional (physician, nurse, personal trainer, or the like) can provide direct recommendation to a user, in such cases when the user has specifically granted access to the professional. In one or more embodiments, the avatar "Q" provides a corporate customer client base with innovative lifestyle guidance, which will motivate the user to a more active healthy and happy life. The avatar "Q" can also provide knowledge and activities in a number of areas, such as: Fitness/Sporting activities—if a user has not been active or has only been trying one sport type; Diet/Nutrition—prompting the user to drink enough water over the course of a day (intelligence module would suggest the user drink more water if engaging in a lot of activity that day); Stress—if a user is registering high stress levels the avatar "Q" will provide him with overview and navigation he can take to his/her Physician; and Sleep—a user consistently recording poor sleep will be able to review their sleeping patterns and consult for professional advice.

As shown in data entry display screen 1400, the avatar Q can be configured to represent a coach that provides a user with the coaching role of the health professional (personal trainer or physician). Thus and in connection with setting goals and training plans, Q can function as a coaching tool.

In one or more implementations, the present application supports an inference engine that, as described in the section above, provides a total integrated lifestyle feedback loop that uses artificial intelligence. The feedback loop engine of the present application can learn and store important statistical lifestyle data of the user that helps the user to navigate through the complexity of life. The feedback loop can look at all aspects of a user's health and begin to establish patterns of their lifestyle. Clients of a corporate customer who experiences stress, unhealthy eating habits or sleep disorders can be able to review these patterns and make necessary changes. Further, the components of the Health Score Platform are interlinked so as to suggest ways for users to improve their health and their Health Score, based on an intimate knowledge of the Health Score. Moreover, data can be preferably kept anonymous and secure in any engine calculation.

In one or more implementations, the present application supports user help, such as in an on-line or other digital fashion. For example, support can include instruction videos, answers to frequently asked questions (FAQ), contact support, help with getting started on web platform, and mobile app help screens. For example, help is offered to users via an FAQ online and a support forum function that allows users to report bugs and issues. The tracker application also can also be configured with a dedicated help section.

In accordance with the present application, security is a core feature. In accordance with one or more implementations, communication with devices can be protected by HTTPS using high degree and use of security certificates to protect identity of its servers. User data can be securely protected using current cryptographic methods, and that can break the link between user data and account the data belongs to. A remote data center can be employed with significant logical and physical security, and can employ firewall technology not only on the network layer, but also on the application layer. Accordingly, application data can be sent securely and encrypted to the web platform, and a secure payment system can be employed for receiving payments, such as related to subscription fees (e.g., per use, monthly, annual, or the like). Moreover, privacy concerns can be addressed, for example, relating to HIPAA or other regulatory compliance.

Figure 15:
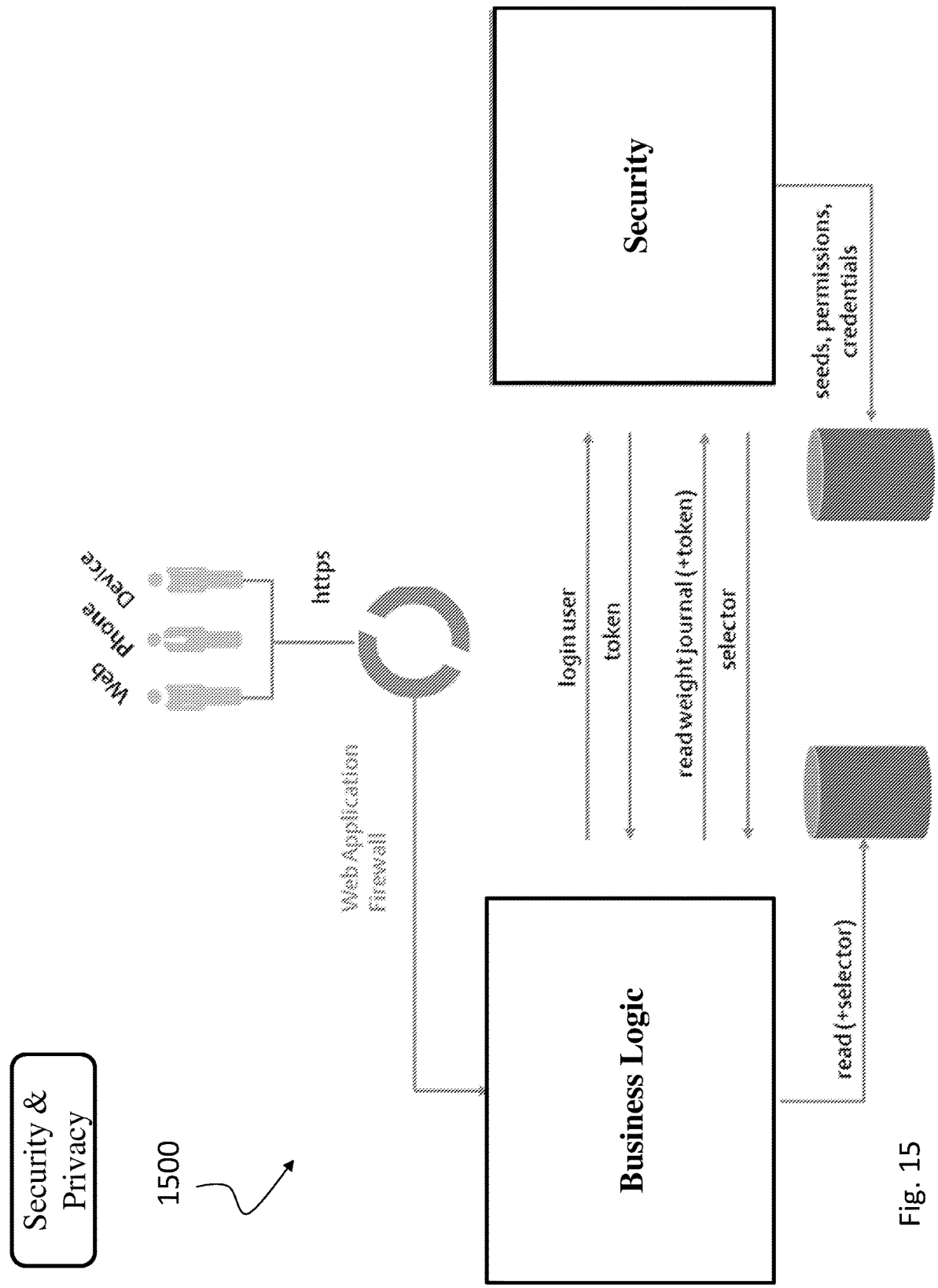
FIG. 15 illustrates an implementation of the present application that separates a link between health information and account information.

FIG. 15 illustrates an example diagram 1500 illustrating an implementation of the present application that separates a link between health information and account information. After a user logs in, such as by presenting proper credentials, a security server (e.g., server 180) issues a token. In order to access health information (business data), the business logic can request the selector(s) corresponding to that data from the security server, by presenting the token acquired earlier. After the token authorizes the access to the specific data, the security server can provide those selector(s). The business logic then uses the selector(s) to locate the data in the business database. From an architectural point of view, this centralizes security logic in the security server. This is a desirable property, as it makes it easier to maintain the security logic and ensure its correctness (vs. an opposite situation where the security logic can be scattered throughout the business logic).

The system 100 according to the present application can be designed as a user centric platform. The user decides in his/her profile settings what kind of information he/she would like to share with friends. In one or more implementations, only a subset of data can be shared with friends on the system 100. Those can include, for example: the user's Health Score, the user's fitness activities, a profile picture and profile text, achievements, and a list of friends. Other data, such as personal data relating to weight, medical history, lifestyle questions, quality of life questions, blood values, are preferably not accessible or shared on the system.

In an implementations, information can be received from a user during a registration process regarding the user's location (e.g., country), email address and password, data points to enable a first Health Score at first sign-up (e.g., age, gender, weight, height), and acceptance of terms of use. Moreover, a data/content repository, content distribution, and blog integration can be provided with social networking sites. In one or more implementations, integration with a content management system ("CMS") of a respective and possibly corporate customer is supported. For example, the Health Score can be integrated into content specific products of the corporate customer, meaning that the Health Score can be calculated substantially in real-time and be distributed to alternative client platforms such as the CMS platform of the corporate customer showing the total energy produced or distance of the active users.

In accordance with the present application, relevant parts of the feedback loop logic reside in the individual subsystems of the platform. Accordingly, a rule engine is implemented for notifications that include programming logic that reside in the various subsystems, such as a Forums system, a News system, and/or a Workout system. These rule engines can submit notifications to the feedback loop system. The feedback loop system itself can be construed in terms of a notification scheduler that runs processors on queued notifications in order to eventually deliver those notifications over channels to users. Moreover, a notification domain can be assigned to each notification, which allows users to choose delivery channels per notification domain. This simplifies the user experience.

In one or more implementations, Health Score information can be provided in an integrated fashion with, for example, one or more of social networking, location information, achievements of friends, nutrition tracker, an inbox, avatar(s), challenges, and invitation.

Figure 16:
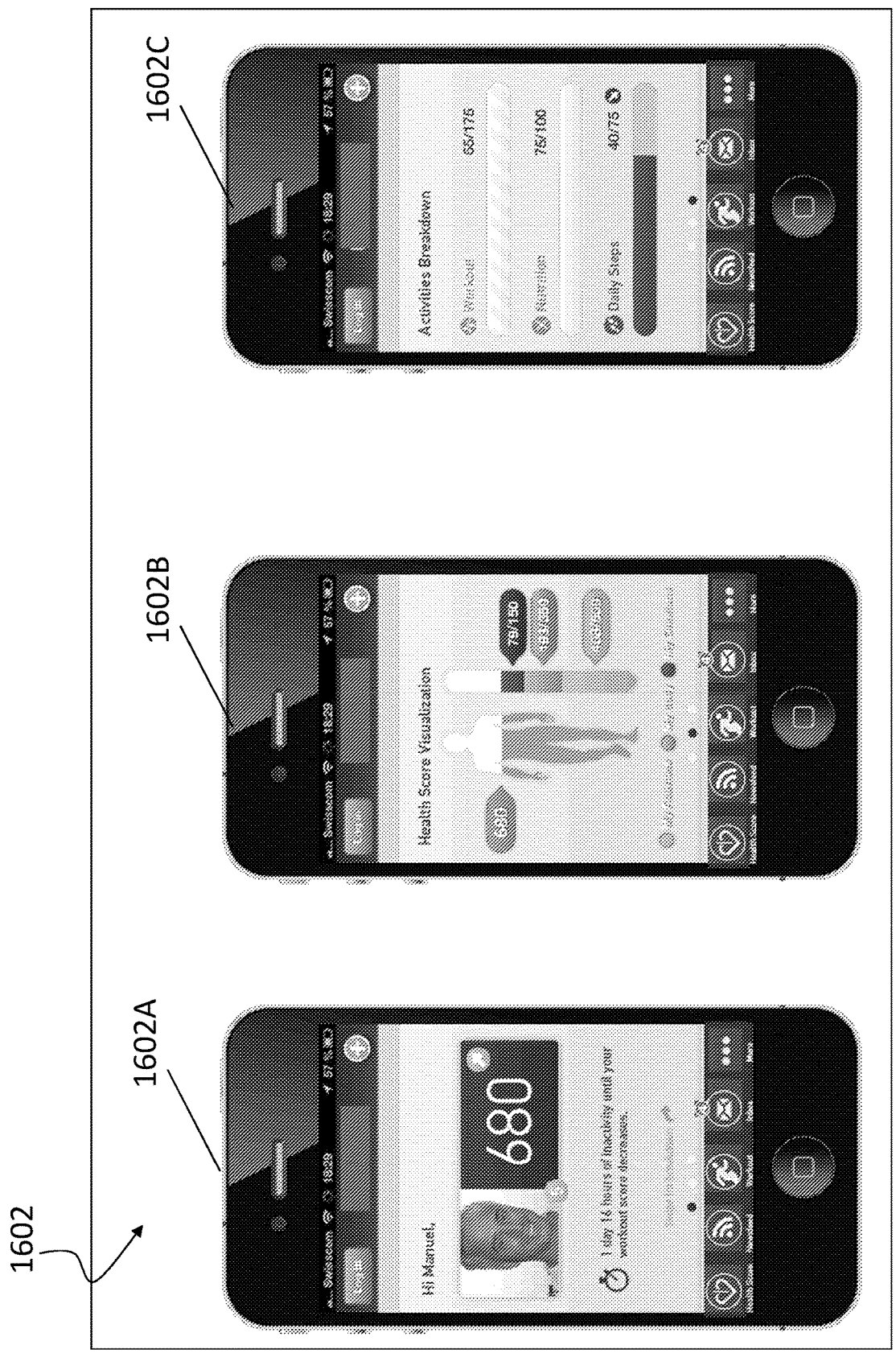
FIG. 16 illustrates mobile computing devices running one or more mobile applications, in accordance with implementations of the present application.

FIG. 16 is a diagram that illustrates a mobile computing device 1602 (i.e., client 160) executing a mobile application, in accordance with one or more implementations of the present application, at various states of operation (i.e., 1602A, 1602B, and 1602C). In the state of operation 1602A, the mobile computing device 1602 provides a Health Score, which includes a rising arrow to represent improvement, and a timer function associated with a workout score can be provided. Further, in the state of operations 1606B, the mobile computing device 1606B provides a Health Score visualization that displays relative values in connection with the user's activities, the user's body and the user's emotions. Moreover, in the state of operation 1602C, the mobile computing device 1602 provides an activities breakdown, in connection with workouts, nutrition and daily stops.

Thus, as shown and described herein, the present application provides for information to be received from users and devices, and processed to provide alerts and notifications. In one or more implementations, one or more rule engines can be provided that periodically and/or continuously generates notifications to users. Particular implementations can depend on a respective subsystem and its specific notification requirements. The notifications can be core information elements driving the feedback loop. Generally, the notifications can be characterized as follows: notifications can be feedbacks or questionnaires; notifications can be presented by an interactive avatar. Moreover, the notification generating rule engines can be part of individual subsystems generating those notifications. The feedback loop system can provide a generic infrastructure for scheduling, processing, and delivering notifications over various channels.

Regardless of the implementation, the system provides a means for assigning a numerical value that represents the relative health of an individual. The numerical value is described herein as a "Health Score" and can be used by server 180 and/or client 160 to assess to the individual's health based on health related information collected from a user. The Health Score can be calculated based on the collected health information using an algorithm. The user or the communication subsystem provides the system the health related information concerning a number of health parameters. Predetermined weighting factors are used as variables to calculate and assign a relative value of each of the parameters that are used to calculate the Health Score. The user's Health Score can be then calculated by combining the weighted parameters in accordance with an algorithm. For example, the parameters can be a person's blood glucose level and body weight. Server 180 and/or client 160 applies a weighting factor "a" is applied to the blood glucose data and a weight factor "b" can be applied to the body weight data. If the blood glucose information is a more important factor in determining a person's health than body weight, then the weighting factor "a" will be larger than weighting factor "b" so that the blood glucose data has a larger impact on the calculated Health Score (e.g., Healthscore=Glucose*a+(Weight/100)*b). In certain implementations, the weighting factor is a non-unity value (e.g., greater or less than one, but not one). Fewer or additional factors can be included in the calculation of the Health Score, and an offset value can be included that is added or subtracted or which modifies the entire calculation, in certain implementations such as to account for age or gender as two possible reasons; however, the foregoing is intended as a non-limiting example of how to calculate a Health Score. Other parameters that can be measured and included in the calculation include blood pressure measurements, height, body mass index, fat mass, medical conditions such as diabetes, ventricular hypertrophy, hypertension, irregular heartbeat and fasting glucose values. Where absent, a parameter can be omitted from the calculation or it can be estimated from other parameters and/or values obtained from a sample group of individuals having similar parameters.

In addition to intrinsic medical parameters, server 180 and/or client 160 receive information associated with physical activity of a user and processes the information to calculating his or her Health Score. As noted herein, physical activity can be monitored by a health band via an appropriate sensor dependent on the activity. Sensors can include a GPS unit, an altimeter, a depth meter, a pedometer, a cadence sensor, a velocity sensor, a heart rate monitor or the like. In the case of gym-based activities, computerized exercise equipment can be configured to provide data directly on the program completed by the user (for example, a so-called elliptical/cross-trainer can provide far better data on the workout than a user's pedometer etc). Although automated capture of parameters concerning a user's physical activity can be preferred, a user interface for manual activity entry can be also provided. In this regard, an exercise machine such as a treadmill, elliptical, stationary bike or weight lifting machine with a rack of weights or bands can be provided with a communications interface to communicate with the system described herein to provide extrinsic physical activity parameters to the system and to receive and further include a processor configured to process data from the system so as to automatically adjust an exercise program at the exercise machine to meet a goal, challenge, or other objective for that user.

Lifestyle data such as diet, smoking, alcohol consumed and the like can also be collected and used in calculating the Health Score. In one embodiment, a barcode or RFID scanner can be used by a user to capture data on food and/or nutrition that is consumed, and that can be then translated at a remote system, such as the server or a website in communication with the server, into parameters such as daily calorie, fat and salt intake. In part, the system relies on such data being provided by the user while other data can be obtained through data network connections once permissions and connectivity rights are in place.

Physical activity and lifestyle data can be tracked over time and a decay algorithm can be applied when calculating its effect on the Health Score, as is discussed in more detail below. As such, physical activity far in the past has a reduced positive effect on the Health Score. Preferably, the weighting factors used in the algorithm for the computation of the Health Score are adjusted over time in accordance with a decay component which can be arranged to reduce the relative weight of the parameters that are used in the calculation. The decay component can itself comprise a weighting value, but can also comprise an equation that takes into account at least one factor associated specifically with the user, such as the user's weight or weight range, age or age range, any medical conditions known to the system, and any of the other parameters that may be known to the system, or a curve that can be configured in view of these factors so that a value can be read from the curve as a function of the values along the axes for that user. In this way, the decay component can reduce the relative weight of the parameters used in the Health Score calculation for a first user differently than for another user, such as when the first user has a first age or age range and the second user has a second age or age range.

A central system, preferably a database and website that can be hosted, for example, by the server 180, maintains data on each user and his or her Health Score and associated parameters and their trends over time. The data can be maintained in such a way that sensitive data can be stored independent of human identities, as understood in the art.

The calculated Health Score for each user can be then processed in dependence on a system, group or user profile at the central system. Depending on the profile settings, the Health Score and trends associated can cause various automated actions. For example, it can cause: triggering of an automated alert; providing user feedback such as a daily email update; triggering the communication of automated motivation, warnings and/or goal setting selected to alleviate a perceived issue; adjustment of a training program; or automated referral for medical analysis.

The user's Health Score can be also provided to a designated group of recipients via a communication portal. The group of recipients can comprise selected, other, users of the system (e.g., friends and family) so that the Health Scores of the selected, other users can be compared against the Health Score of still others. In alternative arrangements, all users can see other user's scores, or the group of recipients can be defined as a specific health insurance provider so that price quotes can be provided to insure the individual. Other possibilities are within the scope the invention.

A data collection module executing on the processor can prompt a user to provide health related data corresponding to a number of parameters. In one implementation, one or more the parameters are provided automatically by the communication subsystem. The parameters can include the user's body weight, height, and age and fitness activity information. Such measurable medical parameters are intrinsic parameters of the user. The user's body weight and height provide information about the user's current state of health. The fitness activity information corresponds to the amount of exercise the user engages in. This information is an example of a physically activity parameter that is an extrinsic parameter of the user. For example, the user can enter information about his or her daily fitness activities, such as the amount of time the user engaged in physical activity and the type of physical activity. If the user went to the gym and exercised on a bicycle for thirty minutes, for example, that information can be entered into the system. The user's fitness activity information provides information about the actions that are being taken by the user in order to improve his or her fitness.

A user's body weight, height, age and fitness activity information are just some of the parameters for which information can be collected. The system can collect and process a multitude of other parameters that can be indicative of or impact a user's health. For example, parameters can include blood glucose levels, blood pressure, blood chemistry data (e.g., hormone levels, essential vitamin and mineral levels, etc.), cholesterol levels, immunization data, pulse, blood oxygen content, information concerning food consumed (e.g., calorie, fat, fiber, sodium content), body temperature, which are just some of a few possible, non-limiting examples of parameters that can be collected. Various other parameters that are indicative of a person's health that can be reliably measured could be used to calculate a person's Health Score.

A weighting module can recall weighting factors from the memory. The weighting factors can be multiplication coefficients that are used to increase or decrease the relative value of each health parameters. A weighting factor can be assigned to each health parameter as shown in the formulas herein. The weighting factors are used to control the relative values of the health parameters. Some health parameters are more important than others in the calculation of the users' Health Score. Accordingly, weighting factors are applied to the health parameters increase or decrease the relative affect each factor has in the calculation of the user's Health Score. For example, a user's current body weight can be more important than the amount of fitness activity the user engages in. In this example, the body weight parameter would be weighted more heavily by assigning a larger weighting factor to this parameter. The weighting module applies the recalled weighting factors to the collected health parameter values to provide weighted health parameter values. The weighting factor can be zero in which case a particular parameter has no impact on the Health Score. The weighting factor can be a negative value for use in some algorithms.

After the parameters have been weighted, the user's Health Score can be computed via a scoring module operating in the processor. The scoring module combines the weighted parameters according to an algorithm. In one implementation, the Health Score can be the average of the user's body mass index (BMI) Health Score and the user's fitness Health Score minus two times the number of years a person is younger than 95. The algorithm formula for this example is reproduced below:

$$\text{Health Score} = ((\text{BMI Healthscore} + \text{Fitness Healthscore})/2) - 2*(95 - \text{Age}).$$

The user's BMI Healthscore can be a value between 0 and 1000. The BMI Healthscore is based on the user's BMI, which can be calculated based on the user's weight and height, and how much the user's BMI deviates from what is considered a healthy BMI. A chart or formula can be used to normalize the user's BMI information so that dissimilar information can be combined. A target BMI value can be selected which is assigned a maximum point value (e.g. 1000). The more the user's BMI deviates from the target value the fewer points are awarded. The user's Fitness Healthscore is based on the physical activity or exercise of a person. In one embodiment, it is the sum of the number of fitness hours (i.e., the amount of time the user engaged in fitness activities) in the past 365 days where each hour is linearly aged over that time so that less recent activity is valued less. The resulting sum can be multiplied by two and capped at 1000. This normalized the fitness information so that it can be combined to arrive at the Health Score. A target daily average of fitness activity is selected and is awarded the maximum amount of points (e.g. 1000). The user can be awarded fewer points based on how much less exercise performed, compared to the target.

In another implementation, the Health Score can be determined from a number of sub-scores that are maintained in parallel beyond the BMI Health Score and the fitness Health Score. Likewise, the Health Score can be determined using similar information in a combinative algorithm as discussed above using different or no age adjustments.

Intrinsic medical parameters are processed to determine a base Health Score. Extrinsic parameters such as those from physical exercise are processed to determine a value that is allocated to a health pool and a bonus pool. The value, preferably expressed in MET hours, associated with a physical activity is added to both the health pool and the bonus pool. A daily decay factor is applied to the bonus pool. Any excess decay that cannot be accommodated by the bonus pool is then deducted from the health pool. The amount of decay is determined dependent on the size of the health pool and bonus pool such that a greater effort is required to maintain a high health and bonus pool. The health pool value is processed in combination with the score from the intrinsic medical parameters in order to calculate the overall Health Score value. In one embodiment, the health pool value is a logarithm or other statistical function is applied to age the respective values over time such that only the most recent activity is counted as being fully effective to the health/bonus pool.

The Health Score can be based on a weighted combination of health factor(s) and the exercise record of the person over time. The health factors can be updated regularly by the user. For example, the user can provide health related information after every event that can be tracked and processed by the system. The user can update after a meal, after exercising, after weighing himself, etc. In the case of recordal of an activity/event by a sensor, portable device or the like, the captured/calculated parameters can be automatically uploaded and used to produce a revised Health Score. For example, feedback could be provided showing the effect of exercise while a user is running, working out on exercise equipment etc. In selected embodiments, feedback can be provided to an administrator such as a gym staff member where it can be determined that a user is exceeding a predetermined threshold (which due to knowledge of their health can be varied respective to their Health Score or other recorded data). Accordingly, the health related data can be updated in a near real-time manner.

The user can also update the information twice daily, once daily, or at other periodic times. Moreover, the Health Score can be based on an average of the information over time. Fitness activity, for example, can be averaged over a period of time (e.g. over a week, month, or year). Averaging data over time will reduce the impact to the Health Score caused by fluctuations in data. Periods in which the data was uncharacteristically high (e.g., the person was engaging large amount of fitness activity over a short period of time) or uncharacteristically low (e.g., person engaged in no fitness activity for a week due to an illness) does not dramatically affect the Health Score with averaging over time. The health related information can be stored in the memory or in a database accessible by the processor.

The stored data can also be used to predict future Health Scores for a user. A prediction module can analyze past data (e.g., fitness habits, eating habits, etc.) to extrapolate a predicted Health Score based on an assumption that the user will continue to act in a predicable manner. For example, if the data shows that a user has exercised one hour every day for the past thirty days, the prediction module can predict, in accordance with a prediction algorithm, that the user will continue to exercise one hour for each of the next three days. Accordingly, the scoring module can calculate a predicted Health Score at the end of the next three days based on the information from the prediction module. It can also factor the prediction into other actions. For example, the system can suggest a more exerting physical activity level or challenge to someone who has a high Health Score but is predicted based on past experience to then take a number of days off for recuperation. Furthermore, the system can provide encouragement to the user to maintain a course of activity or modify behavior. For example, the system can send a message to the user indicating that if the user increased fitness activity by a certain amount of time, the Health Score would go up by a certain amount. This would allow the user set goals to improve health.

The use of the Health Score allows for a relative comparison of a user's health with that of another person's even though each person can have very different characteristics, which would make a direct comparison difficult. For example, a first user (User 1) can have a very different body composition or engage in very different fitness activities as compared to a second user (User 2), which makes direct comparison of the relative health of each user difficult. The use of the Health Score makes comparison of the two users possible with relative ease. In one example, User 1 is slightly overweight, which would tend to lower User 1's Health Score. However, User 1 also engages is large amounts of fitness activities, thereby raising the user's overall Health Score. In contrast, User 2 has an ideal body weight, which would contribute to a high Health Score, but engages in very little fitness activity, thereby lowering the Health Score. User 1 and User 2 are very different in terms of their health related parameters. Accordingly, it would be very difficult to assess and compare the relative health of User 1 and User 2. In accordance with the invention, information related to certain health parameters is collected from User 1 and User 2, which is used to calculate an overall Health Score. A comparison of User 1's and User 2's Health Score allows for an easy assessment and comparison of the health of these two users even though they are very different and have very different habits. Therefore, the Health Score has significant value so that members of a group can compare their relative health and so that other entities (e.g., employers, health care insurers) can assess the health of an individual.

The health parameter data and Health Scores can be stored over time, in a memory or other database, so that a user can track his or her progress. Charts can be generated in order for a user to track progress and analyze where there can be improvement in behavior. Moreover, trends can be identified that can lead to the diagnosis of medical problems and/or eating habits. For example, if a person's weight is continuing to increase despite the same or increased amount of fitness activity, the system can trigger or suggest that they seek certain medical tests (e.g. a thyroid test, pregnancy test) to determine the cause of the weight gain.

In certain implementations, the majority of the system is hosted remotely from the user and the user accesses the system via a local user interface device. For example the system can be internet based and the user interacts with a local user interface device (e.g., personal computer or mobile electronic device) that is connected to the internet (e.g., via a wire/wireless communication network) in order to communicate data with the internet based system. The user uses the local interface device to access the internet based system in which the memory and software modules are operating remotely and communicating over the internet with the local device. The local device can be used to communicate data to the remote processor and memory, in which the data are remotely stored, processed, transformed into a Health Score, and then provided to the designated groups via a restricted access internet portal. Alternatively, the system can be primarily implemented via a local device in which the data are locally stored, processed, and transformed into a Health Score, which can be then communicated to a data sharing portal for remote publication to the designated groups.

The system can be implemented in the form of a social networking framework that can be executed by software modules stored in memory and operating on processors. The system can be implemented as a separate, stand alone "health themed" social networking system or as an application that can be integrated with an already existing social networking system (e.g., Facebook, MySpace, etc.). The user can be provided with a homepage in which the user can enter information, manage which information is published to designated groups, and manage the membership of the designated groups. The homepage includes prompts to the user to enter the health related information for the each of the various parameters. The user can enter his or her weight, date of birth, height, fitness activity, and other health related information. The user's Health Score can be then calculated. The Health Score can be shared with other users that are designated as part of a group permitted to have access to that information. Moreover, the user can view the Health Score information of others in the group. Accordingly, the user is able to compare his or her overall health with the health of others in the group. Comparison of Health Scores with others in the group can provide motivation to the individuals in the group to compete to improve their Health Scores. Other information, such as health tips, medical news, drug information, local fitness events, health services, advertising and discounts for medical and/or fitness related supplies and service, issuance of fitness challenges or health related goals, for example, can be provided via the homepage.

In further implementations, the Health Score can be a composite of a Metric Health Model score and a Quality of Life Model score. Combining scores from multiple models provides a more holistic assessment of a user's health. The Metric Health Model score assesses a user's health based on relatively easily quantifiable parameters (e.g., age, sex, weight, etc.) and compares those numbers to acceptable populations study models. The Quality of Life Model score focus on a user's self-assessed quality of life measure based on responses to a questionnaire (i.e., the system takes into account the user's own assessment of their health and life quality) because there are correlations between how an individual "feels" about his or her life and a realistic measure of health. A combination of the scores from these two models, which will be discussed in more detail below, provides a more inclusive and holistic assessment of health.

The Metric Health Model score can be based on medical parameter information of a user, such as their medical history information, attributes, physiological metrics, and lifestyle information to the system. For example, the system can provide the user a questionnaire to prompt responses (yes/no, multiple choice, numerical input, etc.) or provide the user with form fields to complete. Medical history information can include the user's history of medical conditions and/or the prevalence of medical conditions in the user's family. Examples of medical history information can include information such as whether the user has diabetes, has direct family members with diabetes, whether the user or family members have a history of heart attack, angina, stroke, or Transient Ischemic Attack, a history of atrial fibrillation or irregular heartbeat, whether the user or family members have high blood pressure requiring treatment, whether the user or family members have hypothyroidism, rheumatoid arthritis, chronic kidney disease, liver failure, left ventricular hypertrophy, congestive heart failure, regular use of steroid tablets, etc.

In one more implementations, the Metric Health Model score can also be based on user attributes. The attributes can include age, sex, ethnicity, height, weight, waist size, etc. In addition, Metric Health Model score can be based on physiological metrics of the user. Examples of physiological metrics can include systolic blood pressure, total serum cholesterol, high-density lipoprotein (HDL), low-density lipoprotein (LDL), triglycerides, high-sensitivity C-reactive protein, fasting blood glucose, etc. The inputs can also include parameters of a user's lifestyle. For example, lifestyle parameters can include inputs about whether the user is a smoker (ever smoked, currently smokes, level of smoking, etc.), how much exercise the user performs (frequency, intensity, type, etc.), type of diet (vegetarian, high-protein diet, low-fat diet, high-fiber diet, fast-food, restaurant, home cooking, processed and pre-packaged foods, size of meals, frequency of meals, etc.). These are some of the examples of parameters that can be used to compare the user's health indicators to survival probability models in order to calculate the user's Metric Health Model score.

The Metric Health Model score can be calculated by comparing the user's medical parameter information to survival probability models. A score, preferably in the range of 0 to 1000, with the top end signifying perfect health and the low side signifying poor health, can be derived following a two-step process. First, an overall survival probability is obtained from a combination of the survival probabilities generated by individual survival probability models, as described above. Second, the resulting survival probability, which is a number in the 0 to 1 range, is transformed using a parametric nonlinear mapping function into the 0 to 1000 range. The parametric mapping function is tuned so that it is linear, with a high slope, in the region of typical survival probabilities, and asymptotically slopes off in the low and high ends of the survival probability distribution. The mapping function is designed to be strongly reactive to changes in the typical survival probability region.

As discussed above, the Health Score can be composed of the Metric Health Model score, and also the Quality of Life Model score. The Quality of Life Model score is based on a user's answers to a set of questionnaires. The system can include several different questionnaires with some questions in common. The type of questionnaires and the type of questions therein presented to the user can be tailored based on a user's health parameters (i.e., user age, other data in the user's medical history, etc.). A specific questionnaire can be generated and presented to the user on the basis of information on the user that is known to the system. The questions can be presented with an appropriate multiple choice response that the user can check/tick on a form, with no free-form text is entered by the user to permit easier assessment of the responses. Other types of responses are possible (e.g., rating how true a statement is to the user 1-10). The following list provides several sample questions (in no particular order) on a number of health-related quality of life topics that can be used in a system questionnaire.

Thus, in a broad aspect, a method according to the invention can be understood as collecting health related information, processing the information into a Health Score, and publishing the Health Score is provided. A system for implementing the method can include a computer having a processor, memory, and code modules executing in the processor for the collection, processing, and publishing of the information. Information concerning a plurality of health related parameters of a user can be collected, particularly, both intrinsic values concerning the measurable, medical parameters of at least one natural person, and the extrinsic values concerning the activities of each such person(s) such as the exercise performed, the type of job the person has and the amount of physical work associated with the job (e.g. sedentary, desk job versus active, manual labor intensive job) and/or the calories/food consumed. Weighting factors are applied to the health related parameter in order control the relative affect each parameter has on the user's calculated Health Score. The Health Score can be computed using the processor by combining the weighted parameters in accordance with an algorithm. The Health Score can be published to a designated group via a portal. In one implementation, the portal can be an internet based information sharing forum.

Figure 17:
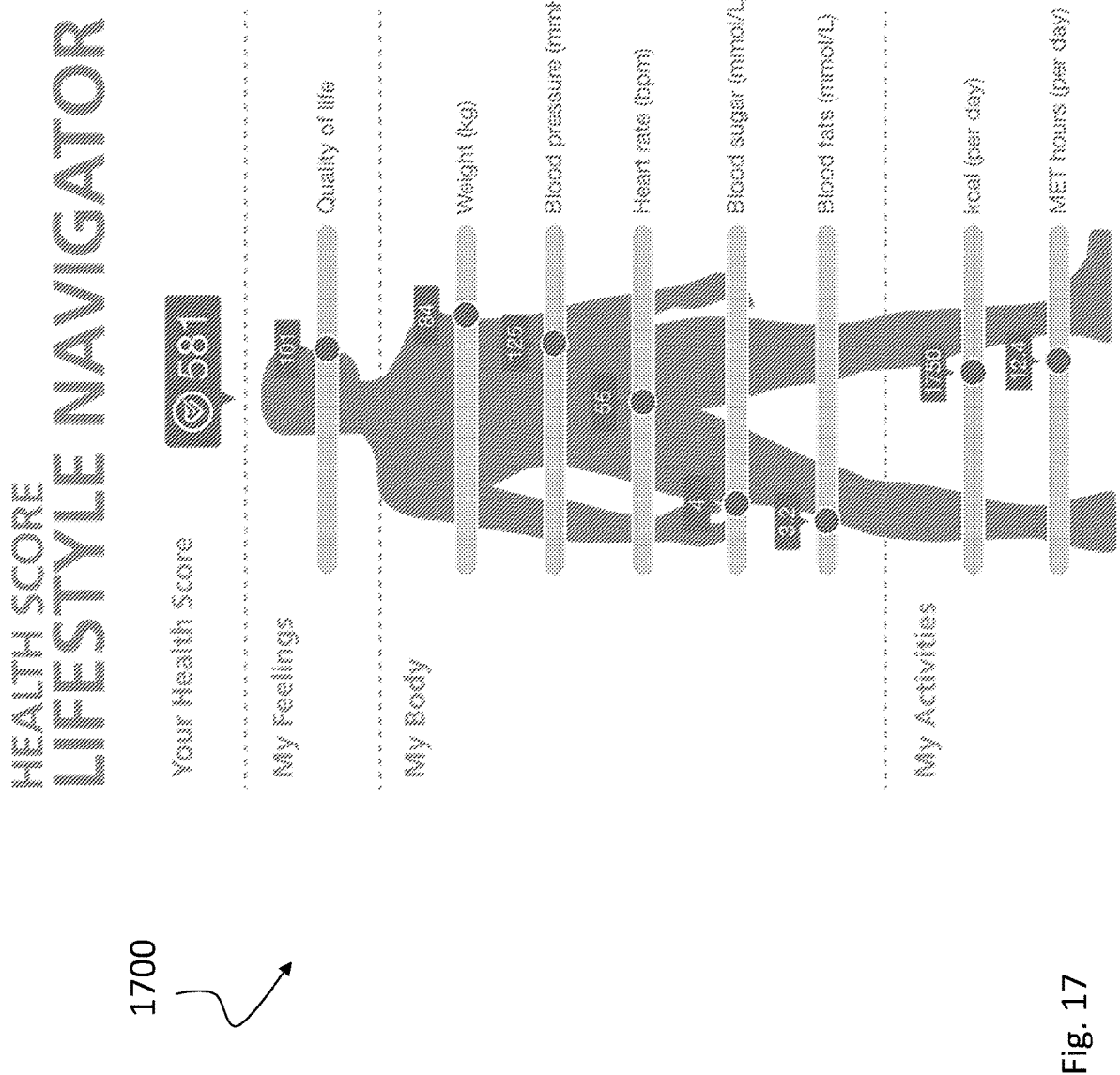
FIGS. 17-27 illustrate additional implementations associated with a lifestyle navigator, in accordance with the present application.

The present application is now further shown and described with reference to one or more implementations that includes one or more modules for providing a virtual Health Score lifestyle navigator. FIG. 17 illustrates an example display screen 1700 that includes graphical screen controls in the form of sliders for increasing and decreasing variables associated with a feelings, clinical observations and activities that are usable by server 180 and/or client 160 to process and calculate a user's Health Score. Although the graphical screen controls illustrated in FIG. 17 are in the form of slider controls, other graphical screen controls are supported by the present application including, but not limited to, drop down lists, text boxes, radio buttons, checkboxes, line graphs, bar graphs or other suitable graphical controls. In the example display screen 1700, the slider controls are movable along a respective axis and represent range from a low value to a high value. The slider controls enable selection of a respective value along the range. In the example display screen 1700, slider controls are provided for three general categories of information associated with a user's health. For example, values associated with a user's feelings, with a user's body (e.g., weight, blood pressure, heart rate, blood sugar and blood fats), and with a user's activities (e.g., kcal/day and MET hours/day) can be increased or decreased as a function of adjusting corresponding slider controls in a graphical user interface that is provided or operating on a computing device, such as a smartphone, tablet computer, notebook computer or other computing device.

In the example displayed in FIG. 17, a Health Score of 581 is shown and that is calculated as a function of variables included in the user's broad categories of feelings, body and activities. By providing selectable options, such as sliding bars, values can be selected that, when executed by a processor configured with instructions to calculate a Health Score, enable a user to simulate and vary a Health Score, such as to raise a Health Score by ten points by decreasing (e.g., losing) 20 pounds. Such a simulation can be provided by simply moving the slider control associated with weight (illustrated in kilograms), and the impact on the user's Health Score is instantly illustrated. This provides a user with an identifiable and measurable goal that can be set to improve the user's Health Score. In other words, if the user loses 20 pounds, the user's Health Score will increase.

In the example shown in display screen 1700, the respective slider controls associated with the user's feelings, body and activities are superimposed over a silhouetted image of a human body. In the example shown in display screen 1700, the quality of life slider is placed over the head of the silhouetted human body. The slider controls relating to the user's body are placed over the torso and upper leg portions, and the slider controls relating to the user's activities are placed over the legs of the silhouetted body.

With reference now to the respective slider controls illustrated in the example display screen 1700, a slider control is provided in which a numerical value of 101 is shown and that is associated with a user's subjective feelings, which represents the user's quality of life. With regard to the values associated with the user's body, slider controls are provided for weight (illustrated as 84 kg), blood pressure (illustrated as 125 mmHg), heart rate (illustrated as 55 bmp), blood sugar level (illustrated as 4 mmol/L), and blood fats level (illustrated as 3.2 mmol/L). With regard to values associated with the user's activities, slider controls are provided for calories (illustrated as 1750 kcal per day) and exercise (illustrated as 12.4 MET hours (per day)).

In one or more implementations, values relating to at least feelings, body and activities are accessed by one or more processors, such as in one or more databases, and used to provide default positions and value (e.g., labels) associated with the slider controls, such as illustrated in FIG. 17. In such configurations, a user desiring to review and/or adjust one or more values associated with the user's Health Score can move the slider controls from default positions corresponding with the with respective stored values. Using the respective slider controls, the user can adjust one or more of the values to cause a recalculation of the Health Score in accordance with the revised value(s).

Figure 18:
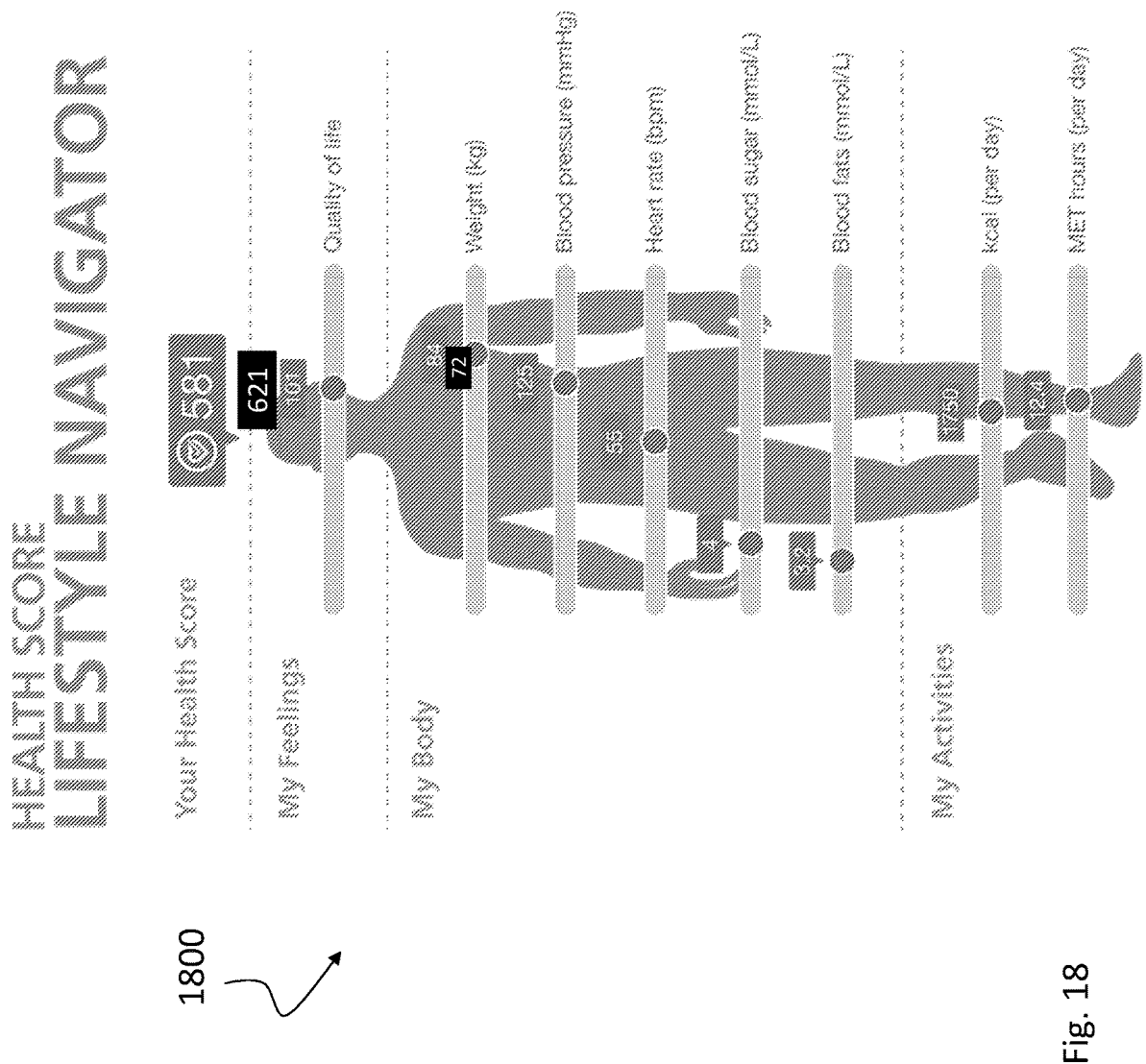

FIG. 18 illustrates an example display screen 1800 associated with a lifestyle navigator and that includes graphical screen controls in the form of sliders for increasing and decreasing variables associated with a Health Score. In the example shown in FIG. 18, the user has adjusted (i.e., lowered) a slider control illustrated in FIG. 17 and that is associated with weight (previously 84 kg) to a lower value (72 kg), which represents a hypothetical loss of weight. A corresponding adjustment (increase) in the user's Health Score (from 581 to 621) can be instantly calculated and displayed for the user. Thus, as shown and described in connection with FIGS. 17 and 18, a user desiring to raise a Health Score by nearly 40 points can do so simply by losing 12 kg of weight. A user, recognizing the value of improving a Health Score (e.g., for insurance purposes, social networking purposes, or simply to improve the user's quality of life) can define a recognizable and tangible goal by focusing exclusively on weight loss. It is recognized by the inventor that sustaining weight loss can be very difficult for a large number of people, and by supporting combinations of variables (e.g., blood pressure, heart rate, kcals, MET hours, or the like) users can define goals that are reasonably attainable and long-lasting. This provides a significant improvement over, for example, crash diets that often result in short-term gains, but are unsustainable over the long term. Instead, the present application provides options for users to select virtually countless combinations of health-related variables in order to attain desirable Health Scores.

Figure 19:
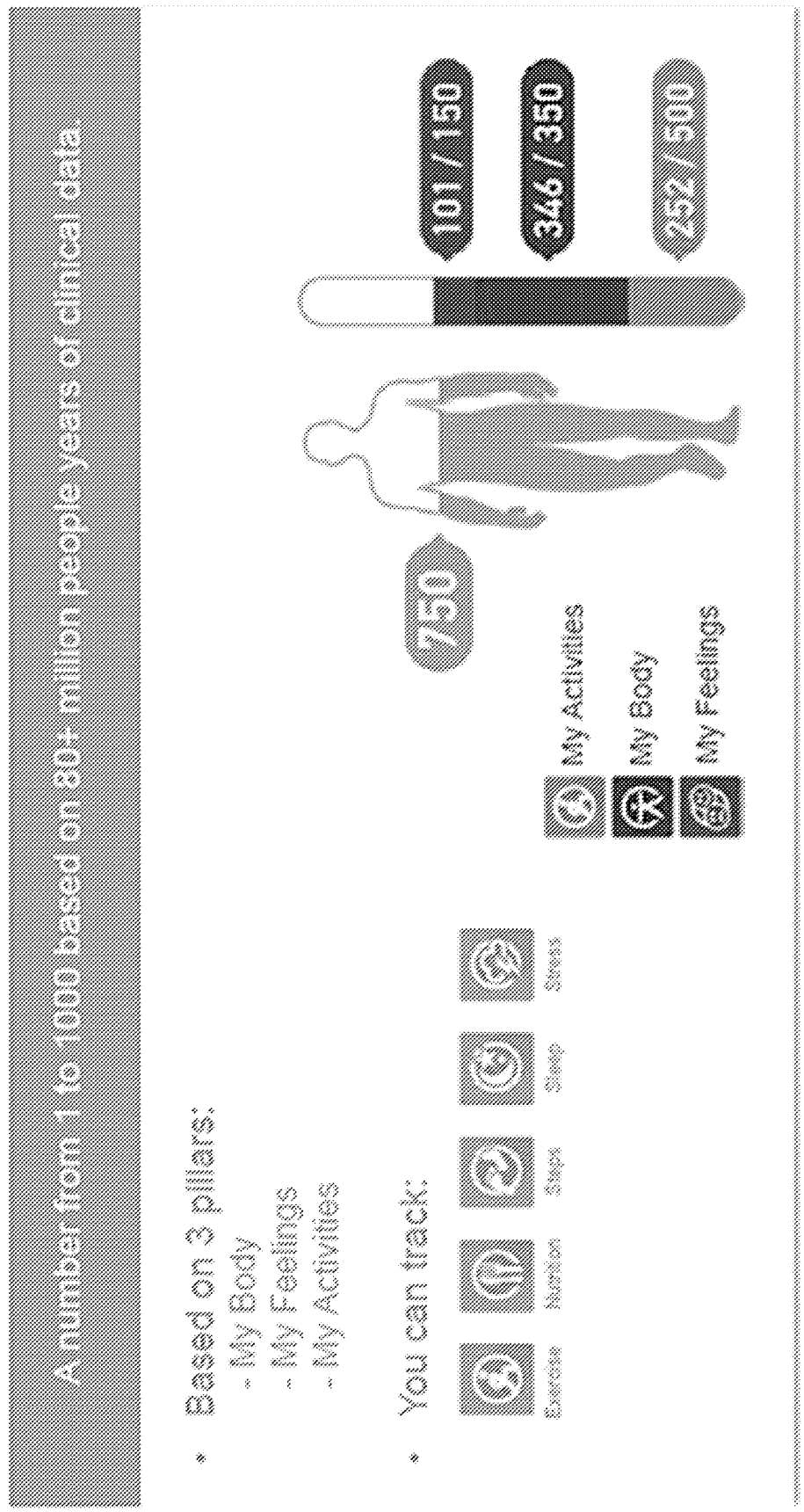

FIG. 19 illustrates an example display screen 1900 that includes additional graphical representations of values associated with a user's feelings (101 of 150), body (346 of 350) and activities (252 of 500). Thus, out of a total possible Health Score of 1,000, the user's Health Score is calculated to be 750. A series of prompts are further illustrated in example display screen 1900, including for a user to track exercise, nutrition, steps, sleep and stress, and that the user's calculated Health Score can be based on the three pillars: Body, Activity and Feelings.

Figure 20:
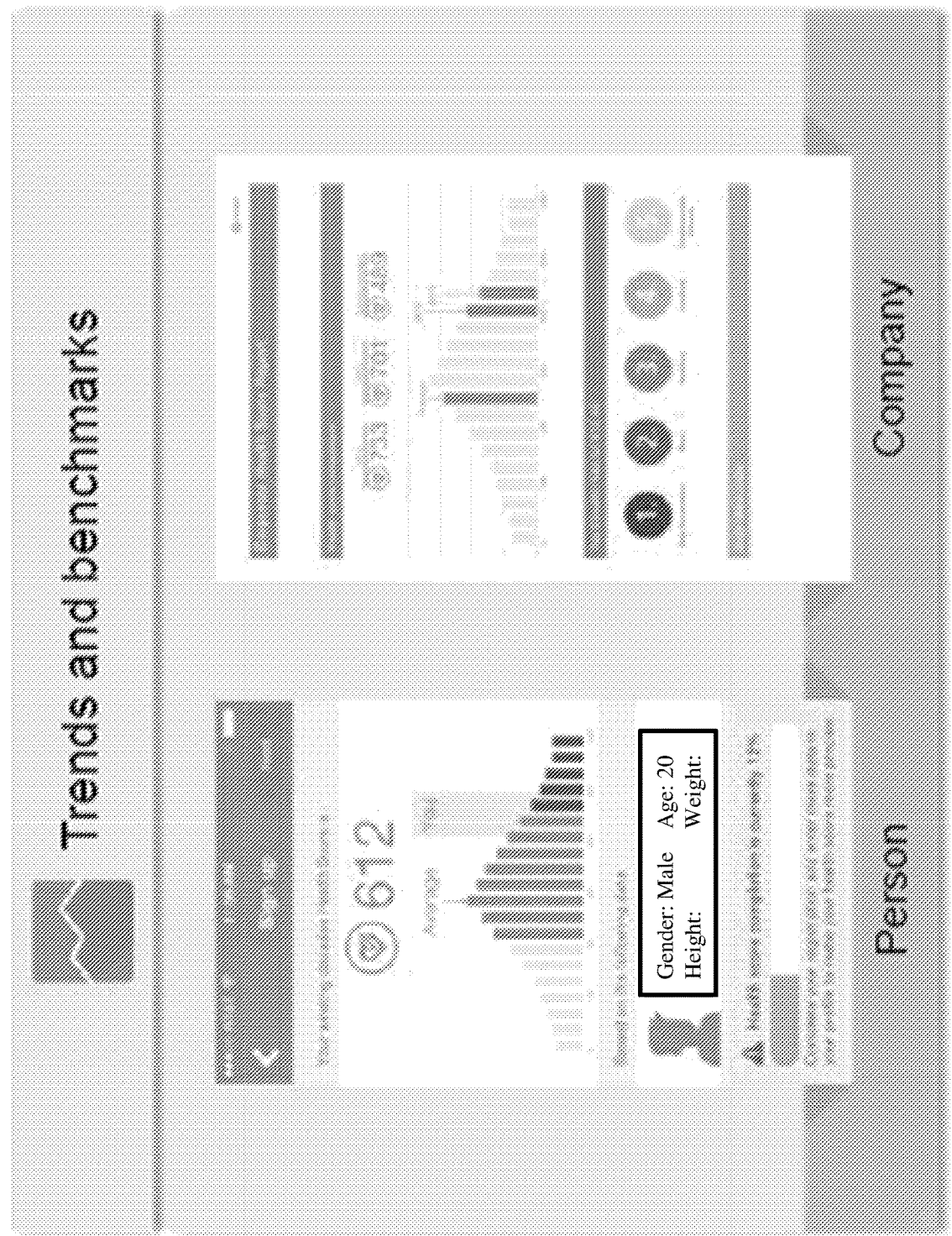

As noted herein, the present application supports managing and monitoring trends and benchmarks, in connection with Health Scores of an individual over time and a plurality of people. FIG. 20 illustrates an example display screen 2000 that includes trend and benchmark graphics associated with Health Scores of a single user, as well as Health Scores of a plurality of people who are members of company. Comparative Health Scores can be displayed for various departments within a single company, various branches (i.e., locations) of a corporation, geographic regions within a county or union, or other people who are related in various ways. Using Health Score information from a single person over time, or a plurality of people, the present application can provide trend and benchmark information in convenient and intuitive graphical displays, such as shown in example display screen 2000.

Figure 21:
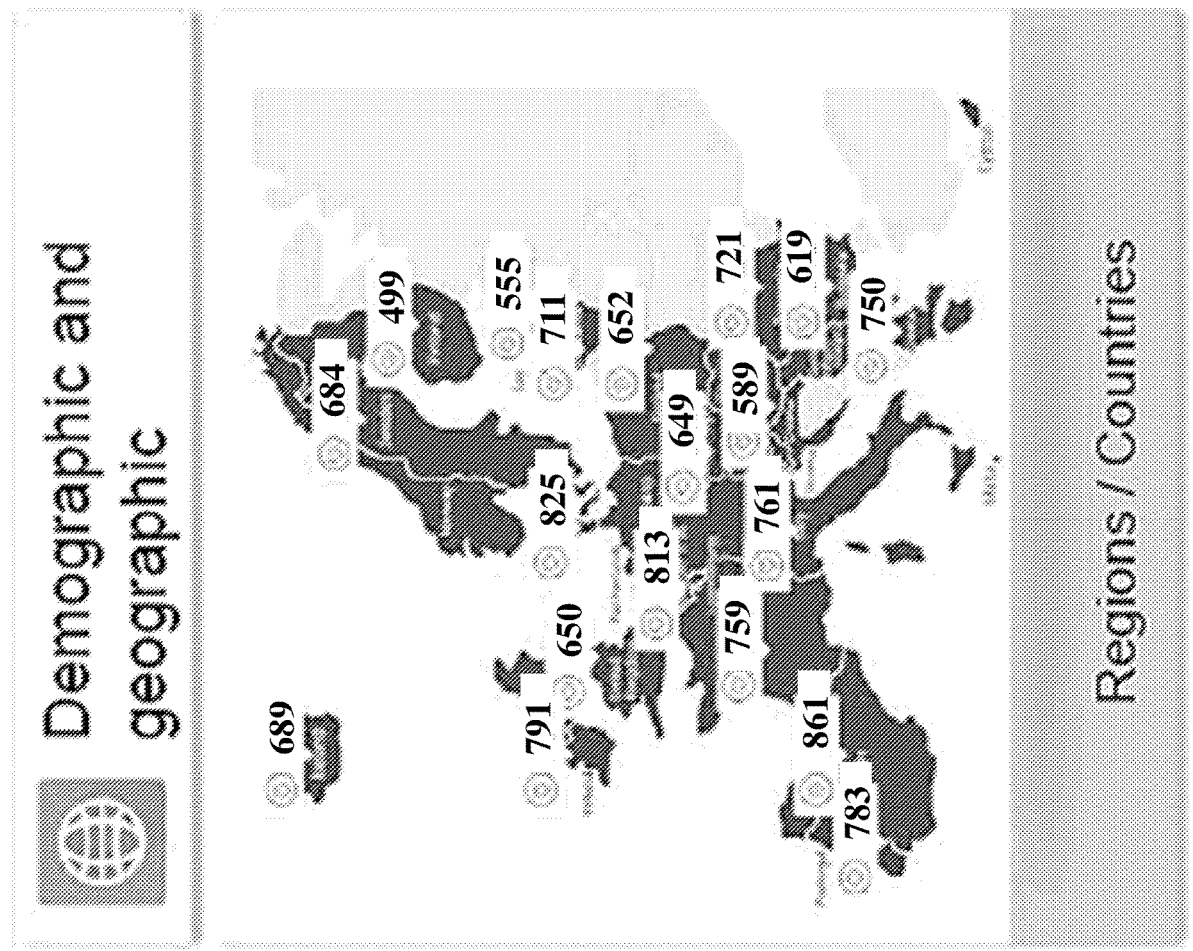

FIG. 21. illustrates another example display screen 2100 associated with benchmark information of Health Scores, and relates to Health Score information in various countries in a geographic area (e.g., Europe). As illustrated in display screen 2100, certain countries in Europe have relatively low Health Scores (e.g., 499 and 589), while others have relatively high Health Scores (e.g., 791 and 861). By providing benchmark and trend information associated with Health Scores in different countries, the present application can impact economies and businesses around the world. For example, a corporation may be considering building a manufacturing plant in a particular country due to local resources, tax benefits, labor availability or other concerns. However, after reviewing Health Scores in the country, the company may decide to move the operation in a different country that has a higher Health Score on the grounds that local health-related information, including relating to health costs, worker illness and related concerns outweigh the various economic incentives initially considered. Thus the present application can have far reaching effects that impact local and global economies.

Figure 22:

FIG. 22 illustrates a benchmark display screen 200 that shows participants in a road race and that displays each of the participants' respective Health Score, as well as a single Health Score for a given user, and corresponding variables associated with the given user's Health Score. In the example shown in FIG. 22, the user's time in the race, pace and distance are provided, as well as the calories burned and the user's heart rate. Information may be provided, for example, via GPS technology and biosensors worn or otherwise attached to the user to provide a user's respective values and current (and real-time) Health Score.

Figure 23:
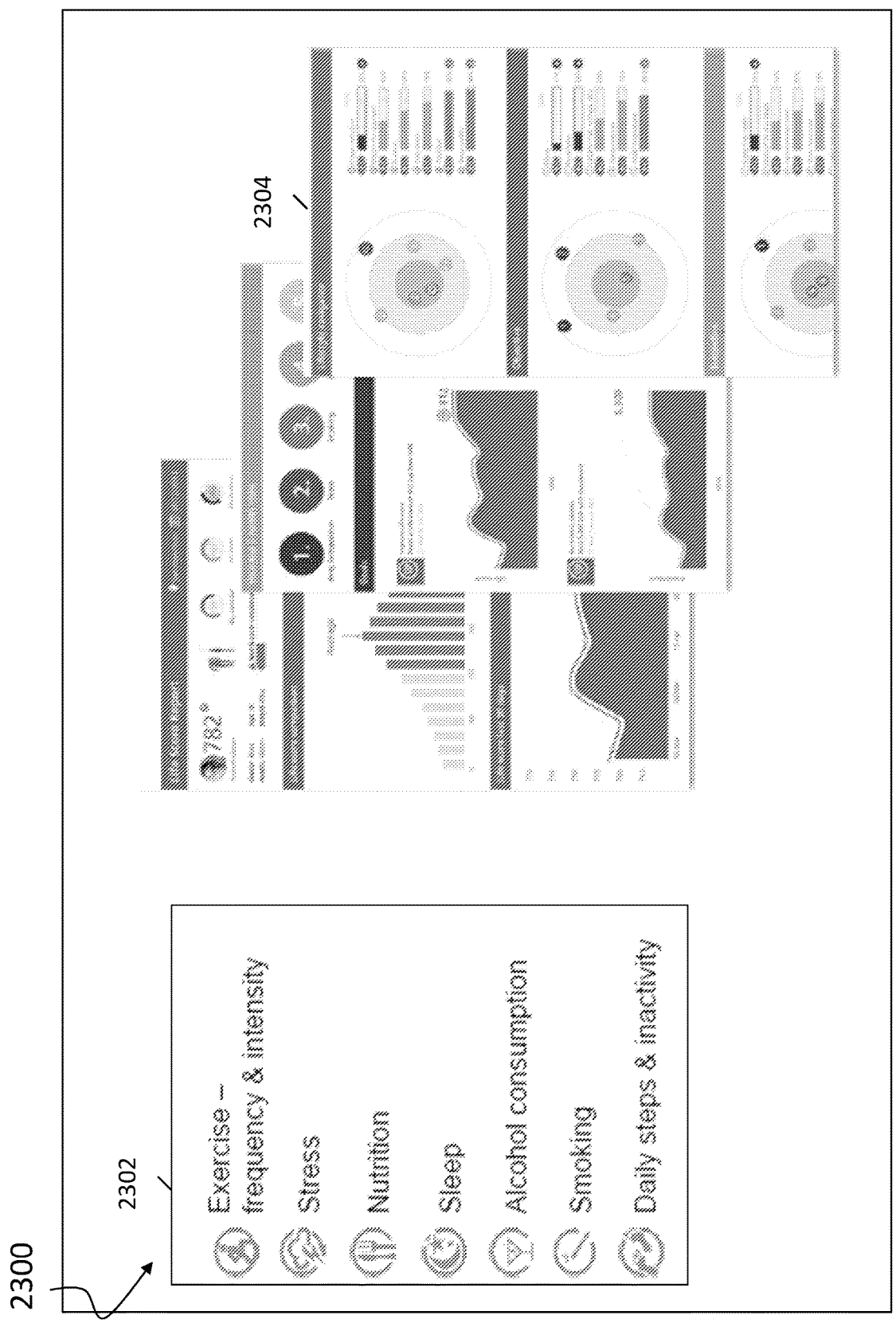

FIG. 23 is a block diagram 2300 that includes graphical displays associated with benchmarking Health Score information and an alternative implementation of displays associated with a virtual Health Score Lifestyle Navigator. Section 2302 identifies variables associated with calculating a Health Score, and include exercise frequency and intensity, stress, nutrition, sleep, alcohol consumption, smoking, and daily steps/inactivity. Section 2304 illustrates an implementation of a Health Score lifestyle navigator that includes an intuitive and convenient graphical representation of variables comprised in the user's Health Score and that illustrate current values, objectives, and subjective values associated with the user's Health Score. In the example displays in section 2304, a series of concentric circles are provided with corresponding graphical markers placed thereon (and/or therein) that represent respective values corresponding to feelings, body and activities, such as shown and described above with regard to a user's Health Score lifestyle navigator. In the example implementation shown in section 2304, the graphical markers that are positioned at or near the most center concentric circle represents higher (i.e., better) values associated with the user's Health Score. Thus and as illustrated in FIG. 23, alternative graphical representations are supported in connection with a Health Score lifestyle navigator for users to identify at a glance how they are doing with regard to categories of values and/or individual values associated with the users' Health Scores.

Figure 24:
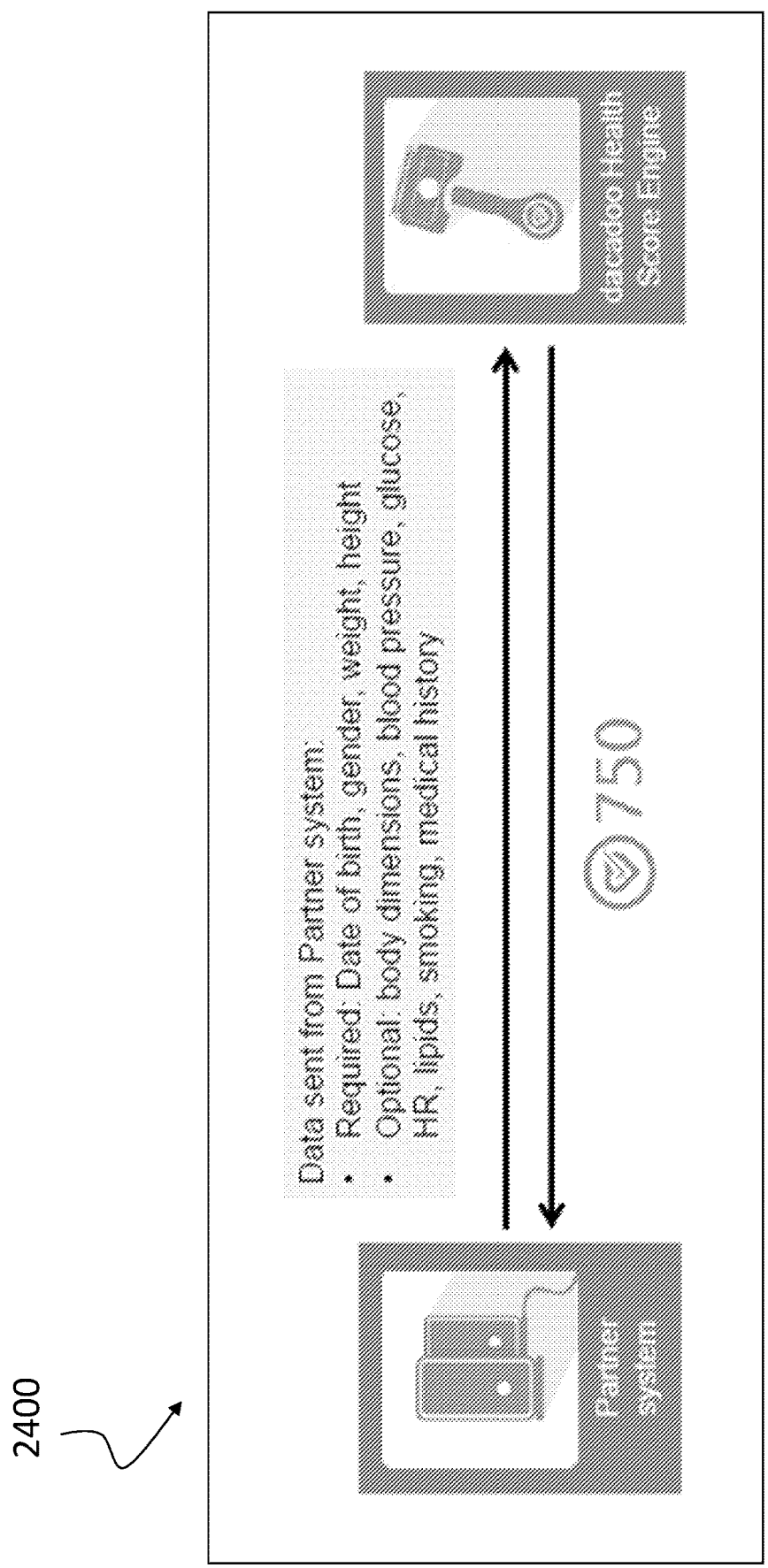

FIG. 24 is a block diagram that illustrates a symmetric exchange of information between a proprietor of the present patent application and an outside computing service, shown as a "partner system." It is recognized that various computing services, including social networks, medical systems and companies, hardware companies and other providers of products and services have access to information that can be processed and used to calculate a user's Health Score. In the example shown in FIG. 24, a partner system provide information including date of birth, gender, weight, height, body dimensions, blood pressure, glucose levels, HR, lipids, smoking and medical history information. The values that are received are processed and used to calculate a user's Health Score, which is shown in FIG. 24 to be 750.

Figure 25:
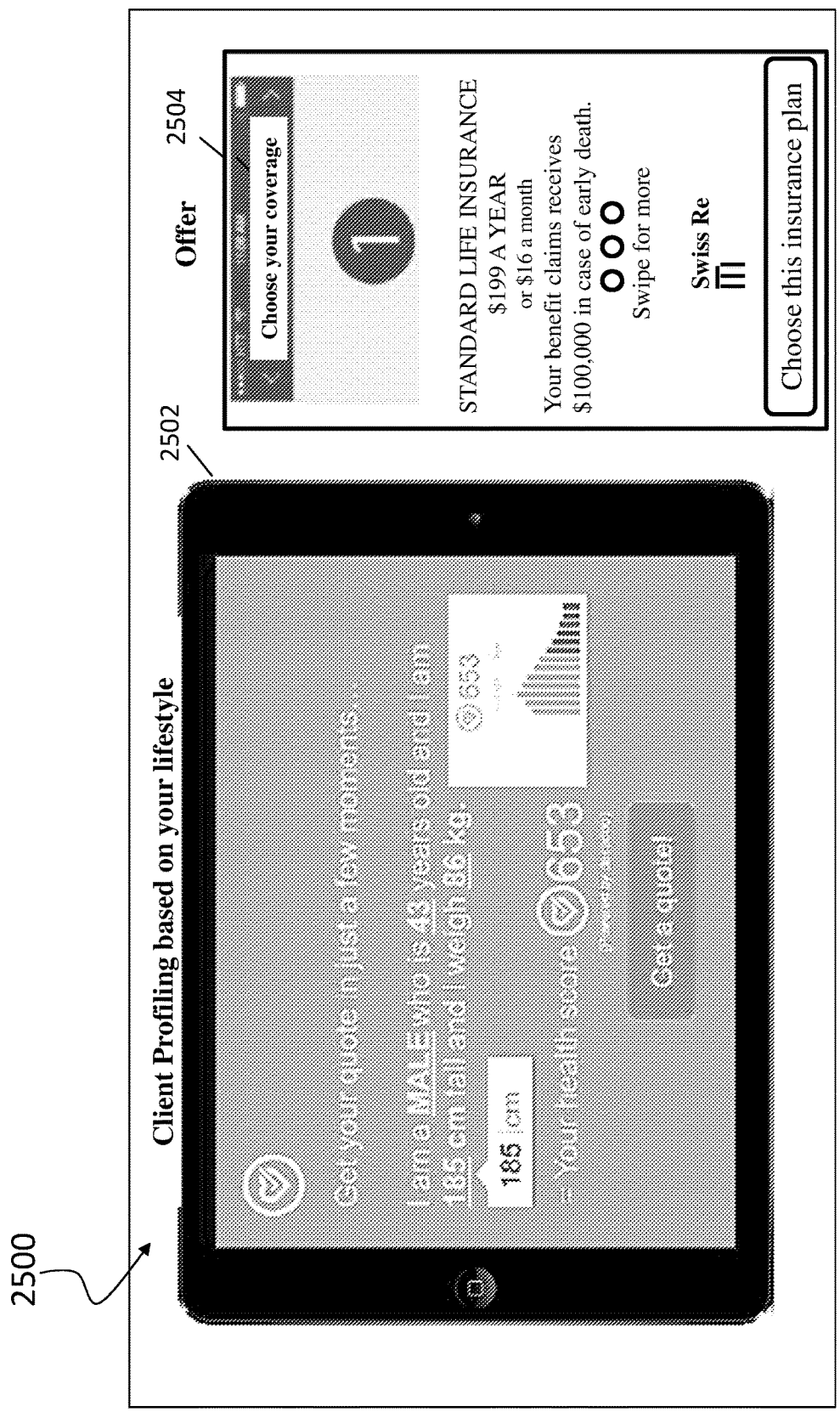

FIG. 25 illustrates an example implementation 2500 of the present application in which insurance rates and access to insurance are directly affected by a user's Health Score. In the example shown in FIG. 25, display screen 2502 can be provided for a user to receive an "instant" Health Score in connection with various body information (height and weight). A prompt can be further provided for the user to send the instant Health Score to an insurance provider and to receive a quote for an initial insurance rate. Display screen 2504 represents the insurance provider that received the user's instant Health Score and offering an insurance policy to the user at a rate of $199 per year. Thus, simply by receiving a single value Health Score that can be calculated immediately as a function of basic information, an insurance provider can offer an insurance policy. As more information is received by the insurance provider including, for example, an updated Health Score that can be calculated using additional information such as shown and described herein, an updated policy quote can be provided. The example shown in FIG. 25 illustrates one instance the Health Score having an economic impact both for service providers and consumers.

Figure 26:
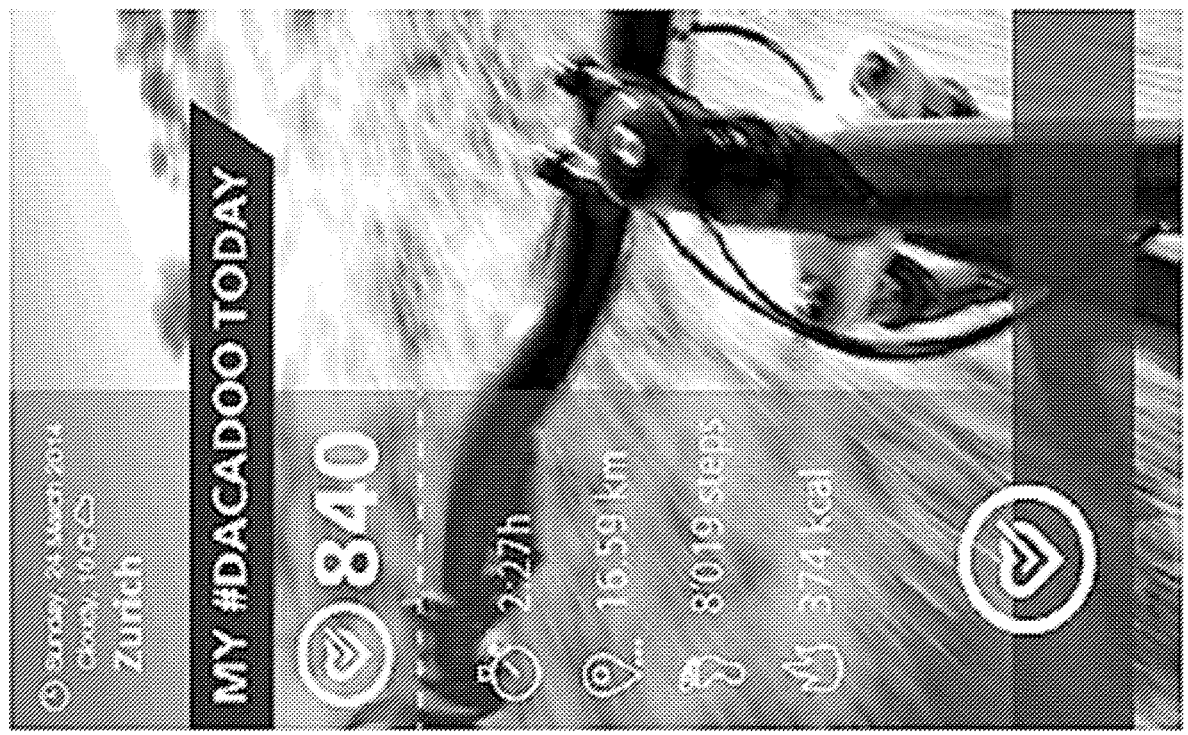

FIG. 26 shows an example display screen 2600 that can be provided via server 180 and/or client 160 on a user's mobile computing device in various contexts, and that includes a user's current Health Score and current values associated with calculating the user's Health Score. In the example, shown in FIG. 26, the user's Health Score is calculated as 840, and respective values are shown representing time, distance, steps and energy. In the example display screen 2600, the Health Score values are provided in a convenient and attractive layout that can be, for example, a start-up screen to a mobile application, a social network or other computing environment that is used and/or frequented by a user.

Figure 27:
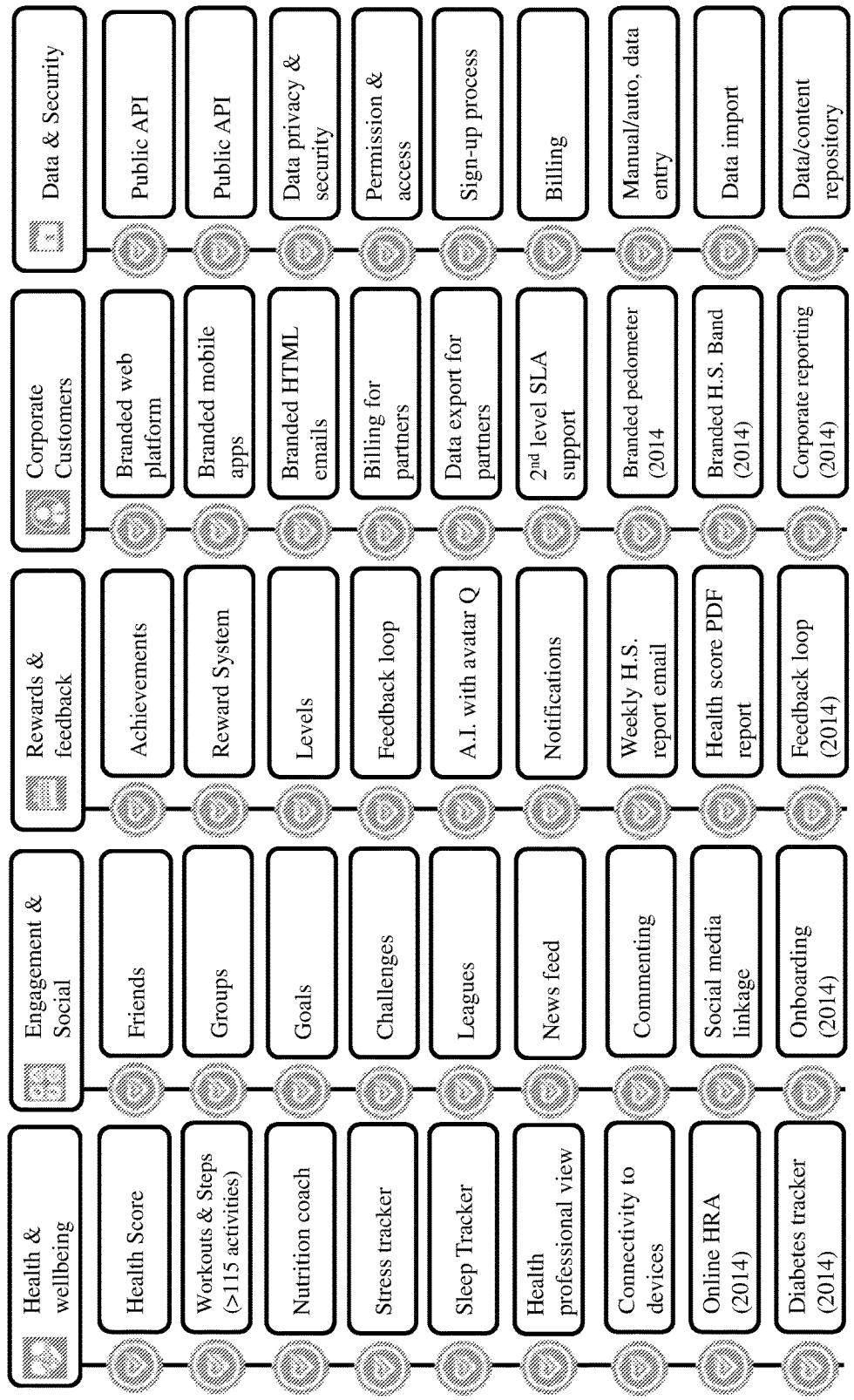

FIG. 27 is a schematic block diagram 2700 according to one or more implementations of the present application. Illustrated in diagram 2700 are components associated with health and well-being, social networking activity, rewards and feedback, corporate customers and data security. Corresponding features, such as shown and described herein, are provided under the respective components.

Referring now to an alternative implementation of the present application in connection with computing hardware and software, in one or more implementations the present application supports always-on sensors that assist in improving the usability and usefulness of the present application. Moreover, one or more smart devices that are accessed by a user of the present application can be configured with a motion-processing processor (e.g., a chip) that serves as an aid to respective tracking functionality, such as shown and described herein. Such motion-processing can be usable in to detect users' gestures and movements and corresponding activity. By recognizing gestures and movements and maintaining an archive of related information over time, information can be tracked to determine whether a user is engaging in specific activities that directly impact the user's mental and physical health.

In one or more implementations, a user's mobile computing device is configured with a plurality of processors, of which at least one remains in an active state and capable of processing information, such as from accelerometers to detect speed, gyroscopes to detect orientation, compasses to detect direction, microphones to detect sound, and biosensors to detect health information that is configured for relatively passive monitoring. At least one second processor can be provided that is configured to perform more robust processing than that of the at least one first processor. In one or more implementations, a first software program executes on the first at least one (e.g., low-level) first processor and that configures the processor to interrogate sensors, such as an accelerometer, gyroscope, compass, microphone and/or biosensor. Moreover, the first at least one processor may be configured to access or otherwise maintain one or more event logs of information that is provided by the respective sensors. The event log(s) are usable for providing historical trends and/or tracking information associated with a user over time, including relating to gesture-based activity, exposure to various conditions (e.g., sound conditions). In this way, an event log of information can be maintained and usable in connection with various functionality shown and described herein and that can be maintained regardless of the state of the second (e.g., more robust) at least one processor to a user. Such a multi-processor implementation can be usable to enable reduce energy demands and processing times associated with relatively robust processors and, consequently, improve battery performance associated with such information gathering processes.

In one or more implementations, the first at least one processor can be configured to invoke one or more processes that effectively awaken the second at least one processor from a "sleep" state, and to access and/or process information, such as to cause information to be displayed or otherwise provided to the user. In this configuration, information can be collected, aggregated and passed on for additional processing while the user's mobile computing device appears to be "asleep" and without tying up the main processor and draining the battery. By supporting always on motion and sensor processing, the present application supports efficient and effective recognition of current activity, user habits, intentions and environments. As a result, the present application is operable to promote a user's well-being by detecting certain modes of behavior, such as walking, taking part in a conversation, or sleeping, as well as by detecting biological and/or physiological information associated with a user.

In one or more implementations, the present application supports data modeling, of which an example is shown and described herein as the "Subject Object Model" ("SOM"). The SOM can be implemented as a module that includes instructions that are executable on a processor for performing the functionality shown and described herein. For example, the instructions encoded in a memory that, when executed by one or more processors 124 cause the processor(s) 124 to manage and model data sent and received by computing respective devices. An example SOM can include data elements referred to herein, generally as "subjects," which can include users that "own" data objects, such as those that relate to exercise workouts. Subjects can be related to each other by the virtual (or physical) relationship, and data objects can be shared between subjects.

Information and program functionality associated with subjects (e.g., users and user groups) and data objects can be demonstrated as related to each other by means of a social graph, and subjects can flexibly share data with each other and on the Internet. Data objects can range from weightings owned by individual users to more complex objects, such as challenges owned by groups. The present application supports managing information associated with subjects, their relations, their objects and the sharing thereof. The SOM can be configurable to capture and provide for access control, thereby allowing for centralized data security. Additionally, the generic nature of the SOM allows for a natural mapping, for example to a RESTful API.

As shown and described herein, a plurality of modules can interact that comprise and/or contribute to the SOM module. Example modules include Subject Kinds, Object Kinds, Relations, Shares, Access Control, Token Based Access Control, Privileges and Permissions, Account Privileges, App Privileges, Token Privileges, Permissions, Access Control Conditions, and Administrative Access.

The SOM can include subjects, such as users, that own objects, such as workouts. The subjects can be related to each other and objects can be shared with other subjects.

This document contains the following:
motivation of the SOM
a description of concrete subjects and objects within the model
an explanation of relations and shares
an explanation of the access control principles
a discussion of implementation aspects.

The following topics can be implemented by server 180 and/or client 160:
data modelling techniques
social graph models (particularly the Follower-Leader-Mutual model)
feed models (particularly the Activity Feed model)
access control models
database systems
Internet standards and practices (for example OAuth 2.0 and RESTful API design).

The invention includes functionality for managing subject-owned data objects. Subjects, such as users and groups, are related to each other by means of a social graph, and subjects can flexibly share data with each other and on the Internet. Data objects range from weightings owned by individual users to more complex objects such as challenges owned by groups. The SOM provides a universal access control model, allowing for centralized data security. Additionally, the generic nature of the SOM allows for a natural mapping to a RESTful API.

The SOM supports various example subject kinds, including, but not limited to:

| Subject Kind | Description |
| --- | --- |
| user | An individual user |
| group | A group, typically of users |
| app | An application accessing the platform |
| system | The technical platform owner; a singleton |
| public | An anonymous user representing the Internet at large, including users not logged in and search engine bots; a singleton. |

The SOM supports various example object kinds, including, but not limited to:

| Object Kind | Description |
| --- | --- |
| comment | A comment, for example on a news post or in a conversation |
| healthscore | Health Score data of a user |
| medium | Media of a user, such as profile pictures, photos, and videos |
| move | A background activity or workout performed by a user |
| movement | Daily summary of movement activity of a user |
| permission | A permission granted on the owner subject to a recipient subject. |
| post | A news post, for example on a workout or earned achievement |
| sysactivity | An activity catalog entry, such as walking, owned by the system subject |
| sysstring | A localization entry, owned by the system subject |
| weight | A weight entry |

In one or more implementations, relations relate one subject to another. Accordingly, relations can be construed as directed, i.e. the model can be asymmetrical. In one or more example implementations, the following terms are used:

Follower: A subject that follows another subject is considered to be a follower of that subject.

Leader: A subject that has another subject as a follower is considered to be a leader of that subject. (For communication purposes the term, "leader," is typically substituted by the term "following" in front ends, i.e. a user is considered to have n followers and to be following m. Technically, following "m" is the same as having "m" leaders. While it is undisputed that the following terminology makes sense for front ends, the use of a verb form to designate a subject role leads to undesirable ambivalence and asymmetry in technical naming, thereby resulting in use of the terms "follower" and "leader" on the technical side.)

Mutual: Two subjects that follow each other are considered to be mutual. This is a virtual relation resulting from two underlying relations. In other terms, the follower-leader-mutual model is a directed graph where the nodes are subjects and the vertices are relations.

Following implies granting the leader read access on the follower.

Shares relate an object to a subject other than the owning subject. A share allows the recipient to read the shared object. In addition, the share carries an affinity. The affinity is a numerical representation of the relatedness of the subjects with regard to the shared object. Affinity functions to present shared objects, such as news posts, including in a predefined order of relevance.

An access control model is provided that supports one or more of the following:

A user keeps his/her weight data private.

A user shares workout information with everybody in a group.

A user shares an individual workout with the world, i.e. the Internet at large.

A user shares blood values with a physician.

A user creates a challenge in a group administrated by the user.

A user shares profile information with the world, including users who are not logged in, and automated tools such as search engine bots.

Authorized personnel, e.g., employees, can reset the password of any user.

An authorized user can perform various administrative actions when logged into the administrative apps; but other apps, such as those from 3rd parties, may not be able to perform administrative actions when the same user is logged in.

An official app creates users; but not necessarily 3rd party apps.

An internal app can process the weights of all users.

In one or more implementations, access control is effected as a function of tokens, such as those that are acquired using the OAuth 2.0 standard. For example, various grants are supported including:

Authorization Code Grant
Implicit Grant
Resource Owner Password Credentials Grant
Client Credentials Grant The first of the grants identified above can operate to authorize an app to access the platform on behalf of a user. The flows may only differ by the way credentials and tokens are exchanged. The final flow can operate to authorize an app to access the platform without reference to a particular user. The flows identified above can be related in that an app acquires a token that subsequently allows the app to perform a defined set of operations (function) on a defined space of data.

In one or more implementations, privileges and permissions are supported.

A privilege can include an absolute right granted and that is independent of a data space. Hence, privileges can be centered on function.

A permission grants a recipient subject the right to access a particular kind of data owned by the granting subject. Hence, permissions can be centered on data (both subject and object data).

Each subject can be associated with a related account on the account management system. The account management system is run separately for security reasons. Each account can have any of the account privileges listed below.

| Account Privilege | Description |
| --- | --- |
| account | Retrieve any account |
| audit | Retrieve audit trails |
| delete | Delete any account |
| factor | Set security factors (such as password) on any account |

-continued

| Account Privilege | Description |
|---|---|
| key | Retrieve encryption keys for any account |
| parameter | Query any account for token parameters |
| privilege | Set privileges on any account |

| Token Privilege | Description |
|---|---|
| relation | Allows access to relations |
| <subject> | Allows access to subjects of the corresponding kind, e.g. user. |
| <object> | Allows access to objects of the corresponding kind, e.g. healthscore. |

Each app can have any of the following app privileges listed below.

| App Privilege | Description |
|---|---|
| autoapprove | Users do not need to manually authorize application for access |
| createapp | The app can create apps |
| creategroup | The app can create groups |
| createuser | The app can create users |
| multitoken | The app can have more than one concurrent token per user |

Some apps, such as 3rd party apps, may not have any of these privileges.

Tokens can have one or more of the token privileges listed below.

Token privileges can be assigned when a token is acquired via OAuth. In such case, the app can have full control over the privileges requested, but unless the app has the autoapprove privilege, the user is presented with and confirms the requested access. In one or more implementations, the OAuth 2.0 standard uses the term scope for the list of token privileges requested.

Permissions can have the following structure:
Owner subject
Recipient subject
Kind (subject or object)

A permission can allow the recipient subject (typically a user or app) to access the specified kind of data owned by the granting subject. (A subject kind different from the subject kind of the granting subject has no effect unless the granting subject is system, see below.)

Access Control Conditions: Regular Access and Administrative Access.

Generally, regular access control conditions are guided by these principles:
Following and shares imply read access
Permissions imply read/write access
Privileges are pre-requisites The following specific terminology can be used in one or more implementations to describe access control conditions:
Transitive subjects. Transitive subjects include the group kind and the public kind. Other kinds of subjects are not transitive.
Token subjects. The token subjects include the app, and optionally the user on behalf of which the token was issued.

| Subject or Object | Operation | Conditions |
|---|---|---|
| Subject | Create | App: has create<subject> privilege<br>Token: has <subject> privilege |
| | Read | Token: has <subject> privilege<br>Token subjects:<br>user is the subject, or<br>user is a leader of the subject, or<br>user is a leader of a transitive subject that is a leader of the subject, or<br>user or app has <subject> permission on the subject, or<br>public is a leader of the subject |
| | Update/Delete | Token: has <subject> privilege<br>Token subjects:<br>user is the subject, or<br>user has <subject> permission on the subject |
| Object | Create | Token: has <object> privilege<br>Token subjects:<br>user is the owner subject of the object, or<br>user or app has <object> permission on the owner subject |
| | Read | Token: has <object> privilege<br>Token subjects:<br>user is the owner subject of the object, or<br>user has a share on the object, or<br>user is a leader of a transitive subject that has a share on the object, or<br>user or app has <object> permission on the owner subject of the object, or<br>public has a share on the object |
| | Update/Delete | Token: has <object> privilege<br>Token subjects:<br>user is the owner subject of the object, or<br>user or app has <object> permission on the owner subject |

With regard to administrative access, a user can be given permission on the system subject for any subject or object kind. This allows the user to access all data of the respective kind. However, these permissions take effect only if a token is issued on behalf of an app with the "systempermission" privilege.

The system permission privilege can only be granted to confidential clients (such as web apps), and not to public clients, such as mobile apps. This is because public clients are ultimately unable to protect their client secret.

Examples revisited in accordance with one or more example implementations of the present application.

The following re-visits examples from above and explains how each case is addressed in the SOM. Although some of the following text includes phrases such as "the user grants" users may not actually carry out interactions at this operational level. Instead, users are given simple interfaces to select options that result in instructions being executed by one or more processors and to carry out various tasks. Yet other tasks are fully automated and/or only affect administrators. Below are a series of optional configurations:

A user keeps his/her weight data private.
Solution: This is the default. If weights have no share and the user grants no permissions, all data are private, except for administrative access.

A user shares all his/her workouts with everybody in a group.
Solution: The user sets sharing settings for the workout category to groups. As a result, whenever a workout is created, a share is created for each group the user is following. Group membership of users is implied by the group and the users being mutuals. Hence, as a corollary, each user "in the group" is a leader of the group. The workouts are thus shared because each user "in the group" is a leader of a transitive subject (the group) that has a share on the workouts.

If a user stops following a group, but the group continues to follow the user, the user can be still authorized to see workouts by other group members. However, the workouts do not show up in regular listings such as news feeds as only objects from subjects the user is actually following are shown. To phrase this another way: the group following the user authorizes the user to see the data; the user following the group makes him see the data. Both conditions must hold for the user to actually see the data. This naturally coincides with the mutual relationship between the user and the group where each side controls its end of the relationship.

If the user owning the workouts stops following the group, shares are no longer created for subsequent workouts and these workouts are thus no longer shared with the group.

A user shares an individual workout with the world, i.e. the Internet at large.

Solution: The user shares the workout with public, pushing a respective share on the individual workout object. (In practice, the user may be clicking Share on a news post, causing the underlying objects of kinds post, move and medium to be shared with public.)

A user shares his/her blood values with a physician.

Solution: The user grants lipid and glucose permissions to the physician.

A user creates a challenge in a group (s)he administrates.

Solution: The group creator (who initially has all permissions on the group) grants challenge permission on the group to the user. (Specifically, this requires the group creator to have permission on the group.)

A user shares his/her profile with the world, i.e. users not logged in and search engine bots Solution: The user follows public.

Authorization is provided for a user to reset the password of any user.

Solution: The master user created during bootstrap phase of the system uses his or her privilege on the account system to assign the factor account privilege to the user.

An authorized user performs administrative actions when logged into an administrative app; but other apps, including those from 3rd parties, must not be able to perform administrative actions when the same user is logged in.

Solution: The user is assigned the required permissions on the system subject. The administrative app is assigned the system privilege; the other apps are not assigned system privilege, rendering the system permissions granted to the user effect free in the context of those apps.

An official app creates users; but 3rd party apps must not be able to create users.

Solution: The official app is assigned the createuser privilege.

An internal app processes the weights of one or more users.

Solution: The internal app is given weight permission on the system subject, and the app is assigned the system privilege.

The following provides additional aspects of implementing the SOM, in accordance with an example implementation.

The SOM can favor read performance over write performance. Essentially, the basic assumption is that there are more reads than writes. This is true for an individual user. If a user posts a workout, this is one write. Whenever the users open a workout overview or a news stream, there is one read. As workouts stay in the overview of the user for a reasonable amount of time, it is thus reasonable to assume that reads outnumber writes. The ratio increases even more in favor of reads if the workout is shared.

For sharing, the effort can be spent when an object is created and a share is pushed onto the shares array for each subject the owner follows. This process in known as fan out. Shares do not need to be selected in their entirety. MongoDB, for example, allows for selection of a matching share only (for the purpose of extracting the related affinity.) The fan out and affinity calculation can be conducted asynchronously in the background.

Relations can be implemented by a relations collection, which can be indexed on both leaders and followers, for example, by taking advantage of index covers for ID-only selections. In addition, indexes can include a suitable unique constraint to improve efficiency. In addition, transitive leaders of a subject can be maintained redundantly on the subject in a transitiveLeaders array. This allows mutuals of a transitive subject to efficiently select each other. For example if a group and 1000 users are mutuals, each user can select the other 999 users, e.g., in a directory query.

The SOM can map naturally to a RESTful API using URL patterns as follows:

| URL | Type | Methods | Purpose |
|---|---|---|---|
| / | root | GET | Starting point |
| /users | collection | GET, POST | User directory; user creation |
| /users/{userId} | entity | GET, POST, PUT, DELETE | User read-update-delete operations |
| /users/{userId}/weights | collection | GET, POST | User-bound weight query and creation |
| /weights | collection | GET | Global weight query, e.g. for syncing |
| /weights/{weightId} | entity | GET, POST, PUT, DELETE | Weight read-update-delete operations |
| /users/{userId}/posts | collection | GET, POST | User-bound post query and creation |
| /posts | collection | GET | Global post query, e.g. for syncing |
| /posts/{postId} | entity | GET, POST, PUT, DELETE | Post read-update-delete operations |
| /posts/{postId}/comments | collection | GET, POST | Post-bound comment query and creation |
| /comments | collection | GET | Global comment query, e.g. for syncing |
| /comments/{commentId} | entity | GET, POST, PUT, DELETE | Comment read-update-delete operations |
| /system/ | root | GET | System starting point (admin apps) |
| /system/activities | collection | GET, POST | System activity query and creation |
| /system/activities/{activityId} | entity | GET, POST, PUT, DELETE | System activity read-update-delete operations |

In the above table, the following notes can apply:
user is an examples for any generic subject kind
weight and post are examples for any generic object kind
comment is an example for an object kind bound to both
   a subject (user, typically) and an object (post, in this case)
system is an example for a singleton subject kind
activities is an example for an object kind owned by a singleton subject
Global collections, such as/weights and/users naturally support use cases such as data syncing or a user directory query
Use cases such as retrieving the final state of the Health Score of everybody a user follows or showing a Live Map for all members of a group are naturally addressed by collections such as /users/{userId}/healthscores and /groups/{groupId}/moves with appropriate query parameters In addition to the SOM module, the present application includes product and user-experience. In one or more implementations, a dynamic Feedback Loop ("FL") module can be provided that includes instructions that, when executed by server 180 and/or client 160, ties together user interactions. The FL module can be configured to operate in a dynamic and self-learning way, and to make the overall user experience, from signup to regular use, far more engaging and attractive.

Although the Health Score of the present application can appear to be a linear combination of the scores of three pillars associated with Body, Activity and Feelings, the information associated with each of pillars may be processed in interactive way, thus making the Health Score a nonlinear combination of its components, including with the advent of the Feedback Loop.

From a user perspective, transparency is a component that includes user interaction with the FL, based on several functional implementations, of which a non-limiting list of examples are described below:

1. An explanation component that includes an informational messaging module that is configured to transmit a message (including a prompt) to a user regarding the Health Score.

2. The overall score and, potentially, the component scores, can include a 5-class, color-coded relative scale (poor, fair, good, very good, excellent) based on a user score distribution using fixed percentile cuts.

3. Users can be provided with a Health Score after providing the platform with four values, age, sex, height, and weight, which can be accompanied by a range that can progressively narrow as users input the full set of values needed for an accurate Health Score. The startup value of this score can be purposely on the low side, such as based on a 30-percentile value of the user distribution for the given parameter, where available, so that users generally see an improvement as they add input parameters and engage with the platform.

4. A Health Score Simulator can allow users to see how their scores are likely to evolve given the observed trend, and a target score can be presented to the user. The meaning of this can also be made clearer to the user by including a graph showing the score evolution over time.

5. The total score can be calculated as a linear combination of the metric, quality of life, and lifestyle scores, with equal weights.

6. All lifestyle components can be active at all times, and is engaging and as unobtrusive as possible.

Given the central importance of the Health Score and its impact in connection with one or more social network functions, user actions that lower a Health Score, such as a response to a Quality of Life question, or to other self-assessment questions are almost invariably biased. To compensate for this, a Truth Points module can be provided that provides, in one or more implementations, points that are awarded to a user whenever a self-assessment response, or manual input, results in a decrease of the Health Score, which is presumed accurate.

In one or more implementations, a data platform in accordance with the present application is configured to send acquired parameters to an analytical engine, which can be configured to deal with all missing values. All default or imputation values can be set by the analytical engine.

In the general area of accuracy, the following options can be provided changes:

1. Parameters can be imputed depending on identified user characteristics. This addresses mainly medical history, and prepares the platform for an evolution in user-acquisition of specific parameters.

2. Soliciting user input on medical history can be made conditional on existing knowledge, thus generally streamlining the onboarding process.

3. Imputation models for metabolic and other parameters are supported.

4. Precursor risks have been included, for example for diabetes, kidney disease, and heart failure.

5. Cardiovascular risk models are supported.

6. Modulator models are supported.

7. A simplified and accurate sensitivity function can be included. This functionality can address lifestyle change directly, without recourse to underlying indirect risk factors and a constant sensitivity matrix.

8. A metric health model score can be tuned to have its median at 500 and can be based on user data.

Further, Quality of Life Model (QLM) scores can be dynamical and context driven, meaning that QLM questions can be pushed to users, instead of simply suggesting to users that they visit the QLM input page.

As noted herein, the Lifestyle Model (LSM) includes modules that can be active for all users. The various modules can require different startup times, and the baseline value of the corresponding scores can be low, thereby avoiding the initial overload of new information for new users.

Sleep and Stress trackers and scores are provided that include measurement of stress or sleep quality Tracking is provided in a passive mode, and push notifications can be contextual and unobtrusive.

Further a Movement component can be provided that includes physical activities, and combines categories wherever possible, a case in point being background (steps) activity and walking for example.

Nutrition tracking can be dynamical, based not only on long-term habits, but also on recent events; scoring can likewise include short-term fluctuations over a long-term score. In addition, the tracker can include an implementation of a true Mediterranean Diet Adherence Screener ("MEDAS") score, and scoring of individual food groups, which can in turn lead to a better and more accurate estimate of the effect of nutrition on the Health Score.

Further, a weight management score can be the result of a composite input, with additional input coming from the Activity and Movement components. The weight management score can be based on the weight of the user as well as weight change as part of the score.

A smoking cessation component can be activated for all users, and the initial score can be based on current population statistics.

In one or more implementations, the lifestyle components interact with each other, and interact with the other pillars of Health Score, shown and described herein. This strongly suggests that tight coupling between the associated behaviors is likely to lead to strong predictive models that use any and all measures to predict one or more behavioral outcomes. For example, a measure of chronic psychological stress, or other affective disorder can be obtained from self-assessment questions triggered by FL. Similarly, answers to one or two simple questions can allow for quality of sleep assessment. These outcomes can be affected by each other and by other behavioral issues, such as physical activity and nutrition. Models that use physical activity, nutrition characteristics, and sleep quality as predictors can be included that can predict psychological stress in an individual, and point to correlations between stress and other lifestyle factors.

Thus, as shown and described herein FL is usable to configure a server 180 and/or client 160 to make actionable and precise observations and recommendations, based on values of the sets of predictors, on how a particular user can improve his or her quality of sleep, or reduce his or her level of stress.

In one or more implementations, frustration (as known in the art) can occur in certain cases when improving contribution of an attribute and that decreases the contributions of other attributes. Strong frustration can exist when the effect decreases a more general or larger value.

Furthermore, attributes can be included that represent types of features that are used in the calculation of a Health Score, such as physical qualities, components, and abilities. Attributes can vary qualitatively, quantitatively, or in more complex ways (e.g., dual varying attributes). An attribute can be variable and have characteristics that include a set of possible instantiations for the attribute.

In one or more implementations, an interaction can occur when a characteristic expressed by one attribute influences how a characteristic by another attribute contributes to a Health Score or other related value. When this occurs, the first attribute interacts with the second attribute. Further, frustration can exists when changing a characteristic expressed by one attribute (1) increases the contribution that the attribute makes to a Health Score, while simultaneously (2) decreasing the contribution to Health Score made by other attributes. When the result of frustration is a decrease in the value of the Health Score, it is referred to herein, generally, as strong frustration.

Thus, as shown and described herein, a health navigator provides a lifestyle feedback engine to a health score platform that delivers continuous coaching and notifications for individuals with respect to the individual's lifestyle and activities. Feedback can be customized by a server 180 and/or client 160 to provide individual personality and behavior information that are instrumental to motivate an individual and make positive change, frequency and progress with regard to the individual's health. By leveraging helpful information provided by server 180 and/or client 160, users have autonomy to choose goals and participation in activities that are realistic and attainable. This generates a sense of accomplishment which is further boosted with peer recognition and positive feedback, including from friends and groups who have similar interests and further motivate the individual to complete one or more goals set forth by server 180 and/or client 160.

While the invention has been described in connection with certain embodiments thereof, the invention is not limited to the described embodiments but rather is more broadly defined by the recitations in any claims that follow and equivalents thereof. The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

The various embodiments described above disclose features that can optionally be combined in a variety of ways depending on the desired implementation. It will be appreciated that other embodiments based on different combinations of features are also possible. It will also be appreciated that more than one parameter for a particular parameter type can be used. None of the described features are mutually exclusive, and any combination of can be deployed to achieve the functions described above.

What is claimed:

1. A method for providing health scores of a plurality of individuals, comprising:
   receiving, by at least one processor, health data and extrinsic data as parameters for computation of a health score of a first individual;
   verifying, by at least one processor, integrity of at least one of the received health data and the received extrinsic data by confirming at least one of the received health data and the received extrinsic data are not less than a minimum value and not more than a maximum value;
   determining, by at least one processor based on the received health data and the received extrinsic data, a likelihood of at least one health risk;
   combining the received health data and extrinsic data using an algorithm being implemented as code executing in at least one processor so as to compute a first health score of the first individual, wherein the algorithm causes parameters comprising one portion of the received health data and extrinsic data to interact with parameters comprising another portion of the received health data and extrinsic data, and further wherein the algorithm accounts for the determined likelihood of at least one health risk in the computed first health score;
   applying, by at least one processor, artificial intelligence to the received health data and extrinsic data to learn statistical lifestyle data of the first individual;
   outputting, by at least one processor to an interface operated by the first individual, the first health score of the first individual;
   determining, by at least one processor at least in part using the determined statistical lifestyle data of the first individual, a plurality of modifiable risk factors that each respectively has potential impact to alter the first health score of the first user;
   calculating, by at least one processor, a second health score of the first individual as a function of the first health score and a respective one of the plurality of modifiable risk factors;
   determining, by at least one processor, a difference between the second health score and the first health score;
   selectively outputting to the interface, by at least one processor, the second health score and, as a function of the determined difference between the second health score and the first health score, information associated with the respective one of the plurality of modifiable risk factors;
   providing, by at least one processor to at least one second computing device, as a function of information received from the first individual, an access token that provides access control rights by others to the first health score of the first individual;
   in response to receiving, by at least one processor, the access token from the at least one second computing device, providing the first health score of the first individual to the at least one second computing device; and
   in response to receiving, by at least one processor, at least one other access token which was previously transmitted to the at least one second computing device, providing at least one health score respectively associated with at least one other of the plurality of individuals and the at least one other access token,
wherein the first health score of the first individual is available to at least one other computing device, as a function of the access token.

2. The method of claim 1, wherein the first health score is presented in the interface as falling in one of a plurality of predefined bands, wherein the bands comprise a relative scale in comparison to fixed percentile criteria.

3. The method of claim 1, further comprising simulating, by at least one processor, score evolution using a trend in the extrinsic data.

4. The method of claim 1, further comprising:
providing, by at least one processor, a feedback loop engine that includes at least one of a user challenge, a group challenge and facts.

5. A system for providing health scores of a plurality of individuals, comprising:
a communication unit operable to receive health data and extrinsic data as parameters for computation of the health scores;
a memory arranged to store the received data;
a processor arranged to execute code stored on non-transitory processor readable media to:
verify integrity of at least one of the received health data and the received extrinsic data by confirming at least one of the received health data and the received extrinsic data are not less than a minimum value and not more than a maximum value;
determine, based on the received health data and the received extrinsic data, a likelihood of at least one health risk;
combine the received health data and extrinsic data using an algorithm being implemented as code executing in the processor so as to compute a first health score of a first individual, wherein the algorithm causes parameters comprising one portion of the received health data and extrinsic data interact with parameters comprising another portion of the data and further wherein the algorithm accounts for the determined likelihood of at least one health risk in the computed first health score;
provide a feedback loop module configured to receive information and to learn statistical lifestyle data of the first individual using artificial intelligence, wherein the feedback loop module is configured for scheduling, processing and delivering notifications including health-related information over various channels;
output the first health score of the first individual to an interface of a computing device operated by the first individual;
determine, at least in part using the determined statistical lifestyle data of the first individual, a plurality of modifiable risk factors that each respectively has potential impact to alter the first health score of the first user;
calculate a second health score of the first individual as a function of the first health score and a respective one of the plurality of modifiable risk factors;
determine a difference between the second health score and the first health score;
selectively output to the interface, the second health score and, as a function of a difference between the second health score and the first health score, information associated with the respective one of the plurality of modifiable risk;
provide, to at least one second computing device as a function of information received from the first individual, an access token that provides access control rights to the first health score of the first individual to others;
provide the first health score of the first individual in response to receiving the access token; and
receive from at least one second computing device in response to receiving at least one other previously transmitted access token, at least one health score respectively associated with at least one other individual of the plurality of individuals and the at least one other previously received access token,
wherein the first health score of the first individual is available to at least one other computing device, as a function of the access token.

6. The system of claim 5, wherein the health score is presented in the interface as falling in one of a plurality of predefined bands, wherein the bands comprise a relative scale in comparison to fixed percentile criteria.

7. The system of claim 5, wherein the processor is further arranged to execute additional code to configure the processor to simulate score evolution using a trend in the extrinsic data.

8. The method of claim 1, further comprising determining by at least one processor relationships of data objects associated with a plurality of health scores of a plurality of individuals, wherein the plurality of health scores are output to the interface of the computing device operated by the first individual as a function of a social graph.

9. The method of claim 8, wherein each of the plurality of health scores is respectively provided by the at least one second computing device as a function of a respective token.

10. The method of claim 1, further comprising transmitting, by at least one processor, to the first individual over a delivery channel chosen by the first individual, a notification associated with the health data or the extrinsic data.

11. The method of claim 1, wherein the at least one health risk includes at least one of a vascular risk, a predecessor risk and a modulator risk.

12. The method of claim 1, further comprising deriving at least one model from at least one study to determine the at least one health risk.

13. The method of claim 12, further comprising modifying the at least one model for consistency and to predict at least one health-related event within a period of time.

14. The method of claim 1, further comprising combining a plurality of models, each model derived from at least one study, to derive the at least one health risk.

15. The method of claim 14, wherein the plurality of models are combined using probabilistic logic.

16. The method of claim 12, further comprising validating, by at least one processor, the first health score over time.

17. The method of claim 1, wherein at least one of the received health data or the received extrinsic data is further verified by at least metadata.

18. The method of claim 1, further comprising:
applying, by at least one processor, information from at least one medical study to at least one data model to derive at least one other health risk; and
determining, as a function of the at least one health risk and the at least one other health risk, a single estimate of a health risk event.

19. The system of claim 5, wherein the processor is further arranged to execute additional code to configure the processor to derive at least one model from at least one study to determine the at least one health risk, and to modify the at least one model for consistency and to predict at least one health-related event within a period of time.

20. The system of claim 5, wherein the processor is further arranged to execute additional code to configure the processor to combine a plurality of models, each model derived from at least one study, to derive the at least one health risk.

\* \* \* \* \*